United States Patent [19]
Friedman et al.

[11] Patent Number: 5,935,810
[45] Date of Patent: Aug. 10, 1999

[54] MAMMALIAN OB POLYPEPTIDES CAPABLE OF MODULATING BODY WEIGHT, CORRESPONDING NUCLEIC ACIDS, AND DIAGNOSTIC AND THERAPEUTIC USES THEREOF

[75] Inventors: Jeffrey M. Friedman; Yiying Zhang, both of New York; Ricardo Proenca, Astoria, all of N.Y.; Margherita Maffei, Asciano, Italy; Jeffrey L. Halaas, New York, N.Y.; Ketan Gajiwala, New York, N.Y.; Stephen K. Burley, New York, N.Y.

[73] Assignee: The Rockefeller University, New York, N.Y.

[21] Appl. No.: 08/347,563

[22] Filed: Nov. 30, 1994

Related U.S. Application Data

[63] Continuation-in-part of application No. 08/292,345, Aug. 17, 1994.

[51] Int. Cl.$^6$ .............. C12N 15/12; C12N 1/15; C12N 1/21; C12N 5/10
[52] U.S. Cl. ............ 435/69.1; 435/172.3; 435/252.3; 435/252.31; 435/252.33; 435/252.34; 435/252.35; 435/254.2; 435/254.21; 435/254.22; 435/254.23; 435/320.1; 435/348; 435/355; 435/357; 435/364; 435/365; 536/23.5; 536/23.4; 536/24.31
[58] Field of Search .................. 536/23.5, 24.31, 536/23.4; 435/320.1, 252.3, 252.31, 252.33, 252.34, 252.35, 254.2, 325, 348, 352, 353, 354, 254.21, 254.22, 254.23, 69.1, 172.3, 355, 357, 364, 365

[56] References Cited

U.S. PATENT DOCUMENTS

| | | | |
|---|---|---|---|
| 5,521,283 | 5/1996 | DiMarchi et al. | 530/324 |
| 5,525,705 | 6/1996 | DiMarchi et al. | 530/324 |
| 5,532,336 | 7/1996 | DiMarchi et al. | 530/324 |
| 5,552,522 | 9/1996 | DiMarchi et al. | 530/324 |
| 5,552,523 | 9/1996 | Basinski et al. | 530/324 |
| 5,552,524 | 9/1996 | Basinski et al. | 530/324 |
| 5,554,727 | 9/1996 | Basinski et al. | 530/324 |
| 5,559,208 | 9/1996 | Basinski et al. | 530/317 |
| 5,563,243 | 10/1996 | DiMarchi et al. | 530/324 |
| 5,563,244 | 10/1996 | DiMarchi et al. | 530/324 |
| 5,563,245 | 10/1996 | DiMarchi et al. | 530/324 |
| 5,567,678 | 10/1996 | DiMarchi et al. | 530/324 |
| 5,567,803 | 10/1996 | Basinski et al. | 530/324 |
| 5,569,743 | 10/1996 | DiMarchi et al. | 530/324 |
| 5,569,744 | 10/1996 | Basinski et al. | 530/324 |
| 5,574,133 | 11/1996 | DiMarchi et al. | 530/324 |
| 5,580,954 | 12/1996 | DiMarchi et al. | 530/324 |
| 5,594,101 | 1/1997 | Becker et al. | 530/317 |
| 5,594,104 | 1/1997 | Basinski et al. | 530/324 |
| 5,605,886 | 2/1997 | Basinski et al. | 514/12 |
| 5,614,379 | 3/1997 | MacKellar et al. | 435/68.1 |
| 5,643,748 | 7/1997 | Snodgrass et al. | 435/69.1 |
| 5,691,309 | 11/1997 | Basinski et al. | 514/12 |
| 5,698,389 | 12/1997 | de la Brousse | 435/4 |

FOREIGN PATENT DOCUMENTS

| | | |
|---|---|---|
| 725078 A1 | 8/1996 | European Pat. Off. . |
| 725079 A1 | 8/1996 | European Pat. Off. . |
| 736599 A2 | 10/1996 | European Pat. Off. . |
| 741187 A2 | 11/1996 | European Pat. Off. . |
| 743321 A2 | 11/1996 | European Pat. Off. . |
| 744408 A2 | 11/1996 | European Pat. Off. . |
| 745610 A2 | 12/1996 | European Pat. Off. . |
| 759441 A2 | 2/1997 | European Pat. Off. . |
| 764722 A2 | 3/1997 | European Pat. Off. . |
| 784979 A2 | 7/1997 | European Pat. Off. . |
| 784981 A2 | 7/1997 | European Pat. Off. . |
| 784982 A2 | 7/1997 | European Pat. Off. . |
| 786256 A2 | 7/1997 | European Pat. Off. . |
| 797999 A2 | 10/1997 | European Pat. Off. . |
| 8-333394 | 12/1996 | Japan . |
| 9-3098 | 1/1997 | Japan . |
| WO 96/05861 | 2/1996 | WIPO . |
| WO 96/22308 | 7/1996 | WIPO . |
| WO 96/23513 | 8/1996 | WIPO . |
| WO 96/23514 | 8/1996 | WIPO . |
| WO 96/23515 | 8/1996 | WIPO . |
| WO 96/23516 | 8/1996 | WIPO . |
| WO 96/23517 | 8/1996 | WIPO . |
| WO 96/23518 | 8/1996 | WIPO . |
| WO 96/23519 | 8/1996 | WIPO . |
| WO 96/23520 | 8/1996 | WIPO . |
| WO 96/23815 | 8/1996 | WIPO . |
| WO 96/24670 | 8/1996 | WIPO . |

```
MOUSE   MCWRPLCRFL WLWSYLSYVQ AVPIQKVQDD TKTLIKTIVT RINDISHTQS    50
        * **  *         *  *
HUMAN   MHWGTLCGFL WLWPYLFYVQ AVPIQKVQDD TKTLIKTIVT RINDISHTQS

MOUSE   VSAKQRVTGL DFIPGLHPIL SLSKMDQTLA VYQQVLTSLP SQNVLQIAND   100
          *                   -             -   -    *     *
HUMAN   VSSKQKVTGL DFIPGLHPIL TLSKMDQTLA VYQQILTSMP SRNVIQISND

MOUSE   LENLRDLLHL LAFSKSCSLP QTSGLQKPES LDGVLEASLY STEVVALSRL   150
            -          *   **  ***-    *   *
HUMAN   LENLRDLLHV LAFSKSCHLP WASGLETLDS LGGVLEASGY STEVVALSRL

MOUSE   QGSLQDILQQ LDVSPEC                                       167
          - *        - *
HUMAN   QGSLQDMLWQ LDLSPGC
```

| | | |
|---|---|---|
| WO 96/27385 | 9/1996 | WIPO . |
| WO 96/29405 | 9/1996 | WIPO . |
| WO 96/31526 | 10/1996 | WIPO . |
| WO 96/34111 | 10/1996 | WIPO . |
| WO 96/34885 | 11/1996 | WIPO . |
| WO 96/35787 | 11/1996 | WIPO . |
| WO 96/36641 | 11/1996 | WIPO . |
| WO 96/36644 | 11/1996 | WIPO . |
| WO 96/37517 | 11/1996 | WIPO . |
| WO 96/38152 | 12/1996 | WIPO . |
| WO 96/38586 | 12/1996 | WIPO . |
| WO 96/40912 | 12/1996 | WIPO . |
| WO 97/00319 | 1/1997 | WIPO . |
| WO 97/00866 | 1/1997 | WIPO . |
| WO 97/02004 | 1/1997 | WIPO . |
| WO 97/06816 | 2/1997 | WIPO . |
| WO 97/11192 | 3/1997 | WIPO . |
| WO 97/12037 | 4/1997 | WIPO . |
| Wo 97/13500 | 4/1997 | WIPO . |
| WO 97/15322 | 5/1997 | WIPO . |
| WO 97/16189 | 5/1997 | WIPO . |
| WO 97/16550 | 5/1997 | WIPO . |
| WO 97/18228 | 5/1997 | WIPO . |
| WO 97/18806 | 5/1997 | WIPO . |
| WO 97/18833 | 5/1997 | WIPO . |
| WO 97/19952 | 6/1997 | WIPO . |
| WO 97/20933 | 6/1997 | WIPO . |
| WO 97/24440 | 7/1997 | WIPO . |
| WO 97/25424 | 7/1997 | WIPO . |
| WO 97/25425 | 7/1997 | WIPO . |
| WO 97/26004 | 7/1997 | WIPO . |
| WO 97/26011 | 7/1997 | WIPO . |
| WO 97/26012 | 7/1997 | WIPO . |
| WO 97/26013 | 7/1997 | WIPO . |
| WO 97/26335 | 7/1997 | WIPO . |
| WO 97/26523 | 7/1997 | WIPO . |
| WO 97/26916 | 7/1997 | WIPO . |
| WO 97/27286 | 7/1997 | WIPO . |
| WO 97/28824 | 8/1997 | WIPO . |
| WO 97/31015 | 8/1997 | WIPO . |
| WO 97/32022 | 9/1997 | WIPO . |
| WO 97/35620 | 10/1997 | WIPO . |
| WO 97/38014 | 10/1997 | WIPO . |
| WO 97/40380 | 10/1997 | WIPO . |
| WO 97/41217 | 11/1997 | WIPO . |
| WO 97/41263 | 11/1997 | WIPO . |
| WO 97/42340 | 11/1997 | WIPO . |
| WO 97/46585 | 12/1997 | WIPO . |
| WO 97/46587 | 12/1997 | WIPO . |

OTHER PUBLICATIONS

Fletcher et al., Experimental Hematology 24(9):1055, abstract 172 (1996).
Fletcher et al., Blood 86(10 Suppl. 1):241A, abstract 951 (1995).
Bahary et al., 1993, Mammalian Genome 4:511–15.
Bahary et al., 1993, Genomics 16:113–22.
Friedman and Leibel, 1992, Cell 69:217–20.
Bahary et al., 1992, Genomics 13:761–69.
Friedman et al., 1991, Ann. NY Acad. Sci. 630:100–115.
Friedman et al., 1991, Mammalian Genome 1:130–44.
Friedman et al., 1991, Genomics 11:1054–62.
Moll et al., 1991, Am. J. Hum. Genet. 49:1243–55.
Truett et al., 1991, Proc. Natl. Acad Sci. USA 88:7806–09.
Walther et al., 1991, Genomics 11:424–34.
Bahary, 1990, Proc. Natl. Acad. Sci. USA 87:8642–46.
Harris, 1990, FASEB J. 4:3310–18.
Leibel et al., 1990, "Genetic variation and nutrition in obesity: Approaches to the molecular genetics of obesity", *World Review of Nutrition and Dietetics*, vol. 63 (Simopoulos, A.P. and Childs, B., eds.), pp. 90–101.
Bray, 1989, Am. J. Clin. Nutr. 50:891–902.
Harris et al., 1987, Diabetes 36:523–34.
Bogardus et al., 1986, N. Engl. J. Med. 315:96–100.
Keesey and Powley, 1986, Ann. Rev. Psychol. 37:109–33.
Coleman, 1978, Diabetologia 14:141–48.
Coleman, 1973, Diabetologia 9:294–98.
Hervey, 1959, J. Physiol. 145:336–52.
Dickie and Lane, 1957, Mouse News Lett. 17:52.
Ingalls et al., 1950, J. Hered. 41:317–18.

*Primary Examiner*—Johnny F. Railey, II
*Attorney, Agent, or Firm*—Klauber & Jackson

[57] ABSTRACT

The present invention relates generally to the control of body weight of animals including mammals and humans, and more particularly to materials identified herein as modulators of weight, and to the diagnostic and therapeutic uses to which such modulators may be put. In its broadest aspect, the present invention relates to the elucidation and discovery of nucleotide sequences, and proteins putatively expressed by such nucleotides or degenerate variations thereof, that demonstrate the ability to participate in the control of mammalian body weight. The nucleotide sequences in object represent the genes corresponding to the murine and human ob gene, that have been postulated to play a critical role in the regulation of body weight and adiposity. Preliminary data, presented herein, suggests that the polypeptide product of the gene in question functions as a hormone. The present invention further provides nucleic acid molecules for use as molecular probes, or as primers for polymerase chain reaction (PCR) amplification, i.e., synthetic or natural oligonucleotides. In further aspects, the present invention provides a cloning vector, which comprises the nucleic acids of the invention; and a bacterial, insect, or a mammalian expression vector, which comprises the nucleic acid molecules of the invention, operatively associated with an expression control sequence. Accordingly, the invention further relates to a bacterial or a mammalian cell transfected or transformed with an appropriate expression vector, and correspondingly, to the use of the above mentioned constructs in the preparation of the modulators of the invention. Also provided are antibodies to the ob polypeptide. Moreover, a method for modulating body weight of a mammal is provided. In specific examples, genes encoding two isoforms of both the murine and human ob polypeptides are provided.

27 Claims, 35 Drawing Sheets

FIG. 1

```
ATATTGCTGAGCTCAGGGAGTGAGGGCCCCACATTTGAGACAGTGAGCCCCAAGAAGAGG      60
GATCCCTGCTCCAGCAGCTGCAAGGTGCAAGAAGAAGAAGATCCCAGGGAGGAAAATGTG     120
                                                       M  C       2
CTGGAGACCCCTGTGTCGGTTCCTGTGGCTTTGGTCCTATCTGTCTTATGTTCAAGCAGT     180
 W  R  P  L  C  R  F  L  W  L  W  S  Y  L  S  Y  V  Q  A  V      22
GCCTATCCAGAAAGTCCAGGATGACACCAAAACCCTCATCAAGACCATTGTCACCAGGAT     240
 P  I  Q  K  V  Q  D  D  T  K  T  L  I  K  T  I  V  T  R  I      42
CAATGACATTTCACACACGCAGTCGGTATCCGCCAAGCAGAGGGTCACTGGCTTGGACTT     300
 N  D  I  S  H  T  Q  S  V  S  A  K  Q  R  V  T  G  L  D  F      62
CATTCCTGGGCTTCACCCCATTCTGAGTTTGTCCAAGATGGACCAGACTCTGGCAGTCTA     360
 I  P  G  L  H  P  I  L  S  L  S  K  M  D  Q  T  L  A  V  Y      82
TCAACAGGTCCTCACCAGCCTGCCTTCCCAAAATGTGCTGCAGATAGCCAATGACCTGGA     420
 Q  Q  V  L  T  S  L  P  S  Q  N  V  L  Q  I  A  N  D  L  E     102
GAATCTCCGAGACCTCCTCCATCTGCTGGCCTTCTCCAAGAGCTGCTCCCTGCCTCAGAC     480
 N  L  R  D  L  L  H  L  L  A  F  S  K  S  C  S  L  P  Q  T     122
CAGTGGCCTGCAGAAGCCAGAGAGCCTGGATGGCGTCCTGGAAGCCTCACTCTACTCCAC     540
 S  G  L  Q  K  P  E  S  L  D  G  V  L  E  A  S  L  Y  S  T     142
AGAGGTGGTGGCTTTGAGCAGGCTGCAGGGCTCTCTGCAGGACATTCTTCAACAGTTGGA     600
 E  V  V  A  L  S  R  L  Q  G  S  L  Q  D  I  L  Q  Q  L  D     162
TGTTAGCCCTGAATGCTGAAGTTTCAAAGGCCACCAGGCTCCCAAGAATCATGTAGAGGG     660
 V  S  P  E  C  *                                                167
AAGAAACCTTGGCTTCCAGGGGTCTTCAGGAGAAGAGAGCCATGTGCACACATCCATCAT     720
TCATTTCTCTCCCTCCTGTAGACCACCCATCCAAAGGCATGACTCCACAATGCTTGACTC     780
AAGTTATCCACACAACTTCATGAGCACAAGGAGGGGCCAGCCTGCAGAGGGGACTCTCAC     840
CTAGTTCTTCAGCAAGTAGAGATAAGAGCCATCCCATCCCCTCCATGTCCCACCTGCTCC     900
GGGTACATGTTCCTCCGTGGGTACACGCTTCGCTGCGGCCCAGGAGAGGTGAGGTAGGGA     960
TGGGTAGAGCCTTTGGGCTGTCTCAGAGTCTTTGGGAGCACCGTGAAGGCTGCATCCACA    1020
CACAGCTGGAAACTCCCAAGCAGCACACGATGGAAGCACTTATTTATTTATTCTGCATTC    1080
TATTTTGGATGGATCTGAAGCAAGGCATCAGCTTTTTCAGGCTTTGGGGGTCAGCCAGGA    1140
TGAGGAAGGCTCCTGGGGTGCTGCTTTCAATCCTATTGATGGGTCTGCCCGAGGCAAACC    1200
TAATTTTTGAGTGACTGGAAGGAAGGTTGGGATCTTCCAAACAAGAGTCTATGCAGGTAG    1260
CGCTCAAGATTGACCTCTGGTGACTGGTTTTGTTTCTATTGTGACTGACTCTATCCAAAC    1320
ACGTTTGCAGCGGCATTGCCGGGAGCATAGGCTAGGTTATTATCAAAAGCAGATGAATTT    1380
TGTCAAGTGTAATATGTATCTATGTGCACCTGAGGGTAGAGGATGTGTTAGAGGGAGGGT    1440
GAAGGATCCGGAAGTGTTCTCTGAATTACATATGTGTGGTAGGCTTTTCTGAAAGGGTGA    1500
GGCATTTTCTTACCTCTGTGGCCACATAGTGTGGCTTTGTGAAAAGGACAAAGGAGTTGA    1560
CTCTTTCCGGAACATTTGGAGTGTACCAGGCACCCTTGGAGGGGCTAAAGCTACAGGCCT    1620
TTTGTTGGCATATTGCTGAGCTCAGGGAGTGAGGGCCCCACATTTGAGACAGTGAGCCCC    1680
AAGAAAAGGGTCCCTGGTGTAGATCTCCAAGGTTGTCCAGGGTTGATCTCACAATGCGTT    1740
TCTTAAGCAGGTAGACGTTTGCATGCCAATATGTGGTTCTCATCTGATTGGTTCATCCAA    1800
AGTAGAACCCTGTCTCCCACCCATTCTGTGGGAGTTTTGTTCCAGTGGGAATGAGAAAT    1860
CACTTAGCAGATGGTCCTGAGCCCTGGGCCAGCACTGCTGAGGAAGTGCCAGGGCCCCAG    1920
GCCAGGCTGCCAGAATTGCCCTTCGGGCTGGAGGATGAACAAAGGGGCTTGGGTTTTTCC    1980
ATCACCCCTGCACCCTATGTCACCATCAAACTGGGGGGCAGATCAGTGAGAGGACACTTG    2040
ATGGAAAGCAATACACTTTAAGACTGAGCACAGTTTCGTGCTCAGCTCTGTCTGGTGCTG    2100
TGAGCTAGAGAAGCTCACCACATACATATAAAAATCAGAGGCTCATGTCCCTGTGGTTAG    2160
ACCCTACTCGCGGCGGTGTACTCCACCACAGCAGCACCGCACCGCTGGAAGTACAGTGCT    2220
GTCTTCAACAGGTGTGAAAGAACCTGAGCTGAGGGTGACAGTGCCCAGGGGAACCCTGCT    2280
TGCAGTCTATTGCATTTACATACCGCATTTCAGGGCACATTAGCATCCACTCCTATGGTA    2340
GCACACTGTTGACAATAGGACAAGGGATAGGGGTTGACTATCCCTTATCCAAAATGCTTG    2400
GGACTAGAAGAGTTTTGGATTTTAGAGTCTTTTCAGGCATAGGTATATTTGAGTATATAT    2460
AAAATGAGATATCTTGGGGATGGGCCCAAGTATAAACATGAAGTTCATTTATATTTCAT    2520
AATACCGTATAGACACTGCTTGAAGTGTAGTTTTATACAGTGTTTTAAATAACGTTGTAT    2580
GCATGAAAGACGTTTTTACAGCATGAACCTGTCTACTCATGCCAGCACTCAAAAACCTTG    2640
GGGTTTTGGAGCAGTTTGGATCTTGGGTTTTCTGTTAAGAGATGGTTAGCTTATACCTAA    2700
AACCATAATGGCAAACAGGCTGCAGGACCAGACTGGATCCTCAGCCCTGAAGTGTGCCCT    2760
TCCAGCCAGGTCATACCCTGTGGAGGTGAGCGGGATCAGGTTTTGTGGTGCTAAGAGAGG    2820
AGTTGGAGGTAGATTTTGGAGGATCTGAGGGC                                2852
```

FIG. 2

```
---G--GTTG CAAGGCCCAA GAAGCCCA-- -TCCTGGGAA GGAAAATGCA      50
TTGGGGAACC CTGTG-CGGA TTCTTGTGGC TTTGGCCCTA TCTTTTCTAT     100
GTCCAAGCTG TGCCCATCCA AAAAGTCCAA GATGACACCA AAACCCTCAT     150
CAAGACAATT GTCACCAGGA TCAATGACAT TTCACACACG CAGTCAGTCT     200
CCTCCAAACA GAAAGTCACC GGTTTGGACT TCATTCCTGG GCTCCACCCC     250
ATCCTGACCT TATCCAAGAT GGACCAGACA CTGGCAGTCT ACCAACAGAT     300
CCTCACCAGT ATGCCTTCCA GAAACGTGAT CCAAATATCC AACGACCTGG     350
AGAACCTCCG GGATCTTCTT CACGTGCTGG CCTTCTCTAA GAGCTGCCAC     400
TTGCCCTGGG CCAGTGGCCT GGAGACCTTG GACAGCCTGG GGGTGTCCT      450
GGAAGCTTCA GGCTACTCCA CAGAGGTGGT GGCCCTGAGC AGGCTGCAGG     500
GGTCTCTGCA GGACATGCTG TGGCAGCTGG ACCTCAGCCC TGGGTGCTGA     550
GGCCTTGAAG GTCACTCTTC CTGCAAGGAC T-ACGTTAAG GGAAGGAACT     600
CTGGTTTCCA GGTATCTCCA GGATTGAAGA GCATTGCATG GACACCCCTT     650
ATCCAGGACT CTGTCAATTT CCCTGACTCC TCTAAGCCAC TCTTCCAAAG     700
G                                                         701
```

FIG. 3

```
  1  Met His Trp Gly Thr Leu Cys Gly Phe Leu Trp Leu Trp Pro Tyr
 16  Leu Phe Tyr Val Gln Ala Val Pro Ile Gln Lys Val Gln Asp Asp
 31  Thr Lys Thr Leu Ile Lys Thr Ile Val Thr Arg Ile Asn Asp Ile
 46  Ser His Thr Gln Ser Val Ser Ser Lys Gln Lys Val Thr Gly Leu
 61  Asp Phe Ile Pro Gly Leu His Pro Ile Leu Thr Leu Ser Lys Met
 76  Asp Gln Thr Leu Ala Val Tyr Gln Gln Ile Leu Thr Ser Met Pro
 91  Ser Arg Asn Val Ile Gln Ile Ser Asn Asp Leu Glu Asn Leu Arg
106  Asp Leu Leu His Val Leu Ala Phe Ser Lys Ser Cys His Leu Pro
121  Trp Ala Ser Gly Leu Glu Thr Leu Asp Ser Leu Gly Gly Val Leu
136  Glu Ala Ser Gly Tyr Ser Thr Glu Val Val Ala Leu Ser Arg Leu
151  Gln Gly Ser Leu Gln Asp Met Leu Trp Gln Leu Asp Leu Ser Pro
166  Gly Cys End
```

```
Mouse  MCWRPLCRFL WLWSYLSYVQ AVPIQKVQDD TKTLIKTIVT RINDISHTQS   50
       * **       * *   *
Human  MHWGTLCGFL WLWPYLFYVQ AVPIQKVQDD TKTLIKTIVT RINDISHTQS Mouse  VSAKQRVTGL DFIPGLHPIL SLSKMDQTLA VYQQVLTSLP SQNVLQIAND  100
        *                                  -  -    *    *
Human  VSSKQKVTGL DFIPGLHPIL TLSKMDQTLA VYQQILTSMP SRNVIQISND Mouse  LENLRDLLHL LAFSKSCCSLP QTSGLQKPES LDGVLEASLY STEVVALSRL  150
                *     *       *-     *        *
Human  LENLRDLLHV LAFSKSCHLP WASGLETLDS LGGVLEASGY STEVVALSRL Mouse  QGSLQDILQQ LDVSPEC                                     167
          *    -  * *
Human  QGSLQDMLWQ LDLSPGC
```

```
1    Met Cys Trp Arg Pro Leu Cys Arg Phe Leu Trp Leu Trp Ser Tyr
16   Leu Ser Tyr Val Gln Ala Val Pro Ile Gln Lys Val Gln Asp Asp
31   Thr Lys Thr Leu Ile Lys Thr Ile Val Thr Arg Ile Asn Asp Ile
46   Ser His Thr Ser Val Ser Ala Lys Gln Arg Val Thr Gly Leu Asp
61   Phe Ile Pro Gly Leu His Pro Ile Leu Ser Leu Ser Lys Met Asp
76   Gln Thr Leu Ala Val Tyr Gln Gln Val Leu Thr Ser Leu Pro Ser
91   Gln Asn Val Leu Gln Ile Ala Asn Asp Leu Glu Asn Leu Arg Asp
106  Leu Leu His Leu Leu Ala Phe Ser Lys Ser Cys Ser Leu Pro Gln
121  Thr Ser Gly Leu Gln Lys Pro Glu Ser Leu Asp Gly Val Leu Glu
136  Ala Ser Leu Tyr Ser Thr Glu Val Val Ala Leu Ser Arg Leu Gln
151  Gly Ser Leu Gln Asp Ile Leu Gln Gln Leu Asp Val Ser Pro Glu
166  Cys End
```

FIG. 6

```
  1   MET HIS TRP GLY THR LEU CYS GLY PHE LEU TRP LEU TRP PRO TYR
 16   LEU PHE TYR VAL GLN ALA VAL PRO ILE GLN LYS VAL GLN ASP ASP
 31   THR LYS THR LEU ILE LYS THR ILE LYS THR VAL THR ARG ILE ASN ASP ILE
 46   SER HIS THR SER VAL SER SER LYS GLN LYS VAL THR GLY LEU ASP
 61   PHE ILE PRO GLY LEU HIS PRO ILE LEU THR LEU SER LYS MET ASP
 76   GLN THR LEU ALA VAL TYR GLN GLN ILE LEU THR SER MET PRO SER
 91   ARG ASN VAL ILE GLN ILE SER ASN ASP LEU GLU ASN LEU ARG ASP
106   LEU LEU HIS VAL LEU ALA PHE SER LYS SER CYS HIS LEU PRO TRP
121   ALA SER GLY LEU GLU THR LEU ASP SER LEU GLY GLY VAL LEU GLU
136   ALA SER GLY TYR SER THR GLU VAL VAL ALA LEU SER ARG LEU GLN
151   GLY SER LEU GLN ASP MET LEU TRP GLN LEU ASP LEU SER PRO GLY
166   CYS END
```

```
          +10        +20        +30        +40
GTGCAAGAAG AAGAAGATCC CAGGGCAGGA AAATGTGCTG GAGACCCCTG
---------- ---------- ----------→--------- ----------
CACGTTCTTC TTCTTCTAGG GTCCCGTCCT TTTACACGAC CTCTGGGAC

+10        +20        +30        +40
TGTCGGGTCC NGTGGNTTTG GTCCTATCTG TCTTATGTNC AAGCAGTGCC
-----?---- ----?----- ---------- -----?---- ---------GG
ACAGCCCAGG NCACCNAAAC CAGGATAGAC AGAATACANG TTCGTCACGG

+10        +20        +30        +40
TATCCAGAAA GTCCAGGATG ACACCAAAAG CCTCATCAAG ACCATTGTCA
---------- -----===== ========== ---------- ----------
ATAGGTCTTT CAGGTCCTAC TGTGGTTTTC GGAGTAGTTC TGGTAACAGT

+10        +20        +30        +40
NCAGGATCAC TGANATTTCA CACACG
?--------- ---?------ ------
NGTCCTAGTG ACTNTAAAGT GTGTGC
```

FIG. 10

2G7 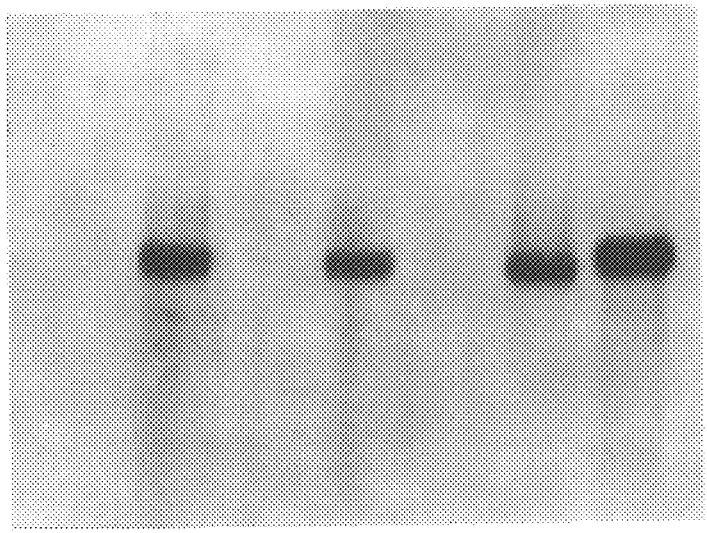
ap2 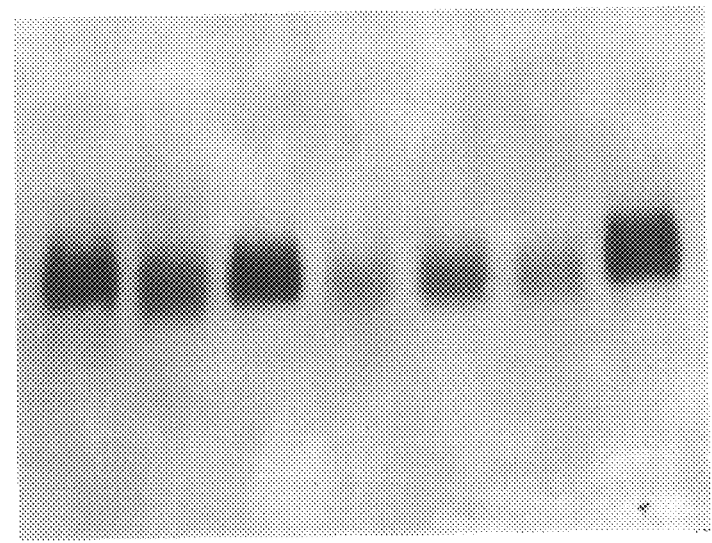
FIG. 13

```
T7 PROMOTER PRIMER 69348-1
- - - - - - - - - - - - ->
          T7 PROMOTER
- - - - - - - - - - - ->                            LAC OPERATOR        XbaI
BglII
AGATCTCGATCCCGCGAAATTAATACGACTCACTATAGGGGAATTGTGAGCGGATAACAATTCCCCTCTACA

RBS             NcoI                      His•Tag
AATAATTTTGTTTAACTTTAAGAAGGAGATATACCATGGGCAGCAGCCATCATCATCATCATCACAGCAGCGGC
                                     MetGlySerSerHisHisHisHisHisHisSerSerGly

NdeI    XhoI  BamHI
CTGGTGCCGCGCGGCAGCCATATGCTCGAGGATCCCGCTGCTAACAAAGCCCGAAAGGAAGCTGAGTTGGCT
LeuValProArgGlySerHisMetLeuGluAspProAlaAlaAsnLysAlaArgLysGluAlaGluLeuAla
THROMBIN

BpuI1021                                           T7 TERMINATOR
GCTGCCACCGCTGAGCAATAACTAGCATAACCCCTTGGGGCCTCTAAACGGGTCTTGAGGGGTTTTTG
AlaAlaThrAlaGluGlnEnd
       <- - - - - - - - - - -
       T7 TERMINATOR PRIMER #69337-1
```

FIG. 17

```
260        270        280        290        300
CCAGATAGTC CAAGAAACAT TTATTGAACG CCTCCTGAAT GCCAGGCACC 310        320        330        340        350
TACTGGAAGC TGAGAAGGAT TTTGGATAGC ACAGGGCTCC ACTCTTTCTG 360        370        380        390        400
GTTGTTTCTT NTGGCCCCCT CTGCCTGCTG AGATNCCAGG GGTTAGNGGT 410        420        430        440        450
TCTTAATTCC TAAA------ ---------- ---------- ------CT
              GAP OF SEQUENCE (~1.4 KB)

460        470        480        490        500
GGTTCTTTCA GGAAGAGGCC ATGTAAGAGA AAGGAATTGA CCTAGGGAAA
```

FIG. 20A-1

```
510              520              530              540              550
ATTGGCCTGG  GAAGTGGAGG  GAACGGATGG  TGTGGGAAAA  GCAGGAATCT
560              570              580              590              600
CGGAGACCAG  CTTAGAGGCT  TGGCAGTCAC  CTGGGTGCAG  GANACAAGGG
610              620              630              640              650
CCTGAGCCAA  AGTGGTGAGG  GAGGGTGGAA  GGAGACAGCC  CAGAGAATGA
660              670              680              690              700
CCCTCCCATGC  CCACGGGGAA  GGCAGAGGGC  TCTGAGAGCG  ATTCCTCCCA
                                                  3' OF 1ST INTRON ←┐
710              720              730              740              750
CATGCTGAGC  ACTTGTCTC   CCTCTTCCTC  CTNCATAGCA  GTCAGTCTCC
         →
HOB 2g F
```

```
760         770         780         790         800
TCCAAACAGA  AAGTCACCGG  TTTGGACTTC  ATTCCTGGGC  TCCACCCCAT
810         820         830         840         850
CCTGACCTTA  TCCAAGATGG  ACCAGACACT  GGCAGTCTAC  CAACAGATCC
860         870         880         890         900
TCACCAGTAT  GCCTTCCAGA  AACGTGATCC  AAATATCCAA  CGACCTGGAG
910         920         930         940         950
AACCTCCGGG  ATCTTCTTCA  CGTGCTGGCC  TTCTCTAAGA  GCTGCCACTT
960         970         980         990         1000
GCCCTGGGCC  AGTGGCCCTG  AGACCTTGGA  CAGCCTGGGG  GGTGTCCTGG
```

```
    1010         1020        1030         1040         1050
AAGCTTCAGG CTACTCCACA GAGGTGGTGG CCCTGAGCAG GCTGCAGGGG
    1060         1070        1080         1090         1100
TCTCTGCAGG ACATGCTGTG GCAGCTGGAC CTCAGCCCTG GGTGCTGAGG
                                                    STOP
    1110         1120        1130         1140         1150
CCTTGAAGGT CACTCTTCCT GCAAGGACTA CGTTAAGGGA AGGAACTCTG
    1160         1170        1180         1190         1200
GCTTTCCAGG TATCTCCAGG ATTGAAGAGC ATTGCATGGA CACCCCTTAT
       ────────►
       HOB 2G R
    1210         1220        1230         1240      1249
CCAGGACTCT GTCAATTTCC CTGACTCCTC TAAGCCACTC TTCCAAAGG
```

FIG. 20A-4

MOUSE OB STRUCTURE

HUMAN OB STRUCTURE

MAMMALIAN OB POLYPEPTIDES CAPABLE OF MODULATING BODY WEIGHT, CORRESPONDING NUCLEIC ACIDS, AND DIAGNOSTIC AND THERAPEUTIC USES THEREOF

RELATED APPLICATIONS

The present application is a continuation-in-part of copending application Ser. No. 08/292,345, filed Aug. 17, 1994, of which the instant application claims the benefit of the filing date pursuant to 35 U.S.C. § 120, and which is incorporated herein by reference in its entirety.

The research leading to the present inventions was funded in part by Grant No. DK 41096 from the National Institutes of Health. The government may have certain rights in the invention.

TECHNICAL FIELD OF THE INVENTION

The present invention relates generally to the control of body weight of mammals including animals and humans, and more particularly to materials identified herein as modulators of weight, and to the diagnostic and therapeutic uses to which such modulators may be put.

BACKGROUND OF THE INVENTION

Obesity, defined as an excess of body fat relative to lean body mass, is associated with important psychological and medical morbidities, the latter including hypertension, elevated blood lipids, and Type II or non-insulin-dependent diabetes melitis (NIDDM). There are 6–10 million individuals with NIDDM in the U.S., including 18% of the population of 65 years of age (Harris et al., 1987). Approximately 45% of males and 70% of females with NIDDM are obese, and their diabetes is substantially improved or eliminated by weight reduction (Harris, 1991). As described below, both obesity and NIDDM are strongly heritable, though the predisposing genes have not been identified. The molecular genetic basis of these metabolically related disorders is an important, poorly understood problem.

The assimilation, storage, and utilization of nutrient energy constitute a complex homeostatic system central to survival of metazoa. Among land-dwelling mammals, storage in adipose tissue of large quantities of metabolic fuel as triglycerides is crucial for surviving periods of food deprivation. The need to maintain a fixed level of energy stores without continual alterations in the size and shape of the organism requires the achievement of a balance between energy intake and expenditure. However, the molecular mechanisms that regulate energy balance remain to be elucidated. The isolation of molecules that transduce nutritional information and control energy balance will be critical to an understanding of the regulation of body weight in health and disease.

An individual's level of adiposity is, to a large extent, genetically determined. Examination of the concordance rates of body weight and adiposity amongst mono- and dizygous twins or adoptees and their biological parents have suggested that the heritability of obesity (0.4–0.8) exceeds that of many other traits commonly thought to have a substantial genetic component, such as schizophrenia, alcoholism, and atherosclerosis (Stunkard et al., 1990). Familial similarities in rates of energy expenditure have also been reported (Bogardus et al., 1986). Genetic analysis in geographically delimited populations has suggested that a relatively small number of genes may account for the 30%–50% of variance in body composition (Moll et al., 1991). However, none of the genes responsible for obesity in the general population have been genetically mapped to a definite chromosomal location.

Rodent models of obesity include seven apparently single-gene mutations. The most intensively studied mouse obesity mutations are the ob (obese) and db (diabetes) genes. When present on the same genetic strain background, ob and db result in indistinguishable metabolic and behavioral phenotypes, suggesting that these genes may function in the same physiologic pathway (Coleman, 1978). Mice homozygous for either mutation are hyperphagic and hypometabolic, leading to an obese phenotype that is notable at one month of age. The weight of these animals tends to stabilize at 60–70 g (compared with 30–35 g in control mice). ob and db animals manifest a myriad of other hormonal and metabolic changes that have made it difficult to identify the primary defect attributable to the mutation (Bray et al., 1989).

Each of the rodent obesity models is accompanied by alterations in carbohydrate metabolism resembling those in Type II diabetes in man. In some cases, the severity of the diabetes depends in part on the background mouse strain (Leiter, 1989). For both ob and db, congenic C57BL/Ks mice develop a severe diabetes with ultimate , β cell necrosis and islet atrophy, resulting in a relative insulinopenia. Conversely, congenic C57BL/6J ob and db mice develop a transient insulin-resistant diabetes that is eventually compensated by β cell hypertrophy resembling human Type II diabetes.

The phenotype of ob and db mice resembles human obesity in ways other than the development of diabetes—the mutant mice eat more and expend less energy than do lean controls (as do obese humans). This phenotype is also quite similar to that seen in animals with lesions of the ventromedial hypothalamus, which suggests that both mutations may interfere with the ability to properly integrate or respond to nutritional information within the central nervous system. Support for this hypothesis comes from the results of parabiosis experiments (Coleman, 1973) that suggest ob mice are deficient in a circulating satiety factor and that db mice are resistant to the effects of the ob factor (possibly due to an ob receptor defect). These experiments have led to the conclusion that obesity in these mutant mice may result from different defects in an afferent loop and/or integrative center of the postulated feedback mechanism that controls body composition.

Using molecular and classical genetic markers, the ob and db genes have been mapped to proximal chromosome 6 and midchromosome 4, respectively (Bahary et al., 1990; Friedman et al., 1991b). In both cases, the mutations map to regions of the mouse genome that are syntonic with human, suggesting that, if there are human homologs of ob and db, they are likely to map, respectively, to human chromosomes 7q and 1p. Defects in the db gene may result in obesity in other mammalian species: in genetic crosses between Zucker falfa rats and Brown Norway +/+rats, the fa mutation (rat chromosome 5) is flanked by the same loci that flank db in mouse (Truett et al., 1991).

Because of the myriad factors that seem to impact body weight, it is difficult to speculate as to which of these factors, and more particularly, which homeostatic mechanism is actually primarily determinative. Nonetheless, the apparent connection between the ob gene and the extent and characteristics of obesity have prompted the further investigation and elucidation that is reflected by the present application. It is the identification of the sequence of the gene and corresponding peptide materials, to which the present invention following below directs itself.

The citation of any reference herein should not be construed as an admission that such reference is prior art to the instant invention. Full citations of references cited by author and year are found at the end of the specification.

SUMMARY OF THE INVENTION

In its broadest aspect, the present invention relates to the elucidation and discovery of nucleotide sequences, and proteins putatively expressed by such nucleic acids or degenerate variations thereof, that demonstrate the ability to participate in the control of mammalian body weight. The nucleotide sequences in object are believed to represent the genes corresponding to the murine and human ob gene, that is postulated to play a critical role in the regulation of body weight and adiposity. Data presented herein indicates that the polypeptide product of the gene in question is secreted by the cells that express it and that the polypeptide functions as a hormone.

In a first instance, the modulators of the present invention comprise nucleic acid molecules, including recombinant DNA molecules (e.g., cDNA or a vector containing the cDNA or isolated genomic DNA) or cloned genes (i.e. isolated genomic DNA), or degenerate variants thereof, which encode polypeptides themselves serving as modulators of weight control as hereinafter defined, or conserved variants or fragments thereof, particularly such fragments lacking the signal peptide (alternatively referred to herein as mature ob polypeptide), which polypeptides possess amino acid sequences such as set forth in FIG. 1 (SEQ ID NO:2), FIG. 3 (SEQ ID NO:4), FIG. 5 (SEQ ID NO:5) and FIG. 6 (SEQ ID NO:6). In specific embodiments, amino acid sequences for two variants of murine and human ob polypeptides are provided. Both polypeptides are found in a form with glutamine 49 deleted, which may result from an mRNA splicing anomaly. The ob polypeptides from various species may be highly homologous; as shown in FIG. 4, murine and human ob polypeptides are greater than 80% homologous.

The nucleic acid molecules, recombinant DNA molecules, or cloned genes, may have the nucleotide sequences or may be complementary to DNA coding sequences shown in FIG. 1 (SEQ ID NO:1) and FIG. 2 (SEQ ID NO:3). In particular, such DNA molecules can be cDNA or genomic DNA isolated from the chromosome. Nucleic acid molecules of the invention may also correspond to 5' and 3' flanking sequences of the DNA. Accordingly, the present invention also relates to the identification of a gene having a nucleotide sequence selected from the sequences of FIG. 1 (SEQ ID NO:1) and FIG. 2 (SEQ ID NO:3) herein, and degenerate variants, allelic variations, and like cognate molecules.

A nucleic acid molecule of the invention can be DNA or RNA, including synthetic variants thereof having phosphate or phosphate analog, e.g., thiophosphate, bonds. Both single stranded and double stranded sequences are contemplated herein.

The present invention further provides nucleic acid molecules for use as molecular probes, or as primers for polymerase chain reaction (PCR) amplification, i.e., synthetic or natural oligonucleotides having a sequence corresponding to a portion of the sequences shown in FIG. 1 (SEQ ID NO:1), FIG. 2 (SEQ ID NO:3) and FIG. 20A (SEQ ID NO:22), or the 5' and 3' flanking sequences of the coding sequences. In particular, the invention contemplates a nucleic acid molecule having at least about 10 nucleotides, wherein a sequence of the nucleic acid molecule corresponds to a nucleotide sequence of the same number of nucleotides in the nucleotide sequences of FIG. 1 (SEQ ID NO:1), FIG. 2 (SEQ ID NO:3) and FIG. 20A (SEQ ID NO:22), or a sequence complementary thereto. More preferably, the nucleic acid sequence of the molecule has at least 15 nucleotides. Most preferably, the nucleic acid sequence has at least 20 nucleotides. In an embodiment of the invention in which the oligonucleotide is a probe, the oligonucleotide is detectably labeled, e.g., with a radionuclide (such as $^{32}P$), or an enzyme.

In further aspects, the present invention provides a cloning vector, which comprises the nucleic acids of the invention that encode the ob polypeptide; and a bacterial, insect, or a mammalian expression vector, which comprises the nucleic acid molecules of the invention encoding the ob polypeptide, operatively associated with an expression control sequence. Accordingly, the invention further relates to a host cell, such as a bacterial cell, yeast cell, insect cell, or a mammalian cell, transfected or transformed with an appropriate expression vector, and correspondingly, to the use of the above mentioned constructs in the preparation of the modulators of the invention.

In yet a further aspect, the present invention relates to antibodies that bind to the ob polypeptide. Such antibodies may be generated against the full length polypeptide, or antigenic fragments thereof. In one aspect, such antibodies inhibit the functional (i.e., body weight and fat composition modulating) activity of the ob polypeptide.

All of the foregoing materials are to be considered herein as modulators of body weight and fat composition, and as such, may be used in a variety of contexts. Specifically, the invention contemplates both diagnostic and therapeutic applications, as well as certain agricultural applications, all contingent upon the use of the modulators defined herein, including both nucleic acid molecules and peptides. Moreover, the modulation of body weight carries specific therapeutic implications and benefits, in that conditions where either obesity or, conversely, cachexia represent undesired bodily conditions, can be remedied by the administration of one or more of the modulators of the present invention.

Thus, a method for modulating body weight of a mammal is proposed that comprises controlling the expression of the protein encoded by a nucleic acid having nucleotide sequence selected from the sequence of FIG. 1 (SEQ ID NO:1), the sequence of FIG. 2 (SEQ ID NO:3) and degenerate and allelic variants thereof. Such control may be effected by the introduction of the nucleotides in question by gene therapy into fat cells of the patient or host to control or reduce obesity. Conversely, the preparation and administration of antagonists to the nucleotides, such as anti-sense molecules, would be indicated and pursued in the instance where conditions involving excessive weight loss, such as anorexia nervosa, cancer, or AIDS are present and under treatment. Such constructs would be introduced in similar fashion to the nucleotides, directly into fat cells to effect such changes.

Correspondingly, the proteins defined by FIGS. 1, 3, 5, and 6 (SEQ ID NO:1, SEQ ID NO:4, SEQ ID NO:5, and SEQ ID NO:6), conserved variants, active fragments thereof, and cognate small molecules could be formulated for direct administration for therapeutic purposes, to effect reduction or control of excessive body fat or weight gain.

Correspondingly, antibodies and other antagonists to the stated protein materials, such as fragments thereof, could be prepared and similarly administered to achieve the converse effect. Accordingly, the invention is advantageously directed to a pharmaceutical composition comprising an ob polypeptide of the invention, or alternatively an antagonist thereof, in an admixture with a pharmaceutically acceptable carrier or excipient.

The diagnostic uses of the present nucleotides and corresponding peptides extend to the use of the nucleotides to identify further mutations of allelic variations thereof, so as to develop a repertoire of active nucleotide materials useful in both diagnostic and therapeutic applications. In particular, both homozygous and heterozygous mutations of the nucleotides in question could be prepared that would be postulated to more precisely quantitate the condition of patients, to determine the at-risk potential of individuals with regard to obesity. Specifically, heterozygous mutations are presently viewed as associated with mild to moderate obesity, while homozygous mutations would be associated with a more pronounced and severe obese condition. Corresponding DNA testing could then be conducted utilizing the aforementioned ascertained materials as benchmarks, to facilitate an accurate long term prognosis for particular tendencies, so as to be able to prescribe changes in either dietary or other personal habits, or direct therapeutic intervention, to avert such conditions.

The diagnostic utility of the present invention extends to methods for measuring the presence and extent of the modulators of the invention in cellular samples or biological extracts (or samples) taken from test subjects, so that both the encoded nucleotide (genomic DNA or RNA) and or the levels of protein in such test samples could be ascertained. Given that the increased activity of the nucleotide and presence of the resulting protein reflect the capability of the subject to inhibit obesity, the physician reviewing such results in an obese subject would determine that a factor other than dysfunction with respect to the presence and activity of the nucleotides of the present invention is a cause of the obese condition. Conversely, depressed levels of the nucleotide and or the expressed protein would suggest that such levels must be increased to treat such obese condition, and an appropriate therapeutic regimen could then be implemented.

Further, the nucleotides discovered and presented in FIGS. 1 and 2 represent cDNA in which, as stated briefly above, is useful in the measurement of corresponding RNA. Likewise, recombinant protein material corresponding to the polypeptides of FIGS. 1 and 3 may be prepared and appropriately labeled, for use, for example, in radioimmunoassays, for example, for the purpose of measuring fat and/or plasma levels of the ob protein, or for detecting the presence and level of a receptor for ob on tissues, such as the hypothalamus.

Yet further, the present invention contemplates not only the identification of the nucleotides and corresponding proteins presented herein, but the elucidation of the receptor to such materials. In such context, the polypeptides of FIGS. 1, 3, 5, and/or 6 could be prepared and utilized to screen an appropriate expression library to isolate active receptors. The receptor could thereafter be cloned, and the receptor alone or in conjunction with the ligand could thereafter be utilized to screen for small molecules that may possess like activity to the modulators herein.

Yet further, the present invention relates to pharmaceutical compositions that include certain of the modulators hereof, preferably the polypeptides whose sequences are presented in SEQ ID NO:2, SEQ ID NO:4, SEQ ID NO:5 and SEQ ID NO:6, their antibodies, corresponding small molecule agonists or antagonists thereof, or active fragments prepared in formulations for a variety of modes of administration, where such therapy is appropriate. Such formulations would include pharmaceutically acceptable carriers, or other adjuvants as needed, and would be prepared in effective dosage ranges to be determined by the clinician or the physician in each instance.

Accordingly, it is a principal object of the present invention to provide modulators of body weight as defined herein in purified form, that exhibit certain characteristics and activities associated with control and variation of adiposity and fat content of mammals.

It is a further object of the present invention to provide methods for the detection and measurement of the modulators of weight control as set forth herein, as a means of the effective diagnosis and monitoring of pathological conditions wherein the variation in level of such modulators is or may be a characterizing feature.

It is a still further object of the present invention to provide a method and associated assay system for the screening of substances, such as drugs, agents and the like, that are potentially effective to either mimic or inhibit the activity of the modulators of the invention in mammals.

It is a still further object of the present invention to provide a method for the treatment of mammals to control body weight and fat content in mammals, and or to treat certain of the pathological conditions of which abnormal depression or elevation of body weight is a characterizing feature.

It is a still further object of the present invention to prepare genetic constructs for use in genetic therapeutic protocols and or pharmaceutical compositions for comparable therapeutic methods, which comprise or are based upon one or more of the modulators, binding partners, or agents that may control their production, or that may mimic or antagonize their activities.

Other objects and advantages will become apparent to those skilled in the art from a review of the ensuing description which proceeds with reference to the following illustrative drawings.

BRIEF DESCRIPTION OF THE DRAWINGS

FIG. 1 depicts the nucleic acid sequence (SEQ ID NO:1) and deduced amino acid sequence (SEQ ID NO:2) derived for the murine ob cDNA. A 97 base pair 5' leader was followed by a predicted 167 amino acid open reading frame and an approximately 3700 kB 3' untranslated sequence. A total of about 2500 base pairs of the 3' unstranslated sequence is shown. Analysis of the predicted protein sequence by observation and using the SigSeq computer program indicates the presence of a signal sequence (underlined). Microheterogeneity of the cDNA was noted in that approximately 70% of the cDNAs had a glutamine codon at codon 49 and 30% did not (see FIGS. 5 and 6, infra). This amino acid is underlined, as is the arginine codon that is mutated in C57BL/6J ob/ob mice (1J mice).

FIG. 2 depicts the nucleic acid sequence (SEQ ID NO:3) derived for the human ob cDNA. The nucleotides are numbered from 1 to 701 with a start site at nucleotide 46 and a termination at nucleotide 550.

FIG. 3 depicts the full deduced amino acid sequence (SEQ ID NO:4) derived for the human ob gene corresponding to the nucleic acid sequence of FIG. 2. The amino acids are numbered from 1 to 167. A signal sequence cleavage site is located after amino acid 21 (Ala) so that the mature protein extends from amino acid 22 (Val) to amino acid 167 (Cys).

FIG. 4 depicts the comparison between the murine (SEQ ID NO:2) and human (SEQ ID NO:4) deduced amino acid sequences. The sequence of the human ob deduced amino acid sequence was highly homologous to that of mouse. Conservative changes are noted by a dash, and non-conservative changes by an asterisk. The variable glutamine codon is underlined, as is the position of the nonsense mutation in C57BL/6J ob/ob (1J) mice. Overall, there is 83% identity at the amino acid level, although only six substitutions were found between the valine at codon 22 (immediately downstream of the signal sequence overage) and the cysteine at position 117.

FIG. 5 depicts the full length amino acid sequence (SEQ ID NO:5) derived for the murine ob gene as shown in FIG. 3, but lacking glutamine at position 49. The nucleotides are numbered from 1 to 166. A signal sequence cleavage site is located after amino acid 21 (Ala) (and thus, before the glutamine 49 deletion) so that the mature protein extends from amino acid 22 (Val) to amino acid 166 (Cys).

FIG. 6 depicts the full deduced amino acid sequence (SEQ ID NO:6) derived for the human ob gene as shown in FIG. 4, but lacking glutamine at position 49. The nucleotides are numbered from 1 to 166. A signal sequence cleavage site is located after amino acid 21 (Ala) (and thus, before the glutamine 49 deletion) so that the mature protein extends from amino acid 22 (Val) to amino acid 166 (Cys).

FIG. 10 presents the sequence of the 2G7 clone (SEQ ID NO:7), which includes an exon coding for a part of the ob gene. The primer sequences used to amplify this exon are boxed in the figure (SEQ ID NOS:8 and 9).

FIG. 13 is a Northern analysis of additional 2J animals and control animals that confirms the absence of the ob mRNA from 2J animals. The Northern analysis was performed as in FIGS. 11 and 12. In this case, the control RNA was ap2, a fat specific transcript. There is no significance to the varying density of the ap2 bands.

FIG. 17 presents the expression cloning region of vector pET-15b (Novagen).

DETAILED DESCRIPTION

Figure 7:
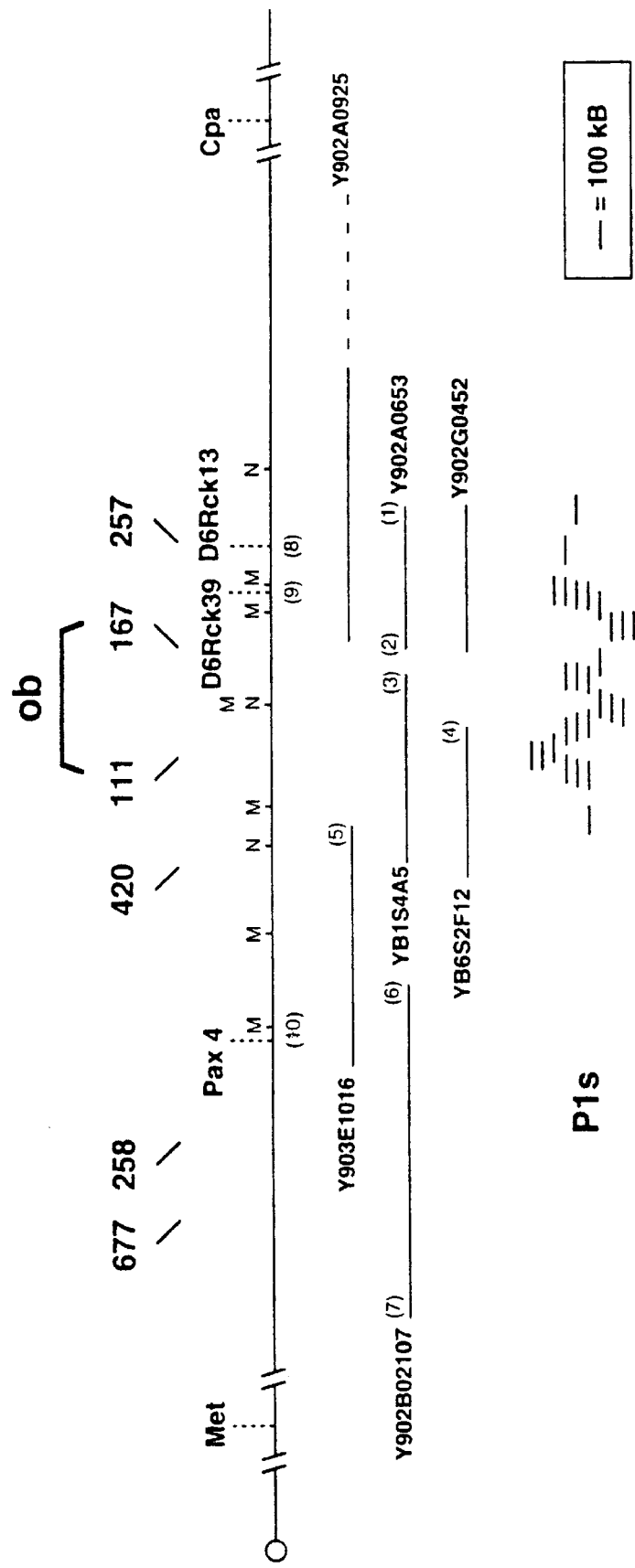
FIG. 7. (A) Physical map of the location of ob in the murine chromosome, and the YAC and P1 cloning maps. "M and N" corresponds to MulI and NotI restriction sites. The numbers correspond to individual animals that were recombinant in the region of ob of the 1606 meioses that were scored. Met, Pax 4, D6Rck39, D6Rck13, and Cpa refer to locations in the region of ob that bind to the DNA probes. YACs were isolated using D6Rck13 and Pax-4 as probes, and the ends were recovered using vectorette PCR and/or plasmid end rescue and used in turn to isolate new YACs. (B) The resulting YAC contig. One of the YACs in this contig, Y902A0925, was chimeric. Each of the probes used to genotype the recombinant animals is indicated in parentheses. (6) Corresponds to YAC 107; (5) corresponds to M16(+) (or M16(pLUS)); (4) corresponds to adu(+); (3) corresponds to aad(pICL); (2) corresponds to 53(pICL); and (1) corresponds to 53(+). (C) The P1 contig of bacteriophage P1 clones isolated with selected YAC end probes. The ob gene was isolated in a P1 clone isolated using the distal end of YAC YB6S2F12 (end (4)) (alternatively termed herein adu(+)).
Figure 8:
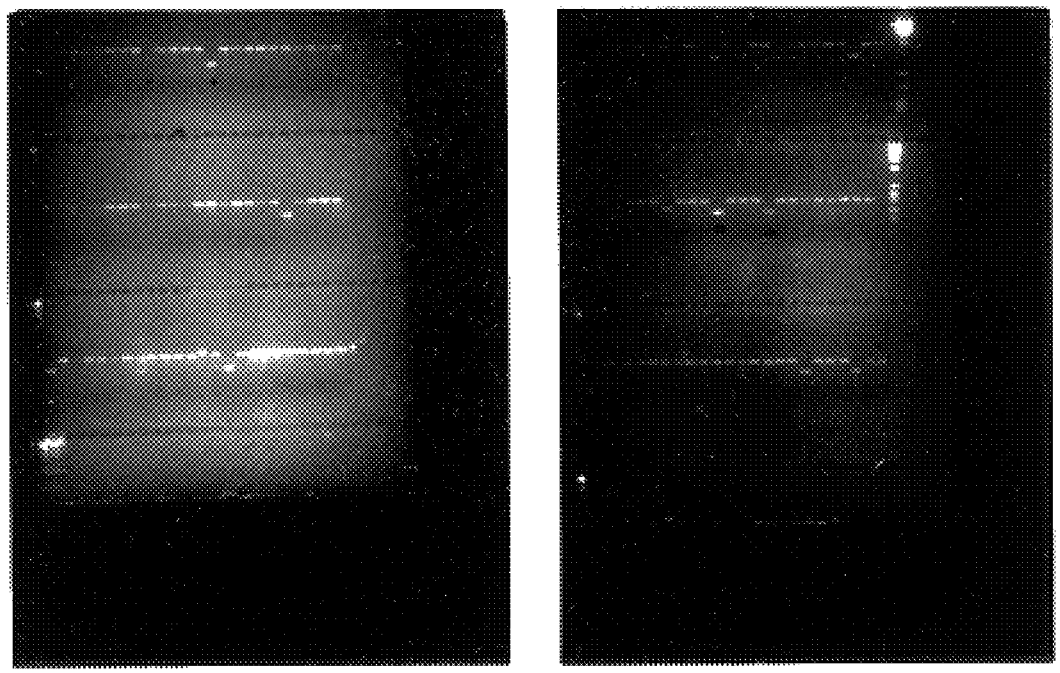
FIG. 8 presents a photograph of an ethidium bromide stain of 192 independent isolates of the fourth exon trapping experiment that were PCR amplified and characterized.
Figure 9:
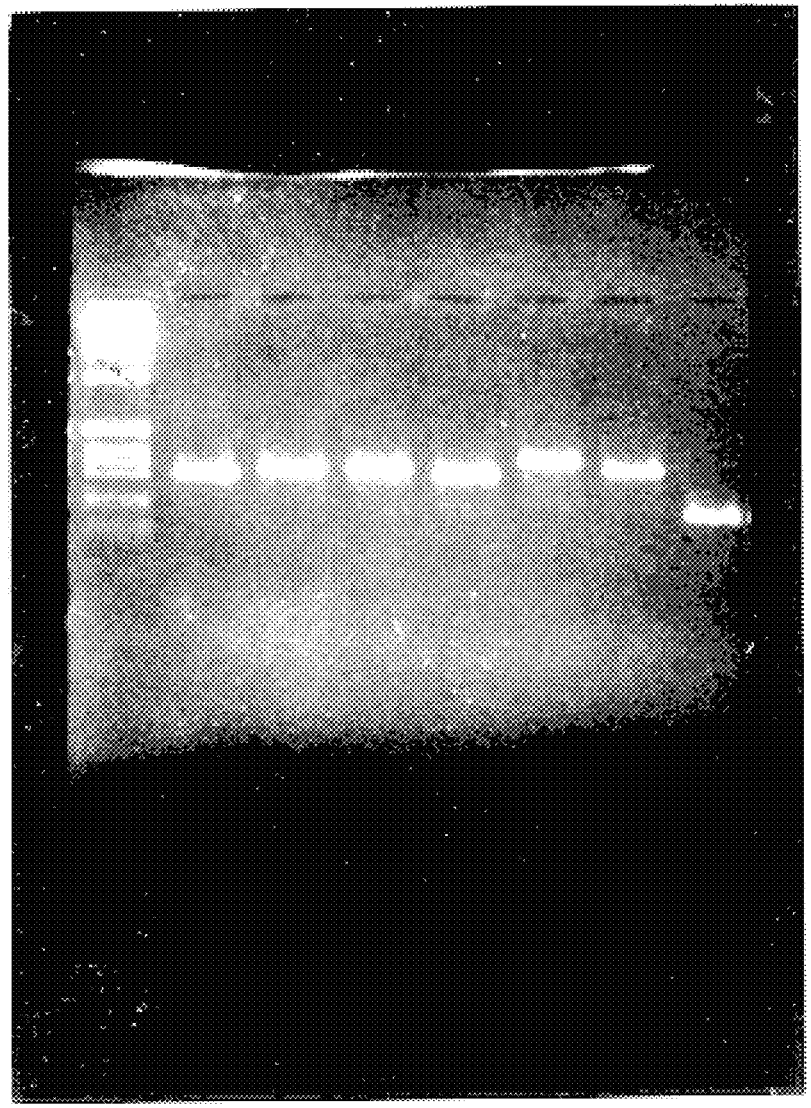
FIG. 9 is a photograph of an ethidium bromide stain of PCR-amplified clones suspected of carrying ob. Each of the 7 clones that did not carry the artifact was reamplified using PCR and electrophoresed on a 1% agarose gel in TBE and stained with ethidium bromide. The size markers (far left unnumbered lane) are the commercially available "1 kB ladder". Lane 1—clone 1D12, containing an "HIV sequence." Lane 2—clone 1F1, a novel clone outside of the ob region. Lane 3—clone 1H3. Lane 4—clone 2B2, which is the identical to 1F1. Lane 5—clone 2G7, which contains an ob exon. Lane 6—clone 2G11, which is identical to 1F1. Lane 7—clone 2H1, which does not contain an insert.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984). Of particular relevance to the present invention are strategies for isolating, cloning, sequencing, analyzing, and characterizing a gene or nucleic acid based on the well known polymerase chain reaction (PCR) techniques.

Therefore, if appearing herein, the following terms shall have the definitions set out below.

The term "body weight modulator", "modulator", "modulators", and any variants not specifically listed, may be used herein interchangeably, and as used throughout the present application and claims refers in one instance to both nucleotides and to proteinaceous material, the latter including both single or multiple proteins. More specifically, the aforementioned terms extend to the nucleotides and to the DNA having the sequences described herein and presented in FIG. 1 (SEQ ID NO:1), and FIG. 2 (SEQ ID NO:3). Likewise, the proteins having the amino acid sequence data described herein and presented in FIG. 1 (SEQ ID NO:2), and FIG. 3 (SEQ ID NO:4) are likewise contemplated, as are the profile of activities set forth with respect to all materials both herein and in the claims. Accordingly, nucleotides displaying substantially equivalent or altered activity are likewise contemplated, including substantially homologous analogs and allelic variations. Likewise, proteins displaying substantially equivalent or altered activity, including proteins modified deliberately, as for example, by site-directed mutagenesis, or accidentally through mutations in hosts that produce the modulators are likewise contemplated.

The terms "protein," which refers to the naturally occurring polypeptide, and "polypeptide" are used herein interchangeably with respect to the ob gene product and variants thereof. The term "mature protein" or "mature polypeptide" refers to the ob gene product with the signal sequence (or a fusion protein partner) removed.

A "replicon" is any genetic element (e.g., plasmid, chromosome, virus) that functions as an autonomous unit of DNA replication in vivo, i.e., capable of replication under its own control.

A "vector" is a replicon, such as a plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

"Heterologous" DNA refers to DNA not naturally located in the cell, or in a chromosomal site of the cell. Preferably, the heterologous DNA includes a gene foreign to the cell.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50 % formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is also used herein to refer to this sort of signal sequence. Translocation signal sequences can be found associated with a variety of proteins native to eukaryotes and prokaryotes, and are often functional in both types of organisms.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The term "standard hybridization conditions" refers to salt and temperature conditions substantially equivalent to 5× SSC and 65° C. for both hybridization and wash.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, $F(ab')_2$ and Fr (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also wellknown and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A composition comprising "A" (where "A" is a single protein, DNA molecule, vector, recombinant host cell, etc.) is substantially free of "B" (where "B" comprises one or more contaminating proteins, DNA molecules, vectors, etc., but excluding racemic forms of A) when at least about 75% by weight of the proteins, DNA, vectors (depending on the category of species to which A and B belong) in the composition is "A". Preferably, "A" comprises at least about 90% by weight of the A+B species in the composition, most preferably at least about 99 % by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guenin*) and *Corynebacterium parvum*. Preferably, the adjuvant is pharmaceutically acceptable.

In its primary aspect, the present invention is directed to the identification of materials that function as modulators of mammalian body weight. In particular, the invention concerns the isolation, purification and sequencing of certain nucleic acids that correspond to the ob gene in both mice and humans, as well as the corresponding polypeptides expressed by these nucleic acids. The invention thus comprises the discovery of nucleic acids having the nucleotide sequences set forth in FIG. 1 (SEQ ID NO:1) and FIG. 2 (SEQ ID NO:3), and to degenerate variants, alleles and fragments thereof, all possessing the activity of modulating body weight and adiposity. The correspondence of the present nucleic acids to the ob gene portends their significant impact on conditions such as obesity as well as other maladies and dysfunctions where abnormalities in body weight are a contributory factor. The invention extends to the proteins expressed by the nucleic acids of the invention, and particularly to those proteins set forth in FIG. 1 (SEQ ID NO:2), FIG. 3 (SEQ ID NO:4), FIG. 5 (SEQ ID NO:5), and FIG. 6 (SEQ ID NO:6), as well as conserved variants, active fragments, and cognate small molecules.

In particular, the present invention contemplates that naturally occurring fragments of the ob polypeptide may be important. The peptide sequence includes a number of sites that are frequently the target for proteolytic cleavage, e.g., arginine residues. It is possible that the full length polypeptide may be cleaved at one or more such sites to form biologically active fragments. Such biologically active fragments may either agonize or antagonize the functional activity of the ob polypeptide to reduce body weight.

As discussed earlier, the weight control modulator peptides or their binding partners or other ligands or agents exhibiting either mimicry or antagonism to them or control over their production, may be prepared in pharmaceutical compositions, with a suitable carrier and at a strength effective for administration by various means to a patient experiencing abnormal fluctuations in body weight or adiposity, either alone or as part of an adverse medical condition such as cancer or AIDS, for the treatment thereof.

A variety of administrative techniques may be utilized, among them parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

Also, antibodies including both polyclonal and monoclonal antibodies, and drugs that modulate the production or activity of the weight control modulators recognition factors and/or their subunits may possess certain diagnostic applications and may for example, be utilized for the purpose of detecting and/or measuring conditions where abnormalities in body weight are or may be likely to develop. For example, the modulator peptides or their active fragments may be used to produce both polyclonal and monoclonal antibodies to themselves in a variety of cellular media, by known techniques such as the hybridoma technique utilizing, for example, fused mouse spleen lymphocytes and myeloma cells. These techniques are described in detail below. Likewise, small molecules that mimic or antagonize the activity(ies) of the receptor recognition factors of the invention may be discovered or synthesized, and may be used in diagnostic and/or therapeutic protocols.

Panels of monoclonal antibodies produced against modulator peptides can be screened for various properties; i.e., isotype, epitope, affinity, etc. Of particular interest are monoclonal antibodies that neutralize the activity of the modulator peptides. Such monoclonals can be readily identified in activity assays for the weight modulators. High affinity antibodies are also useful when immunoaffinity purification of native or recombinant modulator is possible.

Preferably, the anti-modulator antibody used in the diagnostic and therapeutic methods of this invention is an affinity purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

As suggested earlier, a diagnostic method useful in the present invention comprises examining a cellular sample or medium by means of an assay including an effective amount of an antagonist to a modulator protein, such as an anti-modulator antibody, preferably an affinity-purified polyclonal antibody, and more preferably a mAb. In addition, it is preferable for the anti-modulator antibody molecules used herein be in the form of Fab, Fab', F(ab')$_2$ or F(v) portions or whole antibody molecules. As previously discussed, patients capable of benefiting from this method include those suffering from cancer, AIDS, obesity or other condition where abnormal body weight is a characteristic or factor. Methods for isolating the modulator and inducing anti-modulator antibodies and for determining and optimizing the ability of anti-modulator antibodies to assist in the examination of the target cells are all well-known in the art.

The nucleic acids contemplated by the present invention extend as indicated, to other nucleic acids that code on expression for peptides such as those set forth in FIG. 1 (SEQ ID NO:2), FIG. 3 (SEQ ID NO:4), FIG. 5 (SEQ ID NO:5), and FIG. 6 (SEQ ID NO:6) herein. Accordingly, while specific DNA has been isolated and sequenced in relation to the ob gene, any animal cell potentially can serve as the nucleic acid source for the molecular cloning of a gene encoding the peptides of the invention. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U. K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, the genomic DNA can be amplified using primers selected from the cDNA sequences. Alternatively, DNA fragments are generated, some of which will encode the desired gene. The DNA may be cleaved at specific sites using various restriction enzymes. One may also use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired ob or ob-like gene may be accomplished in a number of ways. For example, if an amount of a portion of a ob or ob-like gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in FIG. 1 (SEQ ID NO:1) or FIG. 2 (SEQ ID NO:3). Preferably, a fragment is selected that is highly unique to the modulator peptides of the invention. Those DNA fragments with substantial homology to the probe will hybridize. As noted above, the greater the degree of homology, the more stringent hybridization conditions can be used. In one embodiment, low stringency hybridization conditions are used to identify a homologous modulator peptide. However, in a preferred aspect, and as demonstrated experimentally herein, a nucleic acid encoding a modulator peptide of the invention will hybridize to a nucleic acid having a nucleotide sequence such as depicted in FIG. 1 (SEQ ID NO:1) or FIG. 2 (SEQ ID NO:3), or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, tyrosine phosphatase activity or antigenic properties as known for the present modulator peptides. For example, the antibodies of the instant invention can conveniently be used to screen for homologs of modulator peptides from other sources.

A gene encoding a modulator peptide of the invention can also be identified by mRNA selection, i.e., by nucleic acid hybridization followed by in vitro translation. In this procedure, fragments are used to isolate complementary mRNAs by hybridization. Such DNA fragments may represent available, purified modulator DNA. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a modulator peptide.

A radiolabeled modulator peptide cDNA can be synthesized using the selected mRNA (from the adsorbed polysomes) as a template. The radiolabeled mRNA or cDNA may then be used as a probe to identify homologous modulator peptide DNA fragments from among other genomic DNA fragments.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9, pUC or pUC plasmid derivatives, e.g., pGEX vectors, pET vectors, pmal-c, pFLAG, etc., and their derivatives, plasmids such as RP4; phage DNAs, e.g., the numerous derivatives of phage λ, e.g., NM989, and other phage DNA, e.g., M13 and Filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In a preferred embodiment, expression of ob is achieved in methylotrophic yeast, e.g., Pichia pastoris yeast (see, e.g., International Pat. Publication No. WO 90/03431, published Apr. 5, 1990, by Brierley et al.; International Pat. Publication No. WO 90/10697, published Sep. 20, 1990, by Siegel et al.). In a specific embodiment, infra, an expression vector is engineered for expression of ob under control of the α-mating factor signal sequence.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the AOX 1 promoter of methylotrophic yeast, the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces; fungi such as yeasts (Saccharomyces, and methylotrophic yeast such as Pichia, Candida, Hansenula, and Torulopsis); and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

In a specific embodiment, an ob fusion protein can be expressed. An ob fusion protein comprises at least a functionally active portion of a non-ob protein joined via a peptide bond to at least a functionally active portion of an ob polypeptide. The non-ob sequences can be amino- or carboxy-terminal to the ob sequences. More preferably, for stable expression of a proteolytically inactive ob fusion protein, the portion of the non-ob fusion protein is joined via a peptide bond to the amino terminus of the ob protein. A recombinant DNA molecule encoding such a fusion protein comprises a sequence encoding at least a functionally active portion of a non-ob protein joined in-frame to the ob coding sequence, and preferably encodes a cleavage site for a specific protease, e.g., thrombin or Factor Xa, preferably at the ob-non-ob juncture. In a specific embodiment, the fusion protein is expressed in *Escherichia coli* or in *P. pastoris*.

In a specific embodiment, infra, vectors were prepared to express the murine and human ob genes, with and without the codon for gln-49, in bacterial expression systems and yeast (Pichia) expression systems as fusion proteins. The ob gene is prepared with an endonuclease cleavage site, e.g., using PCR and novel primers. It is desirable to confirm sequences generated by PCR, since the probability of including a point mutation is greater with this technique. A plasmid containing a histidine tag (HIS-TAG) and a proteolytic cleavage site is used. The presence of the histidine makes possible the selective isolation of recombinant proteins on a Ni-chelation column, or by affinity purification. The proteolytic cleavage site, in a specific embodiment, infra, a thrombin cleavage site, is engineered so that treatment with the protease, e.g., thrombin, will release the full length mature (i.e., lacking a signal sequence) ob polypeptide.

In another aspect, the pGEX vector (Smith and Johnson, 1988, Gene 67:31–40) can be used. This vector fuses the schistosoma japonicum glutathionine S-transferase cDNA to the sequence of interest. Bacterial proteins are harvested and recombinant proteins can be quickly purified on a reduced glutathione affinity column. The GST carrier can subsequently be cleaved from fusion proteins by digestion with site-specific proteases. After cleavage, the carrier and uncleaved fusion protein can be removed by absorption on glutathione agarose. Difficulty with the system occasionally arises when the encoded protein is insoluble in aqueous solutions.

Expression of recombinant proteins in bacterial systems may result in incorrect folding of the expressed protein, requiring refolding. The recombinant protein can be refolded prior to or after cleavage to form a functionally active ob polypeptide. The ob polypeptide may be refolded by the steps of (i) incubating the protein in a denaturing buffer that contains a reducing agent, and then (ii) incubating the protein in a buffer that contains an oxidizing agent, and preferably also contains a protein stabilizing agent or a chaotropic agent, or both. Suitable redox (reducing/oxidizing) agent pairs include, but are not limited to, reduced glutathione/glutathione disulfide, cystine/cysteine, cystamine/cysteamine, and 2-mercaptoethanol/2-hydroxyethyldisulfide. In a particular aspect, the fusion protein can be solubilized in a denaturant, such as urea, prior to exchange into the reducing buffer. In preferred embodiment, the protein is also purified, e.g., by ion exchange or Ni-chelation chromatography, prior to exchange into the reducing buffer. Denaturing agents include but are not limited to urea and guanidine-HCl. The recombinant protein is then diluted about at least 10-fold, more preferably about 100-fold, into an oxidizing buffer that contains an oxidizing agent, such as but not limited to 0.1M Tris-HCl, pH 8.0, 1 mM EDTA, 0.15M NaCl, 0.3M oxidized glutathione. The fusion protein is then incubated for about 1 to about 24 hours, preferably about 2 to about 16 hours, at room temperature in the oxidizing buffer. The oxidizing buffer may comprise a protein stabilizing agent, e.g., a sugar, an alcohol, or ammonium sulfate. The oxidizing buffer may further comprises a chaotropic agent at low concentration, to destabilize incorrect intermolecular interactions and thus promote proper folding. Suitable chaotropic agents include but are not limited to a detergent, a polyol, L-arginine, guanidine-HCl and polyethylene glycol (PEG). It is important to use a low enough concentration of the chaotropic agent to avoid denaturing the protein. The refolded protein can be concentrated by at least about 10-fold, more preferably by the amount it was diluted into the oxidizing buffer.

Bacterial fermentation processes can also result in a recombinant protein preparation that contains unacceptable levels of endotoxins. Therefore, the invention contemplates removal of such endotoxins, e.g., by using endotoxin-specific antibodies or other endotoxin binding molecules. The presence of endotoxins can be determined by standard techniques, such as by employing E-TOXATE Reagents (Sigma), or with bioassays.

In addition to the specific example, the present inventors contemplate use of baculovirus, mammalian, and yeast expression systems to express the ob protein. For example, in baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)).

Mammalian expression vectors contemplated for use in the invention include vectors with inducible promoters, such as dihydrofolate reductase (DHFR), e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12, 1991). Alternatively, a glutamine synthetase/methionine sulfoximine co-amplification vector, such as pEE14 (HindIII, XbaI, SmaI, SmaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV LTR promoter, histidinol selectable marker; Invitrogen), pREP9 (KpnI, NheI, HindIII, NotI, XhoI, SfiI, and BamHI cloning site, RSV LTR promoter, G418 selectable marker; Invitrogen), and pEBVHis (RSV LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and HpA cloning site, TK or XPRT selection).

Yeast expression systems can also be used according to the invention to express ob polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

It is further intended that body weight modulator peptide analogs may be prepared from nucleotide sequences derived within the scope of the present invention. Analogs, such as fragments, may be produced, for example, by pepsin digestion of weight modulator peptide material. Other analogs, such as muteins, can be produced by standard site-directed mutagenesis of weight modulator peptide coding sequences. Analogs exhibiting "weight modulator activity" such as small molecules, whether functioning as promoters or inhibitors, may be identified by known in vivo and/or in vitro assays.

In addition to recombinant expression of ob polypeptide, the present invention envisions and fully enables preparation of ob polypeptide, or fragments thereof, using the well known and highly developed techniques of solid phase peptide synthesis. The invention contemplates using both the popular Boc and Fmoc, as well as other protecting group strategies, for preparing ob polypeptide or fragments thereof. Various techniques for refolding and oxidizing the cysteine side chains to form a disulfide bond are also well known in the art.

As mentioned above, a DNA sequence encoding weight modulator peptides as disclosed herein can be prepared synthetically rather than cloned. The DNA sequence can be designed with the appropriate codons for the weight modulator peptide amino acid sequences. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express weight modulator analogs or "muteins". Alternatively, DNA encoding muteins can be made by site-directed mutagenesis of native modulator genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs of the ob polypeptide with unnatural amino acids.

The present invention extends to the preparation of antisense nucleotides and ribozymes that may be used to interfere with the expression of the weight modulator proteins at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule (See Weintraub, 1990; Marcus-Sekura, 1988). In the cell, they hybridize to that mRNA, forming a double stranded molecule. The cell does not translate an mRNA in this double-stranded form. Therefore, antisense nucleic acids interfere with the expression of mRNA into protein.

Oligomers of about fifteen nucleotides and molecules that hybridize to the AUG initiation codon will be particularly efficient, since they are easy to synthesize and are likely to pose fewer problems than larger molecules when introducing them into weight modulator peptide-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988). Because they are sequence-specific, only mRNAs with particular sequences are inactivated.

Investigators have identified two types of ribozymes, Tetrahymena-type and "hammerhead"-type (Hasselhoff and Gerlach, 1988). Tetrahymena-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against and ribozymes that cleave mRNAs for weight modulator proteins and their ligands, thus inhibiting expression of the ob gene, and leading to increased weight gain and adiposity.

The present invention also relates to a variety of diagnostic applications, including methods for detecting the presence of conditions and/or stimuli that impact abnormalities in body weight or adiposity, by reference to their ability to elicit the activities which are mediated by the present weight modulators. As mentioned earlier, the weight modulator peptides can be used to produce antibodies to themselves by a variety of known techniques, and such antibodies could then be isolated and utilized as in tests for the presence of particular transcriptional activity in suspect target cells.

Antibody(ies) to the body weight modulators, i.e., the ob polypeptide, can be produced and isolated by standard methods including the well known hybridoma techniques. For convenience, the antibody(ies) to the weight modulators will be referred to herein as $Ab_1$, and antibody(ies) raised in another species as $Ab_2$.

According to the invention, ob polypeptide produced recombinantly or by chemical synthesis, and fragments or other derivatives or analogs thereof, including fusion proteins, may be used as an immunogen to generate antibodies that recognize the ob polypeptide. Such antibodies include but are not limited to polyclonal, monoclonal, chimeric, single chain, Fab fragments, and an Fab expression library.

Various procedures known in the art may be used for the production of polyclonal antibodies to ob polypeptide a recombinant PTP or derivative or analog thereof. For the production of antibody, various host animals can be immunized by injection with the ob polypeptide, or a derivative (e.g., fragment or fusion protein) thereof, including but not limited to rabbits, mice, rats, sheep, goats, etc. In one embodiment, the ob polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the ob polypeptide, or fragment, analog, or derivative thereof, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for an ob polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946, 778) can be adapted to produce ob polypeptide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an ob polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an ob polypeptide, one may assay generated hybridomas for a product which binds to an ob polypeptide fragment containing such epitope. For selection of an antibody specific to an ob polypeptide from a particular species of animal, one can select on the basis of positive binding with ob polypeptide expressed by or isolated from cells of that species of animal.

The foregoing antibodies can be used in methods known in the art relating to the localization and activity of the ob polypeptide, e.g., for Western blotting, imaging ob polypeptide in situ, measuring levels thereof in appropriate physiological samples, etc.

In a specific embodiment, antibodies that agonize or antagonize the activity of ob polypeptide can be generated. Such antibodies can be tested using the assays described infra for identifying ligands.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the gex vector can be used to express the polypeptide (Smith and Johnson, supra). Alternatively, one can use only hydrophilic domains to generate the fusion protein. The expressed protein will be prepared in quantity and used to immunize rabbits in Freunds adjuvant.

The presence of weight modulator in cells can be ascertained by the usual immunological procedures applicable to such determinations. A number of useful procedures are known. Three such procedures which are especially useful utilize either the receptor recognition factor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "WM" stands for the weight modulator:

| | |
|---|---|
| $WM^* + Ab_1 = WM^*Ab_1$ | A. |
| $WM + Ab^* = WMAb_1^*$ | B. |
| $WM + Ab_1 + Ab_2^* = Ab_1WMAb_2^*$ | C. |

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure B is representative of the well known competitive assay techniques. Procedure C, the "sandwich" procedure, is described in U.S. Pat. Nos. RE 31,006 and 4,016,043. Still other procedures are known such as the "double antibody", or "DASP" procedure.

In each instance, the weight modulators form complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-weight modulator antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The weight modulators or their binding partners can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system that is to be utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the weight modulator may be radiolabeled and combined, for example, with antibodies or other inhibitors thereto, after which binding studies would be carried out. Solutions would then be prepared that contain various quantities of labeled and unlabeled uncombined weight modulator, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic. In turn, a receptor assay will be particularly useful in the identification of the specific receptors to the present modulators, such as the db receptor.

A further assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled weight modulator or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present weight modulator or a specific binding partner thereto, to a detectable label;

(b) other reagents; and (c) directions for use of said kit.

More specifically, the diagnostic test kit may comprise:

(a) a known amount of the weight modulator as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the weight modulator to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the weight modulator and a specific binding partner thereto.

In accordance with the above, an assay system for screening potential drugs effective to mimic or antagonize the activity of the weight modulator may be prepared. The weight modulator may be introduced into a test system, and the prospective drug may also be introduced into the resulting cell culture, and the culture thereafter examined to observe any changes in the activity of the cells, due either to the addition of the prospective drug alone, or due to the effect of added quantities of the known weight modulator.

As stated earlier, the molecular cloning of the ob gene described herein has led to the identification of a class of materials that function on the molecular level to modulate mammalian body weight. The discovery of the modulators of the invention has important implications for the diagnosis and treatment of nutritional disorders including, but not limited to, obesity, weight loss associated with cancer and the treatment of diseases associated with obesity such as hypertension, heart disease and Type II diabetes. In addition, there are potential agricultural uses for the gene product in cases where one might wish to modulate the body weight of domestic animals. Finally, to the extent that one or more of the modulators of the invention are secreted molecules, they can be used biochemically to isolate their receptor using the technology of expression cloning. The discussion that follows with specific reference to the ob gene bears general applicability to the class of modulators that a part of the present invention, and is therefore to be accorded such latitude and scope of interpretation.

Therapeutic Implications

In the simplest analysis the ob gene determines body weight in mammals, in particular mice and man. The ob gene and, correspondingly, cognate molecules, appear to be part of a signaling pathway by which adipose tissue communicates with the brain and the other organs. It is believed that the ob polypeptide is itself a signaling molecule, i.e., a hormone. Alternatively ob may be responsible for the generation of a metabolic signal, e.g., a stimulating hormone or an enzyme that catalyzes activation or synthesis of a peptide or steroid hormone. The most important piece of information for distinguishing between these possibilities or considering alternative hypothesis, is the complete DNA sequence of the RNA and its predicted protein sequence. Irrespective of its biochemical function the genetic data suggest that increased activity of ob would result in weight loss while decreased activity would be associated with weight gain. The means by which the activity of ob can be modified so as to lead to a therapeutic effect depends on its biochemical function.

Administration of recombinant ob polypeptide can result in weight loss. Recombinant protein can be prepared using standard bacterial and/or manmmalian expression vectors, all as stated in detail earlier herein. Reduction of ob polypeptide activity (by developing antagonists, inhibitors, or antisense molecules) should result in weight gain as might be desirable for the treatment of the weight loss associated with cancer, AIDS or anorexia nervosa. Modulation of ob activity can be useful for reducing body weight (by increasing its activity) or increasing body weight (by decreasing its activity).

The ob polypeptide, or functionally active fragment thereof, or an antagonist thereof, can be administered orally or parenterally, preferably parenterally. Because metabolic homeostasis is a continuous process, controlled release administration of ob polypeptide is preferred. For example, the polypeptide may be administered using intravenous infusion, an implantable osmotic pump, a transdermal patch, liposomes, or other modes of administration. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115–138 (1984)). Other controlled release systems are discussed in the review by Langer (*Science* 249:1527–1533 (1990)). In another embodiment, the therapeutic compound can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler (eds.), Liss, N.Y., pp. 353–365 (1989); Lopez-Berestein, ibid., pp. 317–327; see generally ibid.)

In a further aspect, recombinant cells that have been transformed with the ob gene and that express high levels of the polypeptide can be transplanted in a subject in need of ob polypeptide. Preferably autologous cells transformed with ob are transplanted to avoid rejection; alternatively, technology is available to shield nonautologous cells that produce soluble factors within a polymer matrix that prevents immune recognition and rejection.

Thus, the ob polypeptide can be delivered by intravenous, intraarterial, intraperitoneal, intramuscular, or subcutaneous routes of administration. Alternatively, the ob polypeptide, properly formulated, can be administered by nasal or oral administration. A constant supply of ob can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

Alternatively, the ob gene could be introduced into human fat cells to develop gene therapy for obesity. Such therapy would be expected to decrease body weight. Conversely, introduction of antisense constructs into human fat cells would reduce the levels of active ob polypeptide and would be predicted to increase body adiposity.

If ob is an enzyme, strategies have begun to be developed for the identification of the substrate and product of the catalyzed reaction that would make use of the recombinant protein. The rationale for this strategy is as follows: If ob is an enzyme that catalyzes a particular reaction in adipose tissue, then fat cells from ob mice should have high levels of the substrate and very little product. Since it is hypothesized that db mice are resistant to the product of this reaction, fat cells from db mice should have high levels of the reaction product. Thus, comparisons of lipid and peptide extracts of ob and db adipose tissue using gas chromatography or other chromatographic methods should allow the identification of the product and substrate of the key chemical reaction. The prediction would be that the recombinant ob protein would catalyze this reaction. The product of this reaction would then be a candidate for a signaling molecule that modulates body weight.

As noted above, the functional activity of the ob polypeptide can be effected transgenically,, e.g., by gene therapy. In this respect, a transgenic mouse model can be used. The ob gene can be used in complementation studies employing transgenic mice. Transgenic vectors, including viral vectors, or cosmid clones (or phage clones) corresponding to the wild type locus of candidate gene, can be constructed using the isolated ob gene. Cosmids may be introduced into transgenic mice using published procedures (Jaenisch, *Science* 240, 1468–1474, 1988). The constructs are introduced into fertilized eggs derived from an intercross between F1 progeny of a C57BL/6J oblob X DBA intercross. These crosses require the use of C57BL/6J oblob ovarian transplants to generate the F1 animals. DBA/2J mice are used as the counterstrain because they have a nonagouti coat color which is important when using the ovarian transplants. Genotype at the ob loci in cosmid transgenic animals can be determined by typing animals with tightly linked RFLPs or microsatellites which flank the mutation and which are polymorphic between the progenitor strains. Complementation will be demonstrated when a particular construct renders a genetically obese F2 animal (as scored by RFLP analysis) lean and nondiabetic. Under these circumstances, final proof of complementation will require that the ob/ob or db/db animal carrying the transgene be mated to the ob/ob or db/db ovarian transplants. In this cross, all N2 animals which do not carry the transgene will be obese and insulin resistant/diabetic, while those that do carry the transgene will be lean and have normal glucose and insulin concentrations in plasma. In a genetic sense, the transgene acts as a suppressor mutation.

Alternatively, ob genes can be tested by examining their phenotypic effects when express in antisense orientation in wild-type animals. In this approach, expression of the wild type allele is suppressed, which leads to a mutant phenotype.

RNA·RNA duplex formation (antisense·sense) prevents normal handling of mRNA, resulting in partial or complete elimination of wild-type gene effect. This technique has been used to inhibit Tk synthesis in tissue culture and to produce phenotypes of the Kruppel mutation in Drosophila, and the shiverer mutation in mice (Izant and Weintraub, *Cell* 36, 1007–1015, 1984; Green et al., *Annu. Rev. Biochem.* 55,569–597, 1986; Katsuki et al., *Science* 241, 593–595, 1988). An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 poly A site. This transgene will be used to make transgenic mice. Transgenic mice will also be mated ovarian transplants to test whether ob heterozygotes are more sensitive to the effects of the antisense construct.

In the long term, the elucidation of the biochemical function of the ob gene product (the ob polypeptide or protein) is useful for identifying small molecule agonists and antagonists that affect its activity.

Diagnostic Implications

The human cDNA clones that have recently been isolated have been sequenced as presented herein. This facilitates the determination of the complete sequence of the human gene (see FIG. 20). DNA sequences from the introns of the human ob gene have been obtained (FIG. 20), and these have been used to prepare PCR primers to PCR amplify the coding sequence of the ob gene from human genomic DNA so as to identify mutations or allelic variants of the ob gene, all in accordance with protocols described in detail earlier herein. Specific PCR primers for amplifying human genomic ob are described in a specific Example, infra.

The current hypothesis is that heterozygous mutations in the ob gene will be associated with mild/moderate obesity while homozygous mutations would be associated with several DNA sequence based diagnostic tests obesity. If this is true, it would allow the ascertainment of people at risk for the development of obesity and make possible the application of drug treatment and/or lifestyle changes before an increased body weight is fully developed.

Alternatively, the presence of microsatellites that segregate with mutant forms of human ob can be used for diagnosis. Various PCR primers, including those based on the nucleotide sequence provided in FIG. 20A, can be used in this respect.

The ob gene may also be useful diagnostically for measurements of its encoded RNA and protein in nutritional disorders. It will be of importance to know, in a particular nutritional disorder, whether ob RNA and/or protein is unregulated or downregulated. Thus, if an obese person has increased levels of ob, it would appear that the problem is downstream of ob, while if ob is reduced, it would appear that inappropriately low levels of ob may be cause of obesity (whether or not the defect is in the ob gene). Conversely, if a cancer or AIDS patient who lost weight had elevated levels of ob, it may be concluded that inappropriately high expression of ob is responsible for the weight loss.

The cloned human cDNA will be of use for the measurement of the levels of human ob RNA. In addition, recombinant human protein will be prepared and used to develop immunoassays to enable measurement of the fat and perhaps plasma levels of the ob protein.

Agricultural Applications

The ob gene can also be isolated from domestic animals, and the corresponding ob polypeptide obtained thereby. In a specific example, infra, the a probe derived from the murine ob gene hybridizes to corresponding homologous coding sequences from a large number of species of animals. As discussed for human therapies, recombinant proteins can also be prepared and administered to domestic animals. Administration of the polypeptide can be implemented to produce leaner food animals, such as beef cattle, swine, poultry, sheep, etc. Preferably, an autologous ob polypeptide is administered, although the invention contemplates administration of anti-autologous polypeptide as well. Since the ob polypeptide consists of approximately 160 amino acid residues, it may not be highly immunogenic. Thus, administration of non-autologous polypeptide may not result in an immune response.

Alternatively, the introduction of the cloned genes into transgenic domestic animals would allow one to potentially decrease body weight and adiposity by overexpressing an ob transgene. The simplest means of achieving this would be to target an ob transgene to fat using its own or another fat specific promoter.

Conversely, increases in body fat might be desirable in other circumstances such as for the development of Kobe beef or fatty liver to make foie gras. This could be accomplished by targeting an antisense ob transgene to fat, or by using gene knockout technology. Alternatively, where an increase in body weight at percentage of fat is desired, an inhibitor or antagonist of the ob polypeptide can be administered. Such inhibitors or antagonists include, but are not limited to, antibodies reactive with the polypeptide, and fragments of the polypeptide that bind but do not activate the ob receptor, i.e., antagonists of ob polypeptide.

The ob Receptor

Development of small molecule agonists and antagonists of the ob factor will be greatly facilitated by the isolation of its receptor. This can be accomplished by preparing active ob polypeptide and using it to screen an expression library using standard methodology. Receptor binding in the expression library can be tested by administering recombinant polypeptide prepared using either bacterial or mammalian expression vectors, and observing the effects of short term and continuous administration of the recombinant polypeptide on the cells of the expression library, or by directly detecting binding of ob polypeptide to the cells.

As it is presently believed that the ob receptor is likely to be located in the hypothalamus and perhaps liver, preferably cDNA libraries from these tissues will be constructed in standard expression cloning vectors. These cDNA clones would next be introduced into COS cells as pools and the resulting transformants would be screened with active ligand to identify COS cells expressing the ob receptor. Positive clones can then be isolated so as to recover the cloned receptor. The cloned receptor would be used in conjunction with the ob ligand (assuming it is a hormone) to develop the necessary components for screening of small molecule modulators of ob.

Once a recombinant which expresses the ob receptor gene sequence is identified, the recombinant ob receptor can be analyzed. This is achieved by assays based on the physical or functional properties of the ob receptor, including radioactive labelling of the receptor followed by analysis by gel electrophoresis, immunoassay, ligand binding, etc. Furthermore, antibodies to the ob receptor could be generated as described above.

The structure of the ob receptor can be analyzed by various methods known in the art. Preferably, the structure of the various domains, particularly the ob binding site, is analyzed. Structural analysis can be performed by identifying sequence similarity with other known proteins, particular hormone and protein receptors. The degree of similarity (or homology) can provide a basis for predicting structure and function of the ob receptor, or a domain thereof. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the ob receptor protein, which may in turn indicate extracytoplasmic, membrane binding, and intracytoplasmic regions.

Secondary structural analysis (e.g., Chou and Fasman, 1974, Biochemistry 13:222) can also be done, to identify regions of the ob receptor that assume specific secondary structures.

Manipulation, translation, and secondary structure prediction, as well as open reading frame prediction and plotting, can also be accomplished using computer software programs available in the art.

By providing an abundant source of recombinant ob polypeptide, and the opportunity to isolate the ob receptor (i.e., the db gene product), the present invention enables quantitative structural determination of the active conformation of the ob polypeptide and the ob receptor, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13).

More preferably, co-crystals of ob polypeptide and ob receptor can be studied. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

Identification and isolation of a gene encoding an ob receptor of the invention provides for expression of the receptor in quantities greater than can be isolated from natural sources, or in indicator cells that are specially engineered to indicate the activity of a receptor expressed after transfection or transformation of the cells. According, in addition to rational design of agonists and antagonists based on the structure of ob polypeptide, the present invention contemplates an alternative method for identifying specific ligands of ob receptor using various screening assays known in the art.

Any screening technique known in the art can be used to screen for ob receptor agonists or antagonists. The present invention contemplates screens for small molecule ligands or ligand analogs and mimics, as well as screens for natural ligands that bind to and agonize or antagonize activates ob receptor in vivo.

Knowledge of the primary sequence of the receptor, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, mnt. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., 1993, "Generation and screening of an oligonucleotide encoded synthetic peptide library," Proc. Natl. Acad. Sci. USA 90:10700–4; Lam et al., International Pat. Publication No. WO 92/00252, each of which is incorporated herein by reference in its entirety), and the like can be used to screen for ob receptor ligands according to the present invention. With such libraries, receptor antagonists can be detected using cell that express the receptor without actually cloning the ob receptor (Lam et al., supra).

Alternatively, assays for binding of soluble ligand to cells that express recombinant forms of the ob receptor ligand binding domain can be performed. The soluble ligands can be provided readily as recombinant or synthetic ob polypeptide.

The screening can be performed with recombinant cells that express the ob receptor, or alternatively, using purified receptor protein, e.g., produced recombinantly, as described above. For example, the ability of labeled, soluble or solubilized ob receptor that includes the ligand-binding portion of the molecule, to bind ligand can be used to screen libraries, as described in the foregoing references.

EXAMPLE SECTION

The following outlines the method used to identify the genetic material that is exemplary of the present invention. This endeavor comprises four sequential steps: A) Genetic Mapping, B) Physical Mapping, C) Candidate Gene Isolation, and D) Mutation detection. Following confirmation that the murine gene in object was isolated (Step D), the homologous human gene was sought, and both the murine and human genes and putative proteins were characterized. The steps are summarized in greater detail, below.

A. Genetic Mapping

The ob mutation was segregated in genetic crosses and standard linkage analysis was used to position the mutation relative to RFLPs (restriction fragment length polymorphisms). These data placed the ob gene in an ~5 cM interval on proximal mouse chromosome 6. (5 cM is a measurement of genetic distance corresponding to 5 apparent genetic crossovers per 100 animals.) A total of 771 informative meioses were generated and used in subsequent genetic mapping (Friedman et al. *Genomics* 11: 1054–1062, 1991). The genetic loci that were mapped relative to ob were all previously published. The two closest RFLPs described were defined by probes derived from the carboxypeptidase and met oncogene genes.

The genetic resolution of the experiments described above was inadequate to clone ob, principally because none of the genetic markers were in tight linkage. In order to identify the requisite tightly linked RFLPs, additional probes were isolated and the genetic cross was expanded. A method known as chromosome microdissection was used to isolate random pieces of DNA from proximal mouse chromosome 6 (Bahary et al., *Mammalian Genome* 4: 511–515, 1993). Individual cloned probes were tested for tight linkage to ob. On the basis of these studies one probe, D6Rck13, also termed psd3, was selected for further analysis owing to its genetic proximity to ob.

This probe was used to genotype 835 ob progeny from interspecific and intersubspecific crosses, which indicated that D6Rck13 is nonrecombinant in all 835 animals as reported in Bahary et al. In the course of physical mapping, a new polymorphic marker was identified from a cosmid subclone derived from YAC 53A6. This new marker was positioned between D6Rck13 and the ob gene and was used to genotype the additional 771 informative meioses from intraspecific intercross and backcross. A single animal #167 was identified to bear a recombination crossover between ob and D6Rck39. These studies indicated that D6Rck39/D6RcK13 is ~0.06 cM from ob. An additional probe, Pax-4, was identified that was 0.12 cM proximal to ob. Pax-4 was recombinant in two animals; #111 and 420. Pax-4 is a pseudogene that was previously mapped to proximal mouse chromosome 6 by Gruss and co-workers (Gruss et al. *Genomics* 11:424–434, 1991). On this basis, it was determined that the ob gene resides in the ~0.2 cM interval between Pax-4 and D6Rck13. This led to efforts to clone the interposing DNA in an effort to isolate ob.

B. Physical Mapping

The cloning of the DNA in this interval made use of yeast artificial chromosomes (YACs), a relatively new cloning vector that allows the cloning of long stretches of contiguous DNA often more than 1 million base pairs in length.

Firstly, yeast artificial chromosomes were isolated using D6Rck13 and Pax-4. This was accomplished by preparing purified DNA probes and using them to isolate the corresponding YACs. These YACs (#8, 16, 107 and 24) were isolated and initially characterized, and on the basis of the resulting analyses it was concluded that YAC 16 was the YAC that extended furthest distally, i.e., closest to ob. The key end of YAC #16 was then recovered, and it was determined that this end was closer to ob than Pax-4. This end was termed 16M(+). This conclusion was reached because it was shown that this probe was not recombinant in animal #420 (as was Pax-4). This end was sequenced and used to develop a PCR assay. This PCR assay was used to screen a YAC library. Four positive clones were isolated. Subsequent characterization of these YACs by end-rescuing, restriction mapping, pulse field gel electrophoresis, and Southern blots with the genetic crosses determined that two of these YACs, adu and aad, were critical for subsequent studies. YAC aad is a 550 kB nonchimeric YAC which extended furthest distally. Therefore, the distal end of this YAC, aad(pICL) was used to complete the physical map. YAC adu is 370 kB nonchimeric YAC and its distal end, adu(+), was determined to be nonrecombinant in all the ob progeny of the genetic crosses including animals #111 and 167, suggesting that the ob gene might reside in this YAC.

A PCR assay for these two ends, aad(pICL) and adu(+) was developed and used for isolating moire YACs and P1 clones to continue physical mapping. The important P1 clones isolated by this effort included 498, 499, 500 (isolated using a probe derived from aad(pICL)) and 322, 323 and 324 (using a probe from adu(+)).

In the meantime, YACs isolated by D6Rck13 (53A6, 25A8, 25A9, 25A10) were characterized. These studies determined that 53A6 extended furthest proximally toward the aad YAC. The size of the gap between 53A6 and aad was determined ~70 kB. The key end of 53A6, 53(pICL) was then used to screen three available YAC libraries and a P1 library. A critical P1 clone, 325, was isolated. This P1 clone overlapped with the P1 clones isolated by aad(pICL) as described above, and therefore served to close the gap between 53(pICL) and aad(pICL). As a result, the whole contig, containing YACs and P1 clones, of ~2.5 million base pairs in length, and which spanned Pax4, 16M(+), adu(+), aad(pICL), 53(pICL), D6Rck39 and D6Rck13, was cloned. By carefully mapping the sites of recombination apparent in animal #111 and 167, it was concluded that ob was situated in a 400 kB interval. To provide a working DNA source for isolating the ob gene, about 500 kB covering this nonrecombination region was isolated in a total of 24 P1 clones. These P1 clones, including 322 and 323, which later were proved to be useful clones, were used for exon trapping.

The physical map of the portion of the chromosome carrying ob is shown in FIG. 7A. FIG. 7B represents the YAC contig. FIG. 7C represents the P1 contig.

C. Isolation of Candidate Genes

The method used to isolate genes in this interval was exon trapping. This method used a commercial vector to identify exon DNA (i.e., coding sequences) by selecting for functional splice acceptor and donor sequences in genomic DNA introduced into a test construct. The DNA from these P1s were grown and subcloned into the exon trapping vector. These clones were short inserts cloned into a Bluescript vector. Each clone was PCR amplified with PCR primers corresponding to plasmid sequences that flanked the insert. The PCR amplification was performed directly on the bacteria that carried the plasmid. The reactions were set up using a Biomek robot. The PCR products were electrophoresed on a 1% agarose gel in TBE buffer that contained ethidium bromide. The exon trapping technique was modified to eliminate contaminating *E. coli* DNA from the P1 clones, and to screen out the abundant artifactual exons, which exceeded 80–90% of the putative exons trapped. The exon trapping vector includes HIV sequences; a short segment of these vector sequences corresponds to this artifact.

The exon trapping experiment was performed using various P1 clones. Exon trapping products were then amplified by PCR, selected, and sequenced. Sequences of putative "exons" were compared with those in Genbank using the Blast computer program. About 15 exons were selected for further examination by RT-PCR, Northern analysis, and zoo blot for the presence of corresponding RNA or conservative sequences. Seven of the 15 putative exons, 325-2, 323-9, 322-5, D1-F7, 1H3, and 2G7, were found to encode an RNA transcript. 325-2 is a testis specific gene; 323-8 and 323-9 are likely two exons from the same gene expressed mainly in brain and kidney. IH3 and 322–5 represent two low level brain transcripts. D1-F7 is an exon from a previously cloned gene, inosine monophosphate dehydrogenase (IMPDH), which has ubiquitous expression pattern. None of these genes appeared to encode ob. 2G7, which is the ob exon, is discussed further below.

After three unsuccessful efforts to exon trap the ob gene, another attempt was made by pooling DNA from all the P1s from the critical ob region. These included P1s: 258, 259, 322, 323, 324, 325, 498, 499, 500, 653, 654 and others. Thereafter P1s 258, 260, 322, 498 and 499 were subcloned into the exon trapping vector, and subsequently several plates were prepared with bacterial clones, each of which carried a putative exon. Approximately 192 clones representing putative ob candidates were obtained. As noted above, a consistent artifact such that many of the isolates contained two trapped exons derived from the vector was observed. Thus, clones were identified both by their size and the fact that hybridization of DNA probes corresponding to this artifact hybridized to the corresponding bands on a Southern blot of the gel. In this way, 185 out of 192 clones were excluded from further evaluation. Exclusion of the artifacts on the basis of size alone was not possible, as this could have, in the end, led to exclusion of the exon corresponding to ob.

Thus, of the 192 exons, a total of seven exons were selected for further study. Templates for sequencing the seven exons were prepared, and sequencing was performed. The sequences for the 7 exons were analyzed and it was found that 4 were identical and one was an apparent artifact. In particular, clone 1D12 contained the "HIV sequence," i.e., the artifact band. This left three exons for further analysis: 1F1, 2G7 and 1H3. 1F1 was eliminated because it mapped outside the critical region. PCR primers for both 1H3 and 2G7 were selected and synthesized.

The sequence of the exon on 2G7 was determined, and is shown in FIG. 10 (SEQ ID NO:7). PCR primers for 2G7 were selected and synthesized. The portions of the sequence corresponding to the PCR primers are underlined. The primers used were:

5' CCA GGG CAG GAA AAT GTG (Tm=60.0) (SEQ ID NO:8)

3' CAT CCT GGA CTT TCT GGA TAG G (Tm =60.0) (SEQ ID NO:9)

These primers amplified genome DNA with PCR conditions as follows: 25–30 cycles at 55° annealing×2', 72° extension× 2', 94° denaturation×1' in standard PCR buffer. These primers were also used to generate a labeled probe by including $^{32}$P dCTP in the PCR reaction with a corresponding reduction in the amount of cold dCTP.

Figure 11A:
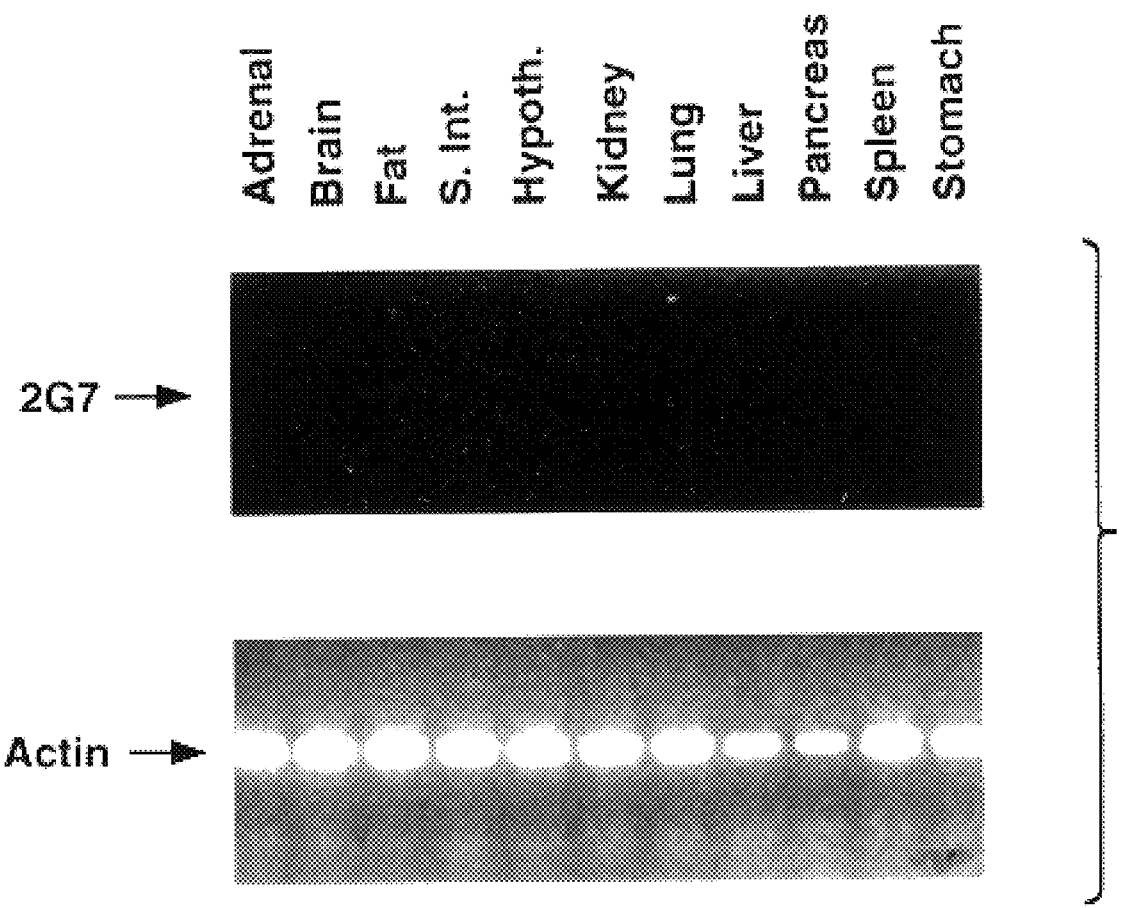
FIGS. 11A–B. (A) Reverse transcription-PCR analysis of mRNA from different tissues of the same mouse with the 2G7 primers and actin primers. The RT-PCR reactions were performed using 100 ng of total RNA reverse transcribed with oligo dT as a primer for first strand cDNA. PCR amplification was performed for 35 cycles with 94° denaturation×1'; 55° hybridization×1'; and 72 extensions for 2' with a 1' second autoextension per cycle. RT-PCR products were resolved in a 2% low melting point agarose gel run in 1× TBE buffer. (B) Northern blot of mRNA from different organs of the mouse using PCR labeled 2G7 as a probe. Ten μg of total RNA from each of the tissues was electrophoresed on an agarose gel with formaldehyde. The probe was hybridized at 65° C. in Rapid Hybe (Amersham). Autoradiographic signals were apparent after 1 hour of exposure; the experiment shown was the result of a 24 hour exposure.
Figure 11B:
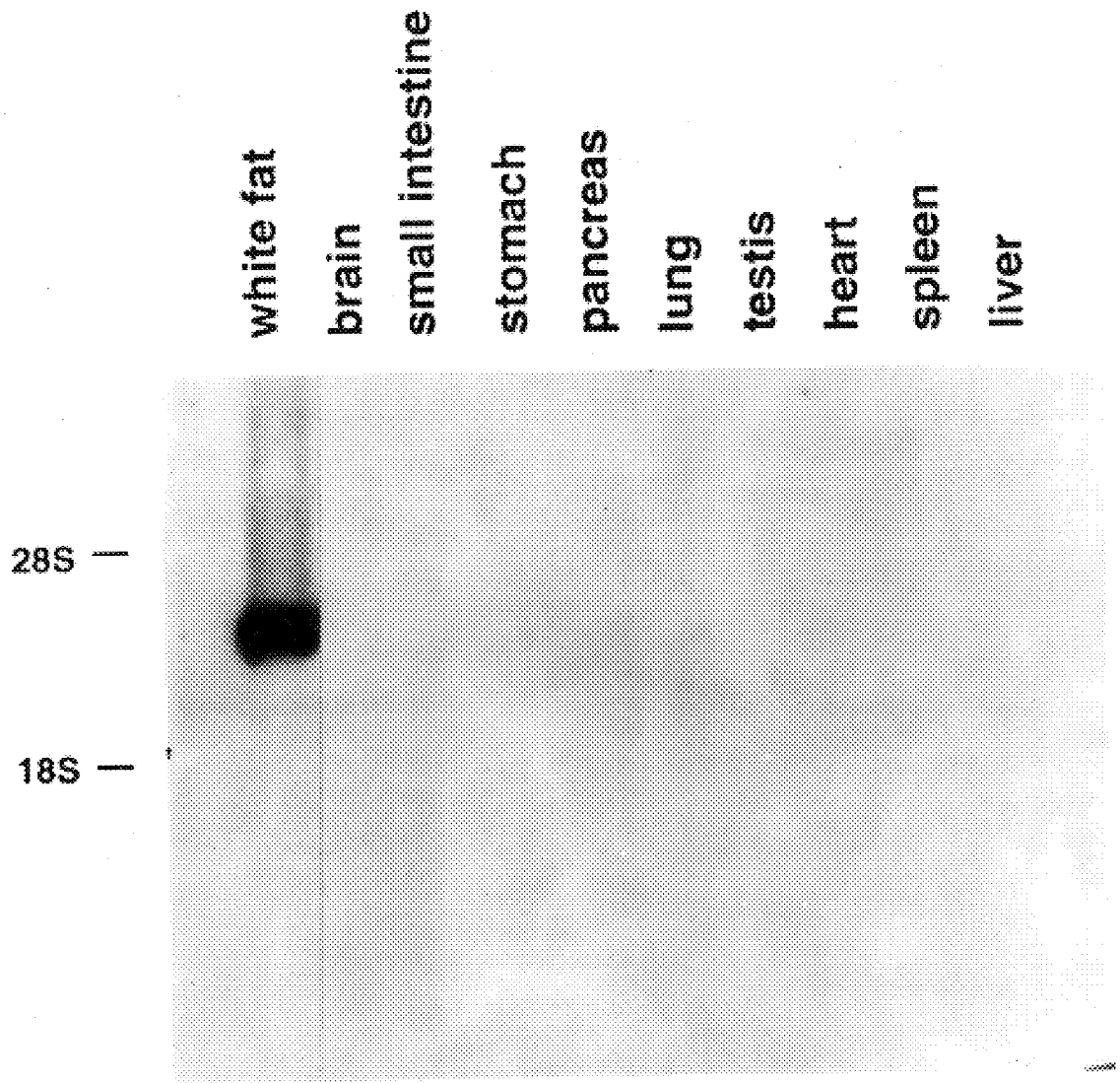

A RT PCR was performed on a variety of tissue RNAs and it was concluded that 2G7 was expressed exclusively in white fat among the tissues examined (FIG. 11A). Thereafter, $^{32}$P-labelled 2G7 was hybridized to a Northern blot of tissue RNAs (FIG. 11B) and showed that its RNA was expressed at high level in fat tissue but was either not expressed or expressed at very low levels in all other tissues (where the signals may be the result of fat contaminating the tissue preparations). Ten μg of total RNA from each of the tissues listed was electrophoresed on an agarose gel with formaldehyde. The probe was hybridized at 65° in a standard hybridization buffer, Rapid Hype (Amersham). The size of the RNA was approximately 4.9 kB. At this point 2G7 was considered to be a viable candidate gene for ob and was analyzed further.

D. Mutation Detection

Figure 12A:
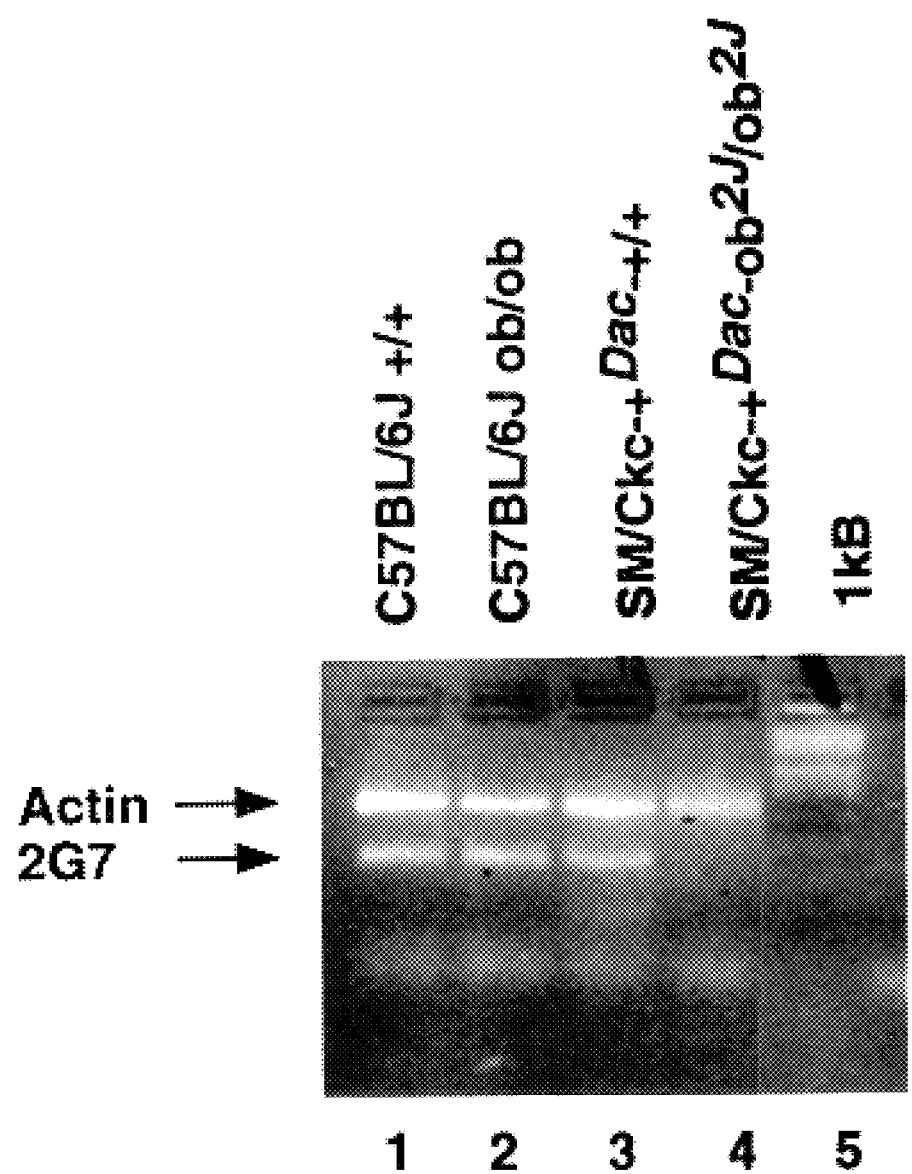
FIGS. 12A–B. (A) An ethidium bromide stain from an RT PCR reaction on fat cell (white adipose tissue) RNA from each of the mouse strains listed. Total RNA (100 ng) for each sample was reverse transcribed using oligo dT and reverse transcriptase, and the resulting single stranded cDNA was PCR amplified with the 2G7 primers (lower bands) or actin primers (upper bands). Both the 2G7 and actin primers were included in the same PCR reaction. The products were run on a 1% agarose TBE gel. (B) Northern analysis corresponding to (A). Ten μg of fat cell (white adipose tissue) RNA from each of the strains indicated were run out and probed with the PCR labeled 2G7 probe as in FIG. 11B, above. An approximately 20-fold increase in the level of 2G7 mRNA was apparent in white fate RNA from the C57BL/6J ob/ob (1J) strain relative to lean littermates. In both the RT-PCR and Northern experiments there was no detectable signal in 2G7 RNA from the SM/Ckc-+$^{Dac}$ob$^{2J}$/ob$^{2J}$ (2J) mice even after a 2 week exposure. A 24 hour autoradiographic exposure is shown. The same filter was hybridized to an actin probe (bottom portion of the panel).

In order to confirm that 2G7 encoded the ob gene, it was necessary to demonstrate differences in the levels of RNA expression of DNA sequence of this gene in mutant as compared to wild type animals. Two separate mutations of the ob gene are available for study, C57BL/6J ob/ob (1J) and Ckc/Smj ob/ob (2J). These will be referred hereinafter as 1J and 2J, respectively. (Informal nomenclature is used to refer to the mouse strains studied. Throughout this specification and in the drawings, it will be understood that C57BL/6J refers to C57BL/6J +/+; CKC/smj refers to SM/Ckc-+$^{Dac}$-+/+; CKC/smj ob/ob refers to SM/Ckc-+$^{Dac}$-ob$^{2J}$/ob$^{2J}$). RNA was prepared from fat tissue that had been isolated from 1J, 2J, and control animals. Total RNA for each sample was treated with DNase and then reverse transcribed using oligo-dT as a primer and reverse transcriptase. The resulting single stranded cDNA was then PCR amplified either with the 2G7 primers (conditions shown above) for the lower band or commercially available actin primers for the upper band. The RT PCR products were run on a 1% agarose TBE gel that was stained with ethidium bromide (FIG. 12A). Using RT-PCT it was found that while 2G7 mRNA was expressed in 1J and all the other control mice, it was completely missing in 2J mouse. No signal was detected after 30 cycles of amplification. This experiment provided direct evidence that 2G7 corresponded to an exon from the ob gene.

Since 2J mutation is relatively recent and is maintained as a coisogenic strain, this result was the first available evidence that indicated that 2G7 is an exon from the ob gene. The mutation is likely located in the promoter region which leads to total abortion of the mRNA synthesis. The presence of signal in 1J mouse in this RT-PCT experiment suggested that 1J might carry a point mutation which does not result in a gross change in size of the RNA sample. In addition, 2G7 mRNA was absent, when tested by RT PCR, from four additional 2J animals.

Figure 12B:
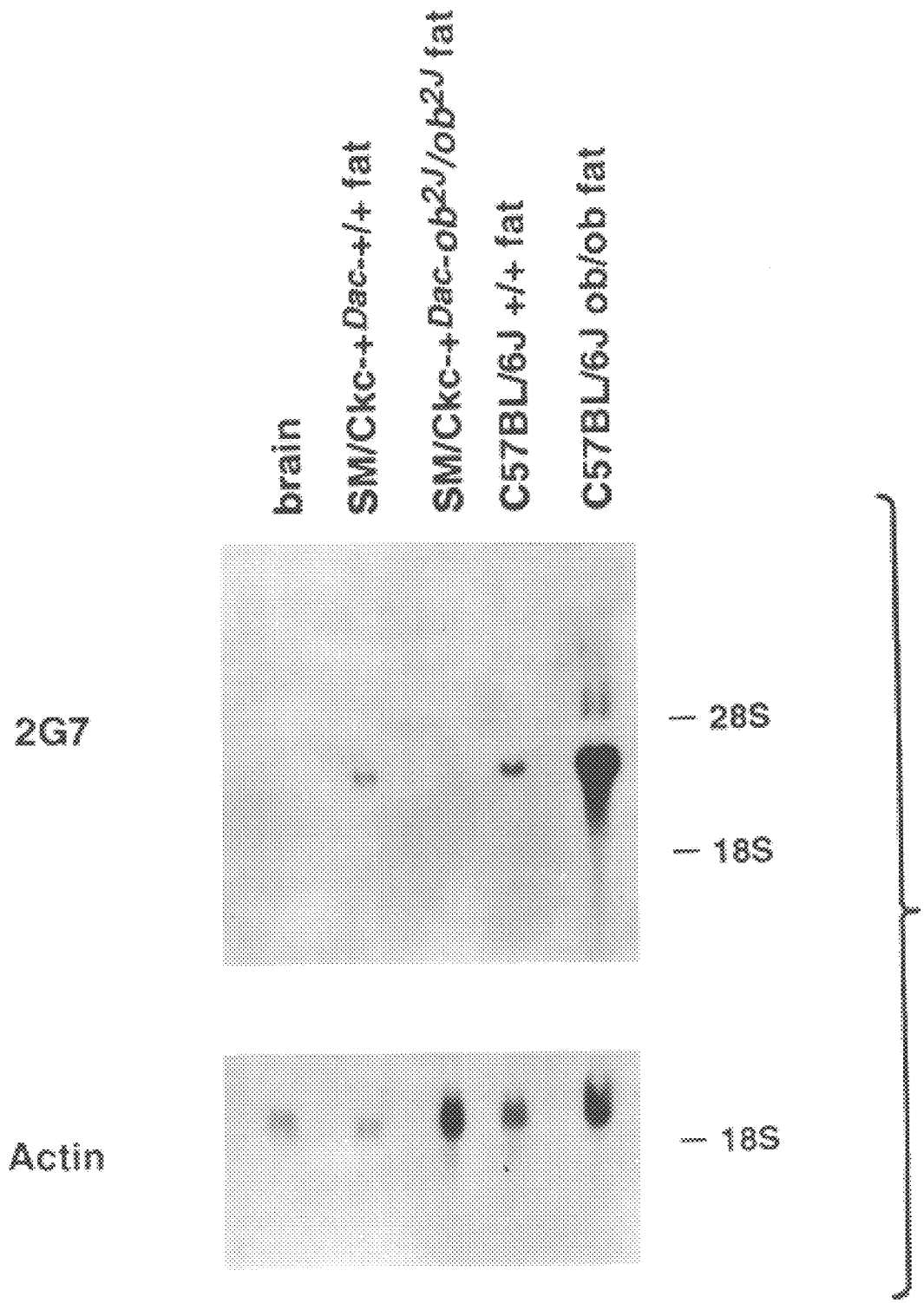

This result was confirmed on a Northern blot (FIG. 12B). Fat cell RNA was prepared from each of the strains (C57B1/6J, 1J, CKC/smj, and 2J). Ten μg of these RNAs were run out. The blot was probed with the 2G7 probe that was PCR labeled, by amplification of the material, i.e., band, in FIG. 11 using $^{32}$P-dCTP in the PCR reaction. Actin is a control for the amount of RNA loaded. The actin signal is fairly similar in all of the samples. The ob signal is absent in brain because the mRNA is specific to fat cells.

The results of the Northern analysis confirm that 2G7 RNA was absent in 2J mice. The ob RNA is absent in the CKC/smj ob/ob mice because in this obese mutant strain the gene is disrupted such that no RNA is made. In addition, the level of 2G7 RNA was increased ~10–20 fold in 1J as well as db/db fat. These results are compatible with the hypothesis that ob either encodes circulating hormone or is responsible for the generation of a signal from fat cells that modulates body weight. These results supported the conclusion that 2G7 is the ob gene and predicted that 1J mice have a point mutation, probably a nonsense mutation leading to a premature translation termination.

These Northern results have been replicated using fat cell RNA preparations from four different 2J animals (FIG. 13). In this assay, ap2 is a fat-specific transcript that was used as a control much the same as actin in FIG. 12B. There is no significance to the varying density of the ap2 band. ap2 was labeled by designing PCR primers form the published ap2 sequence. The RT PCR products of fat cell RNA were then relabeled using the same protocol for PCR labeling. This analysis demonstrates the presence of ob mRNA in normal homozygous or heterozygous animals, and its absence from 2J mutant animals.

Figure 14:
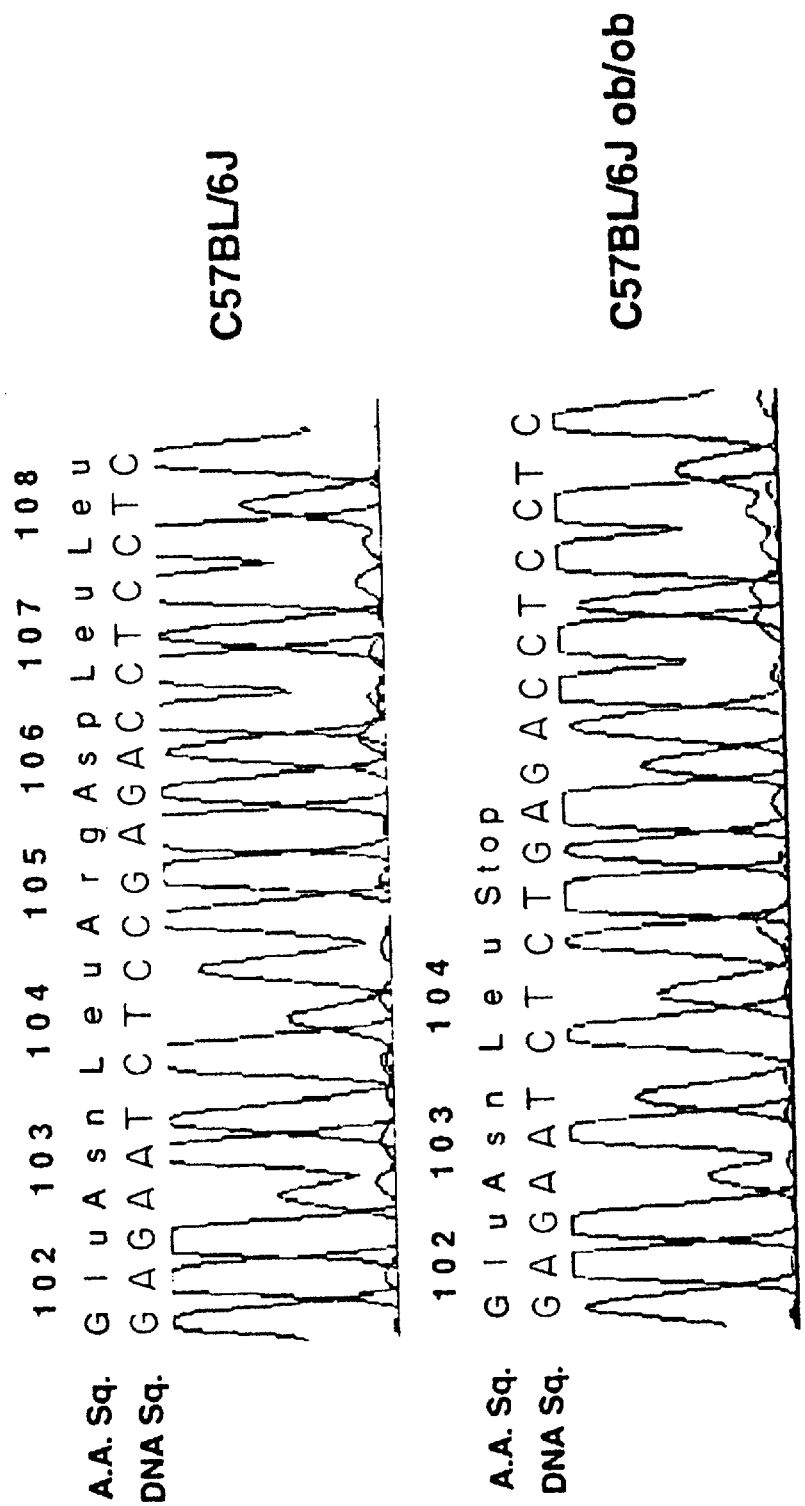
FIG. 14 compares the DNA sequence of the C57BL/6J (normal) and the C57BL/6J ob/ob (1J) mice in the region of the point mutation that leads to introduction of a premature stop codon (nonsense mutation) in the mutant strain cDNA. The ob/ob mice had a C→T mutation that changed an arginine residue at position 105. This base change is shown as the output from the automated DNA sequencer. RT-PCR was performed using white fat RNA from both strains (+/+ and ob/ob) using primers from the 5' and 3' unstranslated regions. The PCR reaction products were gel purified and directly sequenced manually and using an ABI 373A automated sequencer with primers along both strands of the coding sequence.

The mutation has been identified in 1J mice. The mutation is a C to T base change that results in change of an arginine to an apparent premature stop codon at amino acid 108, and in all likelihood accounts for the 1J mutation (FIG. 14) despite high level expression of the ob mRNA (see FIG. 12 and 13, C57BL/6J ob/ob lanes).

More recently, Southern blots have been used to conclude that the 2J mutation is the result of a detectable DNA change at the 5' end of ob that appears to completely abolish RNA expression. The exact nature of this possible rearrangement remains to be determined.

Figure 15A:
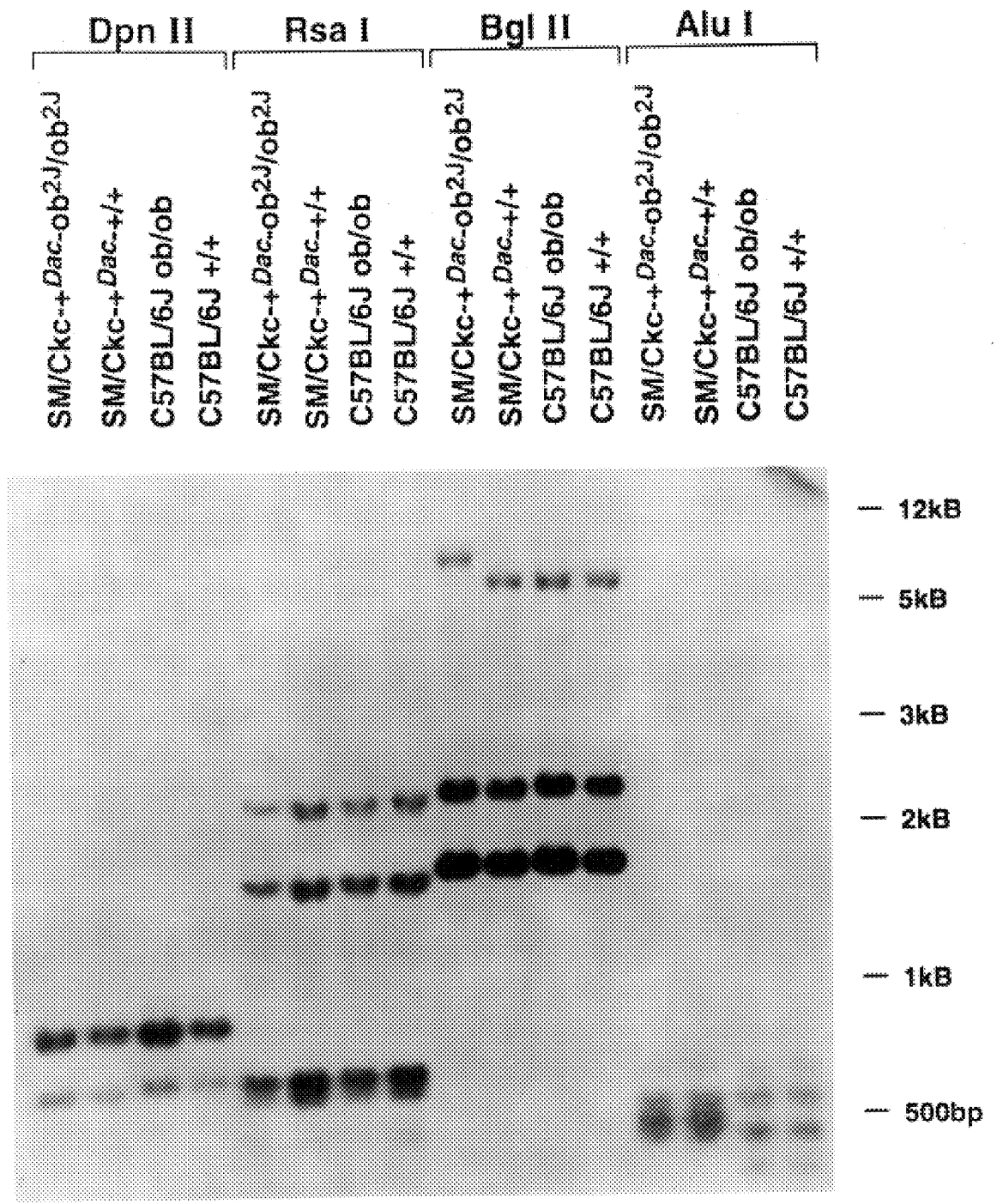
FIGS. 15A–B. (A) Genomic southern blot of genomic DNA from each of the mouse strains listed. Approximately 5 μg of DNA (derived from genomic DNA prepared from liver, kidney or spleen) was restriction digested with the restriction enzyme indicated. The DNA was then electrophoresed in a 1% agarose TBE gel and probed with PCR labeled 2G7. Restriction digestion with BglII revealed an increase in the size of an approximately 9 kB (the largest) BglII fragment in SM/Ckc-+Dacob$^{2J}$/ob$^{2J}$ (2J) DNA. RFLPs were not detectable with any other restriction enzymes. Preliminary restriction mapping of genomic DNA indicated that the polymorphic BglII site is about 7 kB upstream of the transcription start site. None of the other enzymes tested extend past the mRNA start site. (B) Segregation of a BglII polymorphism in the SM/Ckc-+Dacob$^{2J}$/ob$^{2J}$ strain. Six obese and five lean progeny from the same generation of the coisogenic SM/Ckc-+$^{Dac}$ob$^{2J}$/ob$^{2J}$ (2J) colony were genotyped by scoring the BglII polymorphism as shown in (A). All of the phenotypically obese animals were homozygous for the larger allele of the polymorphic Bgl fragment. The DNA in the "control" lane was prepared from an unrelated SM/Ckc-+$^{Dac}$+/+ mouse, bred separately from the SM/Ckc-+$^{Dac}$ob$^{2J}$/ob$^{2J}$ colony.

A genomic Southern blot of DNA from the CKC/smj (SM/Ckc-+$^{Dac}$) and C57BL/6J mice using four different restriction endonucleases was performed in order to determine whether the mutant ob yielded a unique fragment pattern (FIG. 15A). Approximately 10 μg of DNA (derived from genomic DNA prepared from liver, kidney, or spleen) was restriction digested with the restriction enzyme indicated. The DNA was then electrophoresed in a 1% agarose TBE gel. The DNA was transferred to an imobilon membrane and hybridized to the PCR labeled 2G7 probe. The key band is the uppermost band in the BglII digest for the CKC/smj ob/ob (SM/Ckc-+$^{DAC}$ob$^{2J}$/ob$^{2J}$) DNA. This band is of higher molecular weight than in the other strain, indicating a mutation in this strain.

Figure 15B:
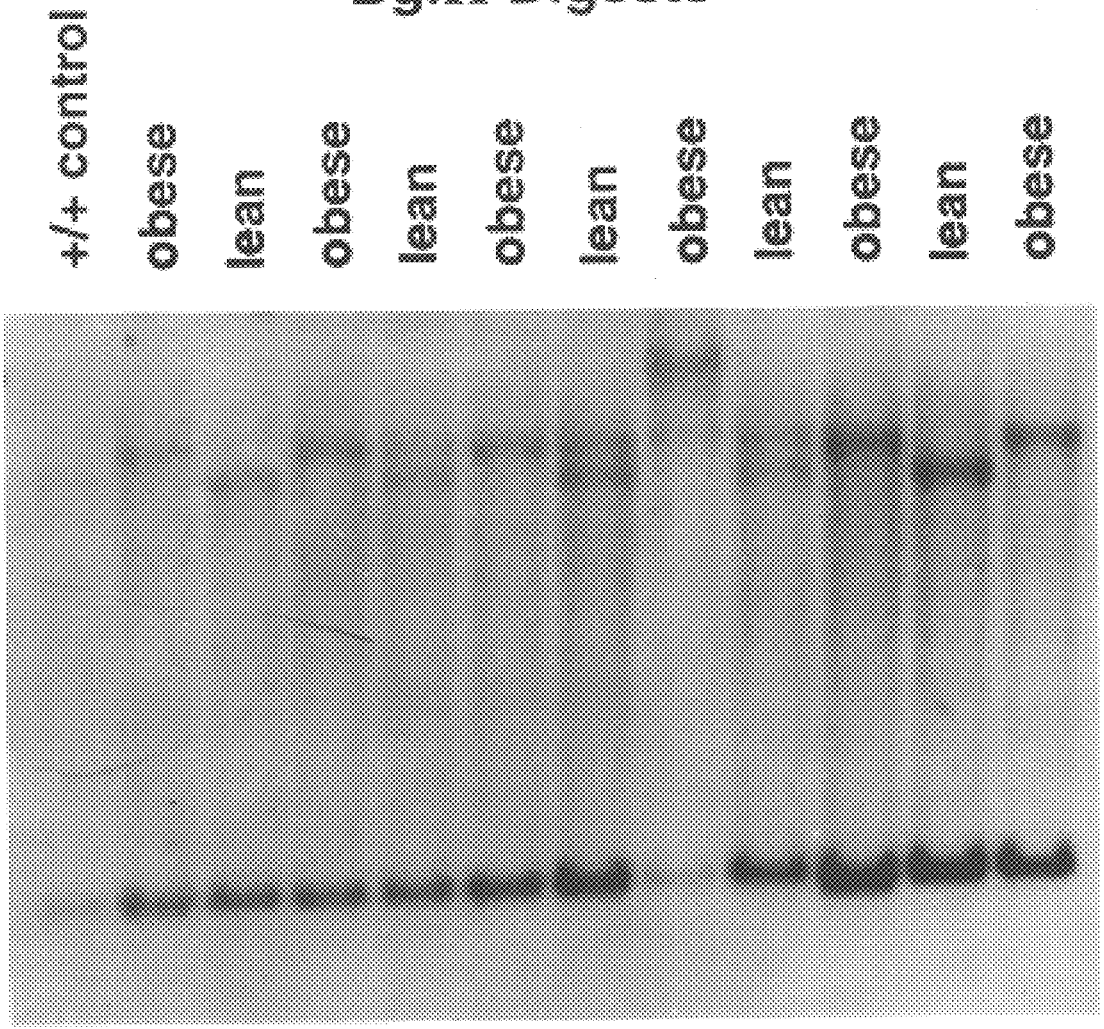

FIG. 15B is a southern blot of a BglII digest of genomic DNA from the progeny of an ob$^{2J}$/+×ob$^{2J}$/+ cross. Some of the DNAs have only the upper band, some only the lower band, and some have the both bands. The animals with only the upper band are allo-obese, i.e., ob$^{2J}$/ob$^{2J}$. These data show that the polymorphism (i.e., mutation) shown in FIG. 15A segregates in a genetic sense.

cDNA Cloning and Sequence Determination of ob

Using the labeled 2G7 PCR probe, a total of 50 mouse cDNA clones from a murine fat cell λgt11 cDNA library (Clonetech 5'-STRETCH cDNA from testicular fat pads of Swiss mice, #ML3005b), and thirty cross hybridizing human cDNA clones from a human fat cell λgt10 cDNA library (Clonetech 5'-STRETCH cDNA from abdomen #HL1108a) were isolated. Library screening was performed using the plaque lift procedure. The filters from the plaque lift were denatured using the autoclave method. The filters were hybridized in duplicate with the PCR labeled 2G7 probe (Rapid Hybe buffer, 65° C., overnight). After a 2–4 hour prehybridization, the filters were washed in 2× SSC, 2% SDS, twice for 30 minutes at 65° C. and exposed to SRy Llim. Duplicate positives were plaque purified. Plaque purified phage were PCR amplified using commercially available vector primers, e.g., λgt10 and λgt11. The resulting PCR products corresponded to the cDNA insert for each phage with a small amount of vector sequence at either end. The bands were gel purified and sequenced using the ABI automated sequencer and the vector primers to probe the DNA polymerase.

The raw sequencing data were then manually examined base by base to correct mishearing from the computer program. As the correct sequence became available, the downstream primers were synthesized and used to continue sequencing. Such experiments were repeated until each available cDNA clone was sequenced and synthesized into a contig. To date, ~3000 base pairs from the 5' end of the mRNA has been compiled. One of the cDNA clones extended to the 5' end of the mRNA since its sequence was identical to that of the 5' RACE product of fat tissue RNA (data not shown).

The sequence data revealed that there is a 167 amino acid open reading frame (FIG. 1). A Kozak translation initiation consensus sequence was present with an adenosine residue three bases upstream of the ATG. Two classes of cDNA were found differing by inclusion or exclusion of a single glutamine codon. This residue is found in a position immediately 3' to the splice acceptor of the 2G7 exon. Since the CAG codon of glutamine includes a possible AG splice acceptor sequence, it appears that there is slippage at the splice acceptor site with an apparent 3 base pairs deletion in a subset of the cDNA, as shown below.

```
         gln ser val
      ag CAG TCG GTA (with glutamine)      (SEQ ID NO:16)
      ↑
(splice acceptor site)

ser val
      ag CAG TCG GTA (without glutamine)   (SEQ ID NO:17)
      ↑
(splice acceptor site)
```

The "ag" in the sequences above corresponds to the assumed intron sequence upstream of the glutamine codon, and AG is the putative alternative splice site. This glutamine residue is located in a highly conserved region of the molecule and its importance for biological activity is as yet unknown.

A putative N-terminal signal sequence was detected, the signal cleavage site of which is predicted to be carboxy terminal to the alanine residue at amino acid position 21. This putative signal sequence was confirmed by application of a computer algorithm to the method of von Heijne (*Nucl. Acids Res.* 14, 4683, 1986). Using this technique, the most probable signal sequence was identified in the polypeptide coding region corresponding to amino acids 1–23, having the sequence:

MCWRPLCRFLWLWSYLSYVQA ↑ VP (SEQ ID NO:10)

in which the arrow indicates the putative signal sequence cleavage site. The rest of the amino acid sequence was largely hydrophilic and did not have any notable structural motifs or membrane spanning domains other than the N-terminal signal sequence. Specifically, we did not find consensus sequences for N-linked glycosylation or dibase amino acid sequences indicative of protein cleavage in the predicted processed protein (Sabatini and Adesnik, *The metabolic basis of inherited disease*, C. V. Scriver et al. eds., McGraw-Hill: New York, pp. 177–223). Data base search using Blast and Block programs did not identify any homologous sequence.

Human fat tissue RNA was analyzed on Northern blot, RNA species of similar size to the mouse ob gene was detected. Sequencing and analysis of cDNA clones revealed that human ob also encodes 167 amino acid polypeptide (FIGS. 2 and 3). Two classes of cDNA with or without three base pairs deletion were found in human as well (FIG. 6). The mouse and human ob genes were highly homologous in the predicted coding region, but had only 30% homology in the available 3' and 5' untranslated regions. An N-terminal signal sequence was also present in the human ob polypeptide. Comparison of the human and mouse ob polypeptide sequences showed that the two molecules share an overall 83% identity at amino acid level (FIG. 4). The N-termini of the mature proteins from both species share even higher homology, with only six conservative and six nonconservative amino acid substitutions among the N-terminal 100 amino acid residues.

Figure 16:
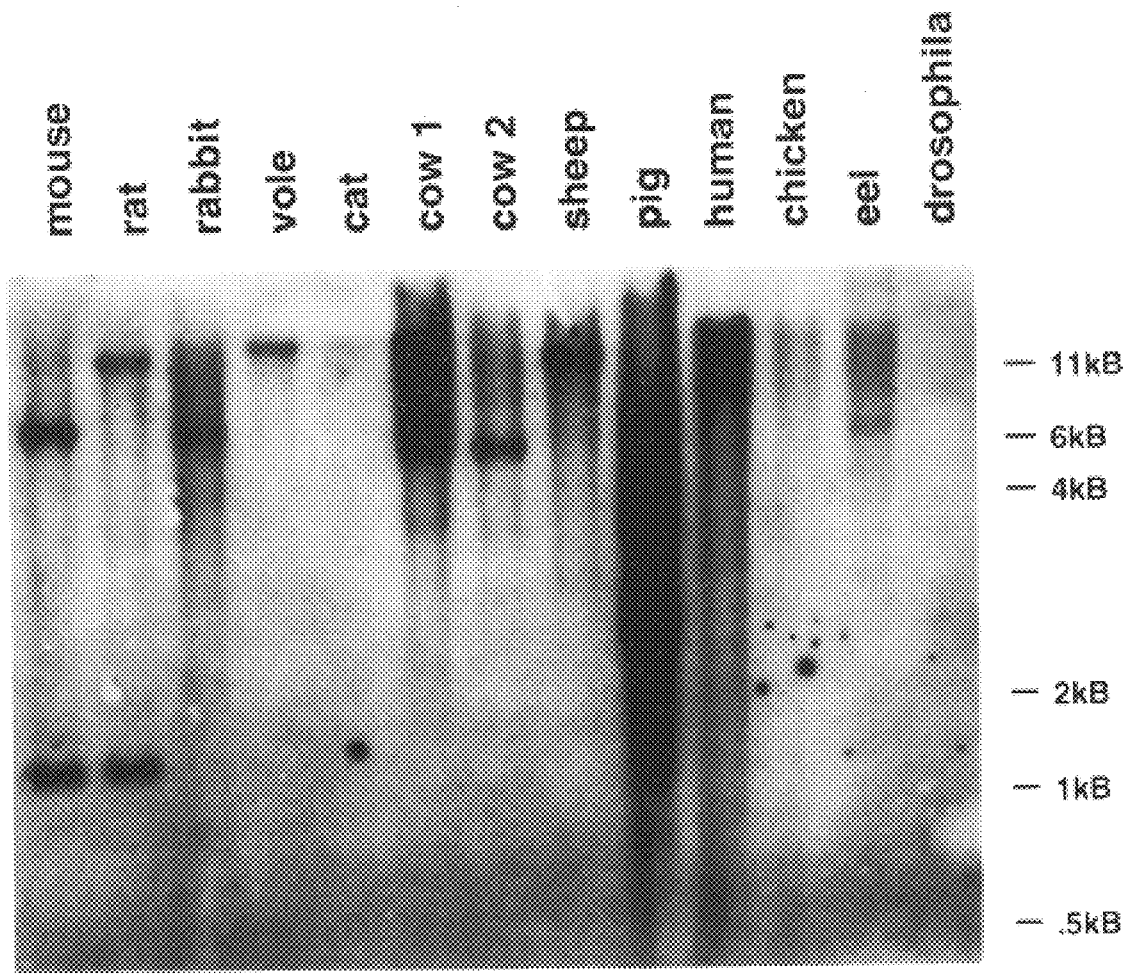
FIG. 16 is a Southern blot of EcoRI digested genomic DNA from the species listed, using an ob cDNA as a probe (i.e., a zoo blot). Hybridization signals were detectable in every vertebrate sample, even after a moderate stringency hybridization. The cat DNA in this experiment was slightly degraded. The restricted DNA was run on a 1% agarose TBE gel, and transferred to an imobilon membrane for probing. The filter was hybridized at 65° C. and washed in 2× SSC/0.2% SDS at 65° C. twice for twenty minutes and exposed for 3 days using Kodak X-OMAT film.

Genomic DNA was isolated from mouse, rat, rabbit, vole, cat, cow, sheep, pig, human, chicken, eel, and drosophila, and restriction digested with EcoR1. The digests were electrophoresed on 1% agarose TBE gel. DNA was transferred to an imobilon membrane and probed with the PCR labeled 2G7 probe. The filter was hybridized at 65° C. and washed with 2× SSC, 0.2% SDS at 65° C. twice for twenty minutes each wash, i.e., there were two buffer changes. These data indicate that ob is conserved among vertebrates (FIG. 16). Note in this regard that there is a 2+ signal in eel DNA; eel is a fish.

In summary, available evidence suggests that body weight and adiposity are physiologically controlled. Seven years ago efforts began to identify two of the key components of this system: the ob and db genes. As shown in this example, the ob gene has now been identified as a fat specific gene that plays a key role in regulating body weight. The product of this gene, which is most probably a secreted hormone, will have important implications for the diagnosis and treatment of nutritional disorders in man and non-human animals.

EXAMPLE

Expression of ob In Bacteria

Both murine and human cDNAs encoding ob have been cloned into a pET-15b expression vector (Novagen). This vector contains a T7 promoter in conjunction with a lac operator, and expresses a fusion protein containing a histidine tag (His-Tag) and a thrombin cleavage site immediately upstream of the coding sequence insertion site (FIG. 17) (SEQ ID No:11).

The mouse and human cDNAs were modified such that the alanine at the end of the signal sequence was turned into an NdeI site, as was a separate sequence in the 3' region. Insertion of the NdeI site was accomplished using PCR with novel primers:

Mnde-5' (murine five prime primer):
   CTTATGTTCA TATGGTGCCG ATCCAGAAAG TC
   (SEQ ID NO:12)
Mnde-3' (murine three prime primer):
   TCCCTCTACA TATGTCTTGG GAGCCTGGTG GC
   (SEQ ID NO:13)
Hnde-5' (human five prime primer):
   TCTATGTCCA TATGGTGCCG ATCCAAAAAG TC
   (SEQ ID NO:14)
Hnde-3' (human three prime primer):
   TTCCTTCCCA TATGGTACTC CTTGCAGGAA GA
   (SEQ ID NO:15)

The primers contain a 6-base pair mismatch in the middle that introduces NdeI restriction sites at each end of the PCR fragment. Phage carrying either the mouse or human cDNA were PCR amplified using those primers. The PCR product was digested with NdeI and gel purified on a 1% low melting point agarose gel. The gel purified bands were subcloned into the pET vector. The resulting plasmids were sequenced to ensure that mutations were not introduced during the PCR amplification step of cloning. Constructs for the human and murine cDNA that encodes and that lacks glutamine 49 have been prepared. In particular, pET 15b constructs containing either the human or the mouse ob coding sequence, minus signal sequence and fused to a Hig-Tag, have been made using a PCR cloning method. The constructs have been sequenced to ensure no sequence errors were introduced into the coding region of the ob gene during the PCR amplification step.

Figure 18A:
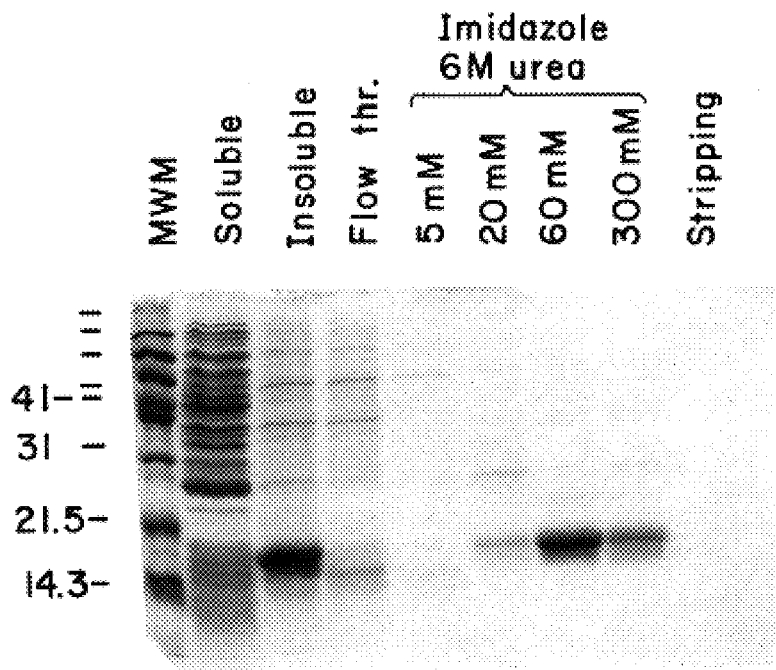
FIGS. 18A–B presents analysis of the eluate from a His-binding resin (Ni) column for a recombinant mature murine ob fusion to a His-tag (A) and mature human ob fusion to a His-tag (B). Bacteria transformed with vectors pETM9 and pETH14, respectively. Upon induction with 1 mM IPTG at optimal conditions, the transformed bacteria were able to produce 100–300 μg/ml of ob fusion protein, primarily in the inclusion body. The inclusion body was solubilized with 6M guanidine-HCl or urea, and fusion protein (present in the lysis supernatant) was loaded on the His-binding resin (Ni) column in 10 ml of 1× binding buffer with urea. The column was eluted stepwise with 5 ml aliquots of 20 μM, 60 μM, and 300 μM imidazole, and finally with strip buffer. The aliquots were analyzed for the presence of ob polypeptide fusion on a 15% acrylamide gel. Each lane contains the equivalent of 100 μl of bacterial extract.
Figure 18B:
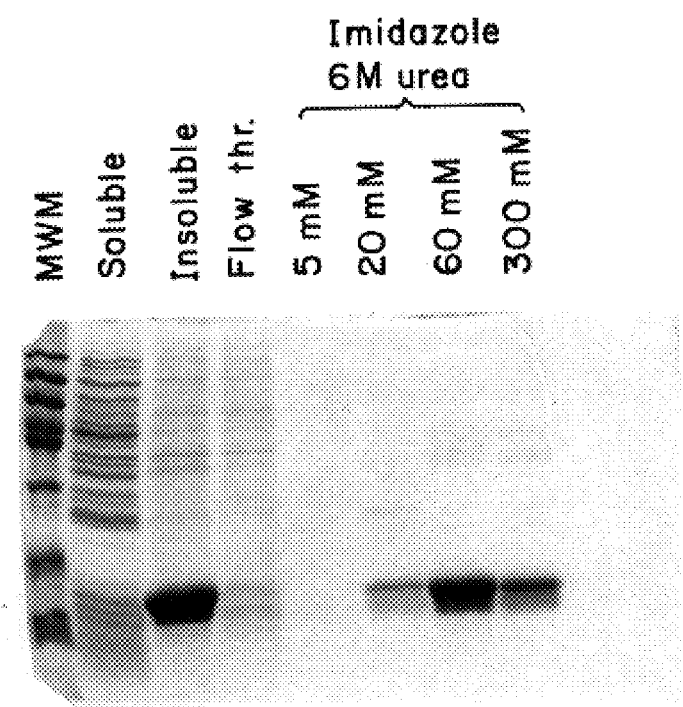

Two resultant plasmid constructs, pETM9 and pETH14, were selected to transform a bacterial expression host. Upon induction with 1 mM IPTG under optimal conditions, the transformed bacteria were able to produce 100–300 μg/ml of the ob fusion. The majority of the ob fusion protein was found in the inclusion body. After solubilization with 6M guanidine-HCl or urea, the fusion protein was purified through a His-binding (Ni-chelation) resin column. The conditions for column purification of the ob fusion protein (including binding, washing, and eluting) were established experimentally. The ob fusion protein binds to the resin at 5 mM imidazol/6M guanidine-HCl and stays bound at up to 20 mM imidazol/6M guanidine-HCl. The protein can be eluted form the resin at 60 mM imidazol/6M guanidine (FIGS. 18A,B). Both the purified human and mouse ob fusion proteins were further dialyzed in PBS to remove guanidine-HCl from the preparation and used to raise polyclonal antibodies.

In order to test the biological activity of the fusion protein products, the refolding conditions for the purified protein was tested and developed. This involves initial dialysis of the fusion protein in 1M guanidine solution, followed by dilution with 0.4M arginine solution. The His-Tag was removed from the fusion proteins before biological function assay. The tag removal was achieved by treating the fusion protein with thrombin from human placenta.

In addition, human and mouse ob gene coding sequence minus the signal sequence is being inserted into a pET 12c vector using PCR cloning method. These constructs can direct the synthesized ob fusion proteins into the periplasmic space of the bacterial host cell. The ob fusion protein recovered from the periplasmic space may only need a simple gel filtration to be purified from other host proteins and will not be denatured during such process.

EXAMPLE

Preparation of Antibodies to the ob Polypeptide

In addition to use of the recombinant protein to generate polyclonal antibodies, a set of four peptide sequences from the deduced murine ob sequence were identified using immunogenicity plot software (GCG Package). The four carboxyl terminal peptide fragments are:

(SEQ ID NO:18):
   Val-Pro-Ile-Gln-Lys-Val-Gln-Asp-Asp-Thr-Lys-Thr-Leu-Ile-Lys-Thr
(SEQ ID NO:19):
   Leu-His-Pro-Ile-Leu-Ser-Leu-Ser-Lys-Met-Asp-Gln-Thr-Leu-Ala
(SEQ ID NO:20):
   Ser-Lys-Ser-Cys-Ser-Leu-Pro-Gln-Thr-Ser-Gly-Leu-Gln-Lys-Pro-Glu-Ser-Leu-Asp
(SEQ ID NO:21):
   Ser-Arg-Leu-Gln-Gly-Ser-Leu-Gln-Asp-Ile-Leu-Gln-Gln-Leu-Asp-Val-Ser-Pro-Glu-Cys

These peptides were conjugated to KLH, and the peptide-KLH conjugates were used to immunize rabbits using standard techniques. Polyclonal antisera specific for each peptide is recovered from the rabbits.

EXAMPLE

In Vitro Translocation of an ob Polypeptide

Figure 19A:
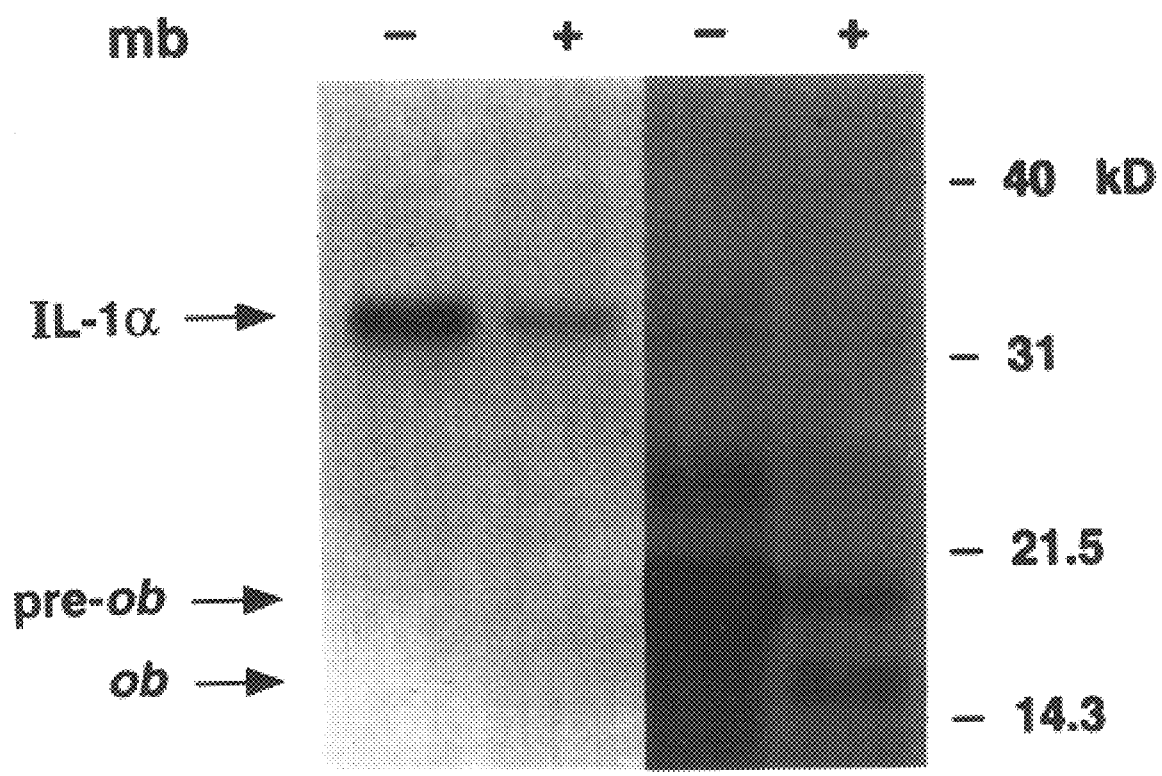
FIGS. 19A–B. (A) In vitro translation of ob RNA. A human ob cDNA was subcloned into the pGEM vector. The plasmid was linearized and plus strand RNA was synthesized using sp6 polymerase. The in vitro synthesized RNA was translated in the presence or absence of canine pancreatic microsomal membranes. An approximately 18 kD primary translation product was seen after in vitro translation. The addition of microsomal membranes to the reaction led to the appearance of a second translation product about 2 kD smaller than the primary translation product. The size of the translation product of interleukin-1α RNA, which lacks an encoded signal sequence, was unchanged by the addition of microsomal membranes. These data indicated the presence of a functional signal sequence. (B) In vitro translation in the presence or absence of proteinase K. Protease treatment resulted in complete proteolysis of the 18 kD primary translation product, while the 16 kD processed form was unaffected. Permeabilization of the microsome with 0.1% TRITON-X100 rendered the processed from protease sensitive. These results indicate that the product had translated into the lumen of the microsome.
Figure 19B:
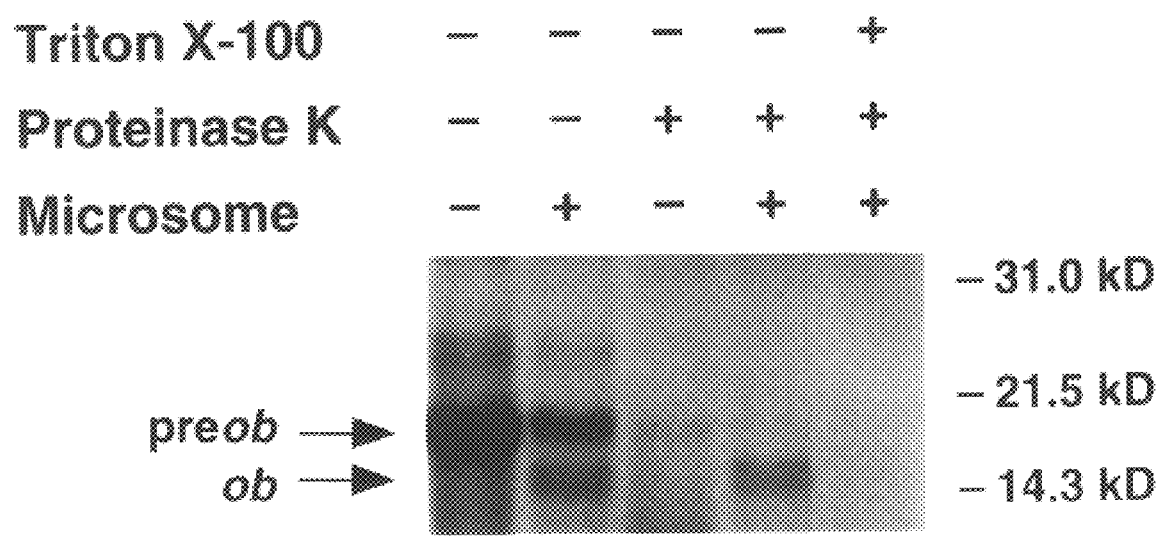

In order to confirm the presence of a functional signal sequence, a human cDNA that included the entire open reading frame was subcloned into the pGEM vector. Only the human cDNA was used in this experiment because suitable mouse subclones were not recovered. Positive strand human ob RNA was transcribed using sp6 polymerase and used in an in vitro translation reaction with and without canine pancreatic microsomal membranes. The primary translation product migrated with an apparent molecular weight of ~18 kD, which is consistent with that predicted by the cDNA sequence. Inclusion of the microsomal membranes in the reaction inhibited the overall efficiency of translation ~5 fold. Nevertheless, approximately 50–70% of the ob primary translation product was truncated by approximately 2 kD in the presence of the membrane preparation, suggesting that the signal sequence is functional (FIG. 19A). The size of the primary translation product of interleukin-1α RNA, which does not encode a signal sequence, was unchanged when microsomal membranes were included in the reaction. In order to confirm that translocation of the ob protein had taken place, the in vitro translation products were treated with Proteinase-K. Protease treatment resulted in the complete proteolysis of the 18 kD primary translation product while the 16 kD processed form was unaffected by the enzyme treatment, indicating that it had translocated into the lumen of the microsomes (FIG. 19B). These data are compatible with the hypothesis that ob is a secreted molecule.

After signal sequence cleavage, two cysteine residues would remain within the predicted protein raising the possibility that the molecule contains a disulfide bond characteristic of other secreted polypeptides (Shen and Rutter, 1984, Science 224:168–171).

EXAMPLE

Characterization of the ob Gene

To establish the relationship between obesity and genetic alterations in the ob gene in humans, the sequence of the human ob gene was determined (FIG. 20A) (SEQ ID NO: ). Specific primers from the human coding sequence were used to screen a human P1 library. Three different P1 clones were obtained, grown up, and PCR amplified using primers flanking the splicing site between the first and second coding exon. The entire intron region, around 2 kB, was amplified and partially sequenced (see FIG. 20A; and as indicated in SEQ ID NO:22).

The gene structure of both the murine and human genes was characterized using PCR assays and other standard techniques. The mouse ob gene was found to consist of 3 exons, the second and third of which account for the coding sequence (FIG. 20B). The coding region of the human ob gene shares the same structure; however, the human gene lacks a 5' exon and intron (FIG. 20C).

Figure 20A:
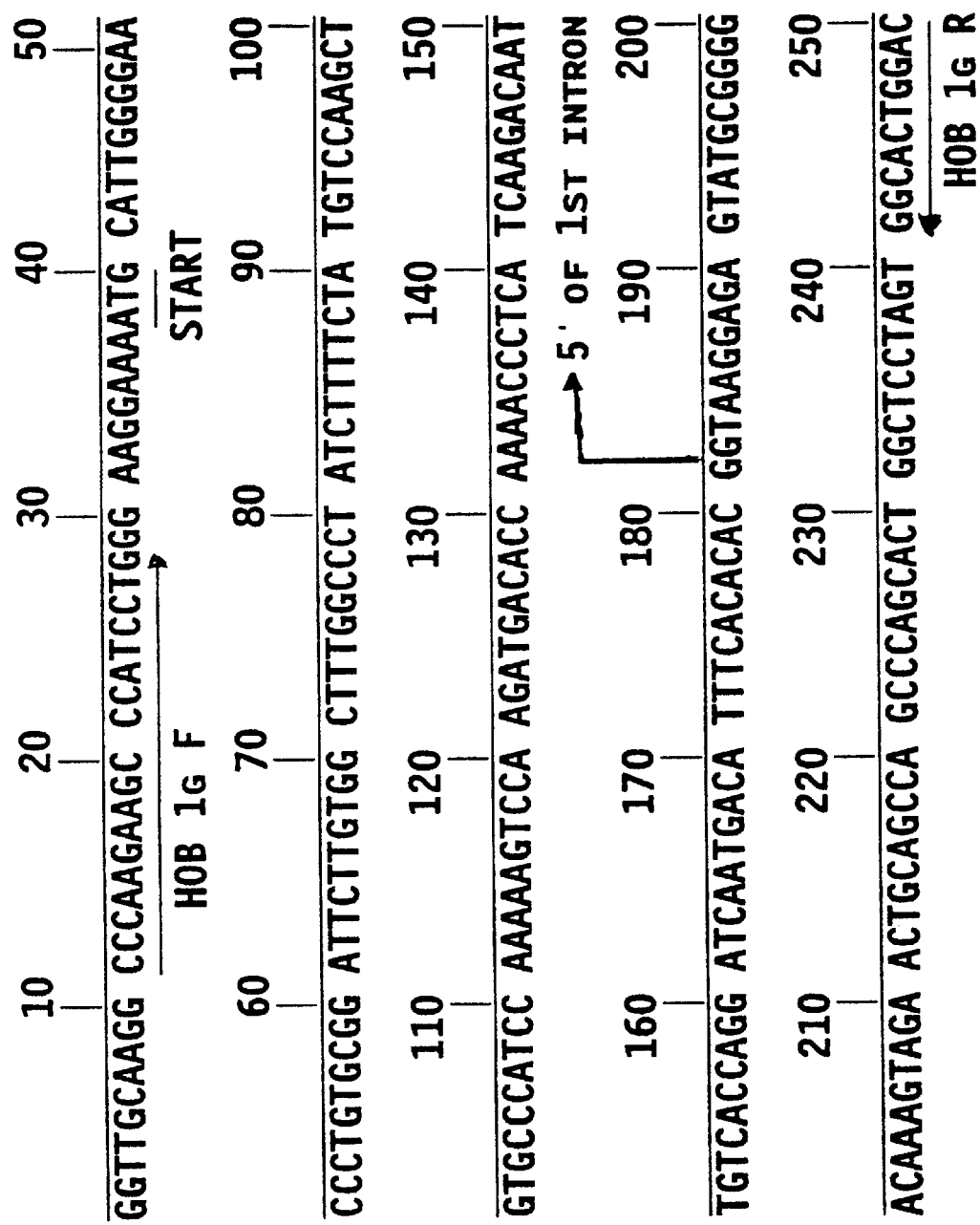
FIGS. 20A–C. (A) The sequence of the human ob gene (SEQ ID NO:22 to SEQ ID NO:25). (B) A schematic diagram of the murine ob gene. (C) A schematic diagram of the human ob gene. In both (B) and (C), the start and stop codons are underlined. There is no evidence of a first intron homologous to the mouse first intron in the human gene, but its existence cannot be excluded.
Figure 20B:
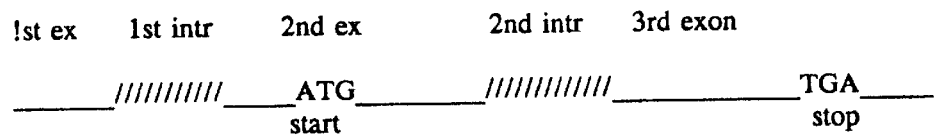
Figure 20C:
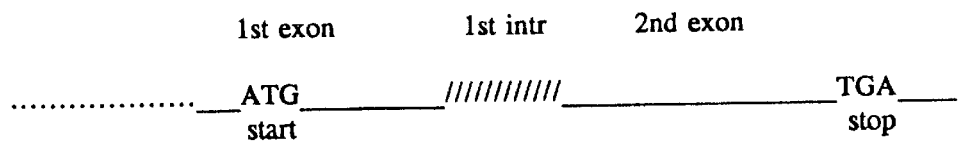

Two sets of primers generated from the intronic sequences of the human gene have been prepared (FIG. 20A). The sequences of the primers follows (F and R refer to forward and reverse, respectively):

HOB 1gF 5'-CCCAAGAAGCCCATCCTG-3' (SEQ ID NO:29)
HOB 1gR 5'-GACTATCTGGGTCCAGTGCC-3' (SEQ ID NO:30)
HOB 2gF 5'-CCACATGCTGAGCACTTGTT-3' (SEQ ID NO:31)
HOB 2gR 5'-CTTCAATCCTGGAGATACCTGG-3' (SEQ ID NO:32)

DNA samples have been obtained from various sources, and these sets of primers are being used to amplify human genomic DNA from severely obese people. The PCR products were run on a low melting point agarose gel, and the bands were cut out and digested with agarase. The sequences were obtained using the ABI 373A DNA sequencer and Taq dideoxy terminator kit (abi, Perkin-Elmer). One point mutation in an ob gene from a patient sample has been detected to date. This mutation is on the first exon and does not change the amino acid sequence. Preliminary data indicate that an insertion sequence may be present in the first exon of another patient.

A different automated sequencing method with Sequenase instead of Taq DNA polymerase may be employed to yield more easily readable sequences for mutation detection.

EXAMPLE

Expression of ob in Yeast

Following the positional cloning of ob, it became important to uncover the physiological mechanism by which the ob protein reduces food intake and body weight. The first step in this direction was to recombinantly produce a functional protein using an expression system. In addition to the successful bacterial expression system, a yeast expression system was also selected. Yeast expression has several attractive features for expressing ob. The most important is that biologically active eukaryotic proteins are more likely to be produced. The ob polypeptide is secreted by mammalian cells. Protein secretion is very similar for all eukaryotes, which means that the yeast secretory apparatus is much more similar to the mammalian secretory pathway than bacterial secretory pathways would be. In particular, protein modifications of ob seen in mammalian cells would likely also be seen in the expression through the yeast secretory system. In addition, protein folding is carried out in passage through the secretory apparatus and thus delivering ob through the yeast secretory apparatus is likely to give a properly folded protein with native biological activity. This is significant for ob because the two cystein residues may form a disulfide bridge. In contrast to secretory pathways, the reducing environment of the cell cytoplasm prevents formation of disulfide bridges, and therefore it is essential that ob pass through the secretory pathway in order for this disulfide bond to form in vivo. Other advantages have to do with the ease and quickness of manipulating yeast, the availability of vectors and strains, and the vast experience in yeast recombinant technology.

Figure 21A:
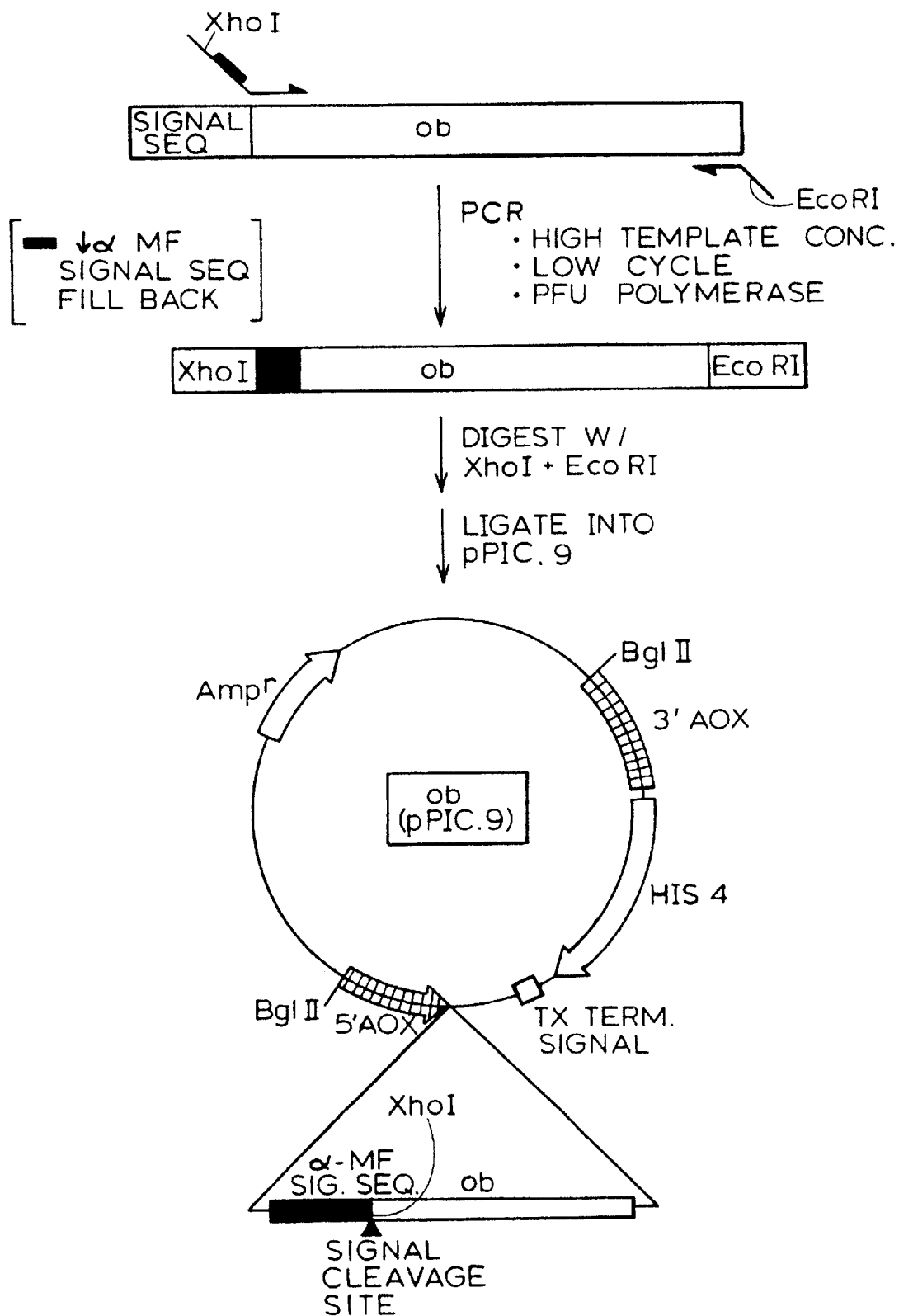
FIGS. 21A–C. presents a schematic drawing of one of the cloning strategies employed to achieve recombinant expression of ob in pichia yeast. (A) Expression vector of ob with an α-mating factor signal sequence. (B) Schematic drawing of the structure of the recombinant fusion protein, including the amino acid sequence (SEQ ID NO:23) showing the XhoI site and putative KEX-2 and STE-13 cleavage sites, and the N-terminal surplus amino acids present after KEX-2 cleavage (SEQ ID NO:24). (C) An alternative strategy for producing mature ob under involves preparing a construct with an amino acid sequence corresponding to a XhoI cleavage site and a KEX-2 cleavage site immediately upstream of the mature ob polypeptide sequence (SEQ ID NO:25).
Figure 21B:
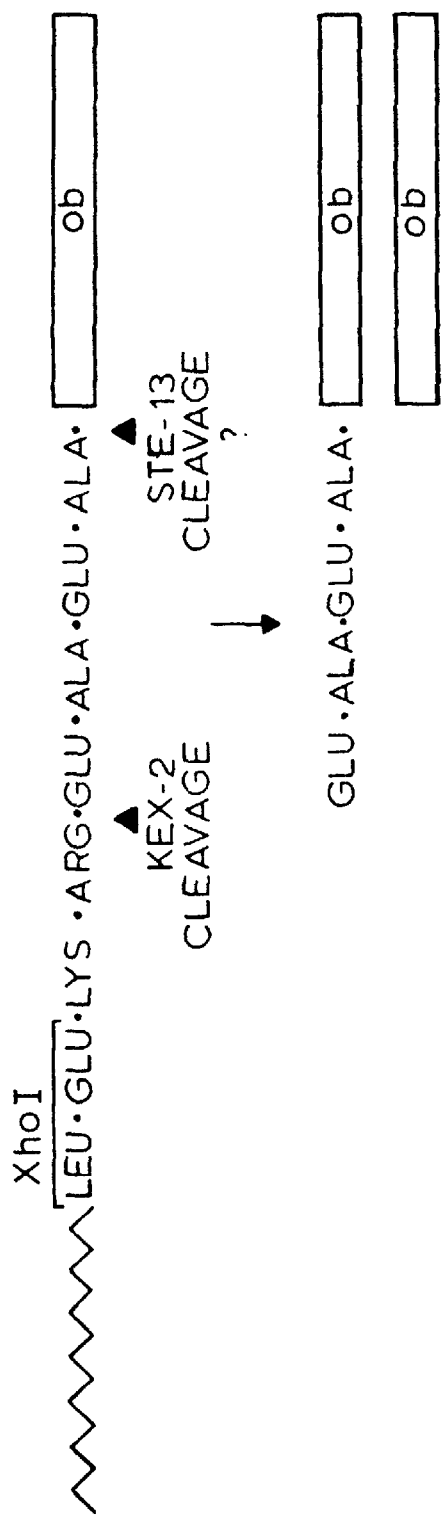
Figure 21C:

A *Pichia pastoris* expression system was chosen for four reasons: (1) it has higher levels of heterologous protein expression than other yeast systems such as *S. cerevisiae*; (2) protein glycosylation is more similar to the mammalian system in *P. pastoris* than *S. cerevisiae* (although glycosylation sites were not detected in ob using a computer search, there still remained the possibility of glycosylation at unrecognized sites); (3) *P. pastoris* secretes very few proteins natively, and thus it is generally straightforward to purify the expressed foreign protein; and (4) the vectors and yeast strains are commercially available (from Invitrogen). Two strategies for generating yeast expression vectors are shown in FIGS. 21 and 22.

The vector chosen was pPIC.9. This vector contains a cloning site just downstream of the alpha-mating factor prepro coding sequence which directs the protein encoded by the gene cloned into the cloning site to be secreted by the secretory pathway. The other important feature of the vector is a HIS4 gene that allows selection for uptake of the vector using a yeast auxotrophic strain grown on histidine-deficient media following transformation of the yeast with the vector. The cloning strategy was the following: PCR amplify ob cDNA using a 5' primer that contained at its 3' end sequence complementary to the sequence of ob just following the predicted leader peptide cleavage site, and at its most 5' end a sequence complementary to the 3' end of the alpha-mating factor sequence of the vector. The 5' primer also contains an XhoI site. The 3' primer was designed to have at its 3' end a sequence complementary to the last few amino acids of ob and an EcoRI site at its 5' end. Following PCR amplification, the PCR product was digested with XhoI and EcoRI and cloned into similarly digested pPIC.9. Following the cloning of both the mouse and human ob cDNAs, each with and without the glutamine at codon 49, individual clones were isolated for all four individual constructs and sequenced to verify that the constructs were cloned in the correct orientation and frame and contained no mutations from the PCR amplification step. Following identification of clones with the correct sequence, these were transformed into *P. pastoris* strain GS115, a histidine auxotroph.

Figure 23A:
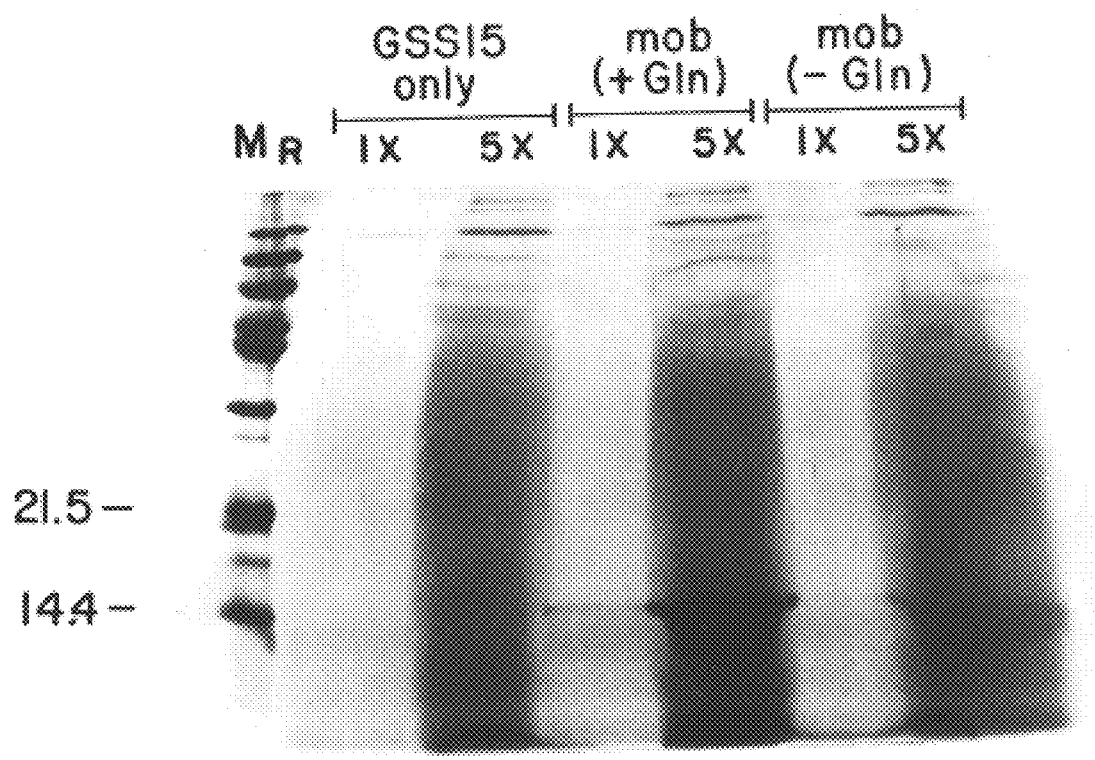
FIGS. 23A–B. (A) PAGE analysis of expression of murine ob (both the microheterogenous forms, i.e., containing and missing Gln 49) in transformed pichia yeast. The expected band of approximately 16 kD is visible in the transformed yeast culture fluid (second and third lanes), but not in culture fluid from non-transformed yeast (first lane). (B) PAGE analysis of partially purified recombinant ob polypeptide on carboxymethyl cellulose, a weak cation exchanger. A band of about 16 kD is very visible in fractions 3 and 4 from the column, which was eluted with 250 mM NaCl. Lane 1—loaded sample; lane 2—flow through; lanes 3–5—fractions eluted with 250 mM NaCl.
Figure 23B:
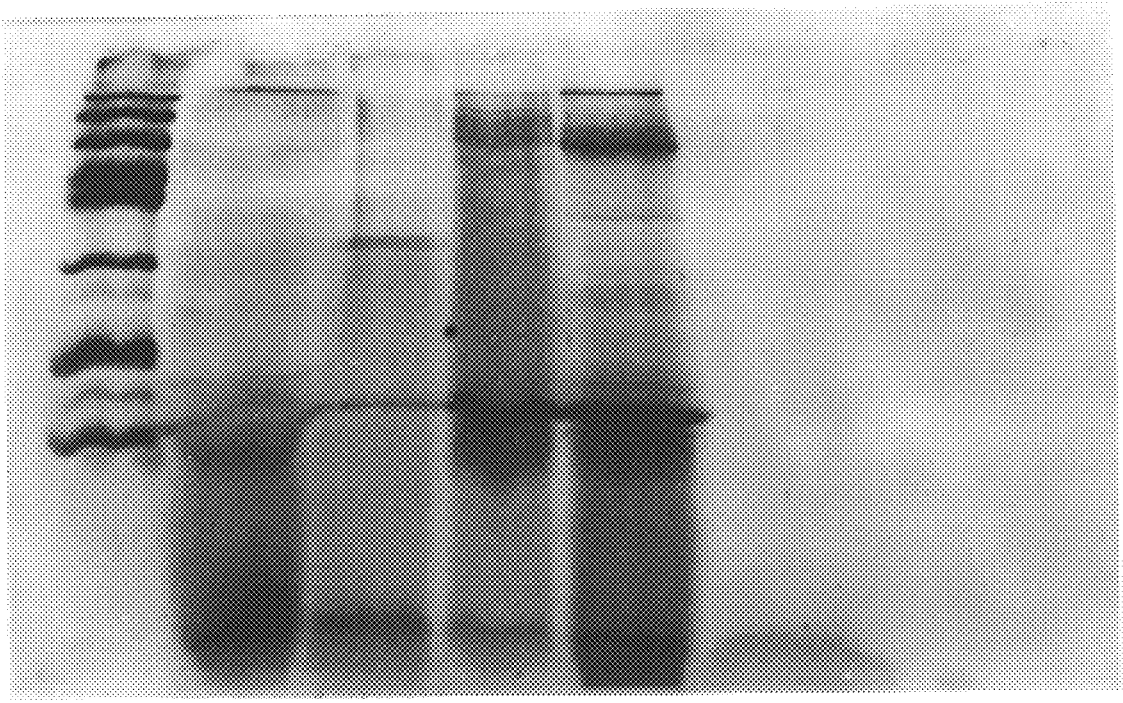

For the two mouse ob constructs, transformed yeast clones were screened for protein expression. As evidence that the transformed yeast contain ob, a DNA dot-blot assay and a colony hybridization assay were done which both showed ob sequence within the transformed yeast but not within the untransformed yeast. Furthermore, the transformed yeast now secreted a 16 kDa protein into the culture media whereas the untransformed yeast does not secrete a protein of this size (FIG. 23A). This is the predicted size of ob. Individual clones for both mouse constructs have been identified that are high expressors for ob, and currently a purification strategy is being developed to purify ob to homogeneity. One strategy has been to purify ob on a cation exchange column (FIG. 23B); preliminary data suggest that a strong cation exchanger may be useful. However, after cation exchange chromatography, the putative ob product is lost. This indicates the presence of a protease in the sample.

Figure 22A:
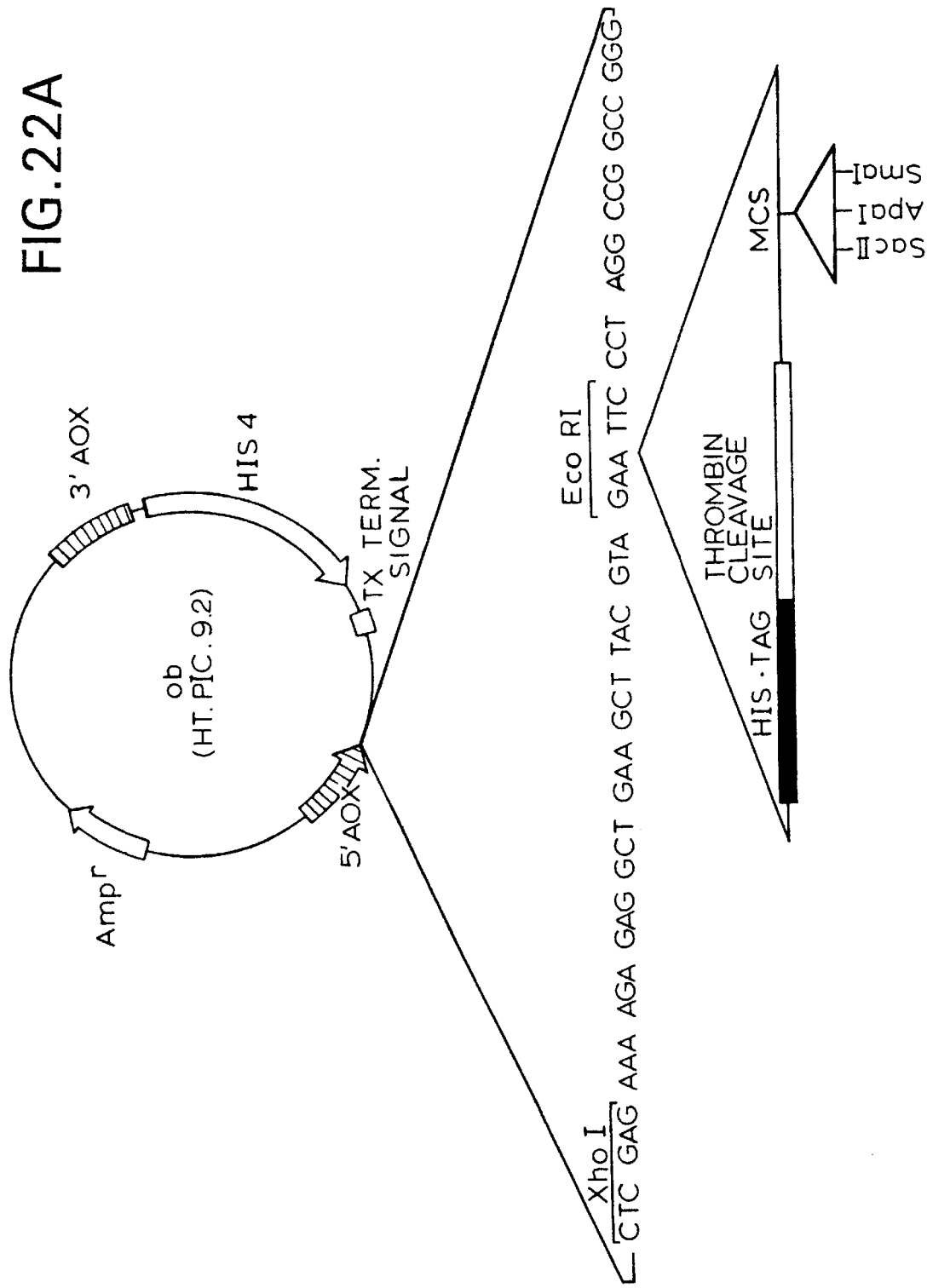
FIGS. 22A–B. Alternative expression strategy in pichia. (A) Expression vector of an ob fusion with a His tag adopted from the pET expression system under control of the α-mating factor signal sequence. (B) Schematic drawing of the structure of the recombinant ob fusion protein containing a His tag, which includes the α-mating mating factor signal sequence, putative KEX-2 and STE-13 cleavage sites, the Histag, and a thrombin cleavage site, and which would yield ob with three surplus N-terminal amino acid residues.
Figure 22B:
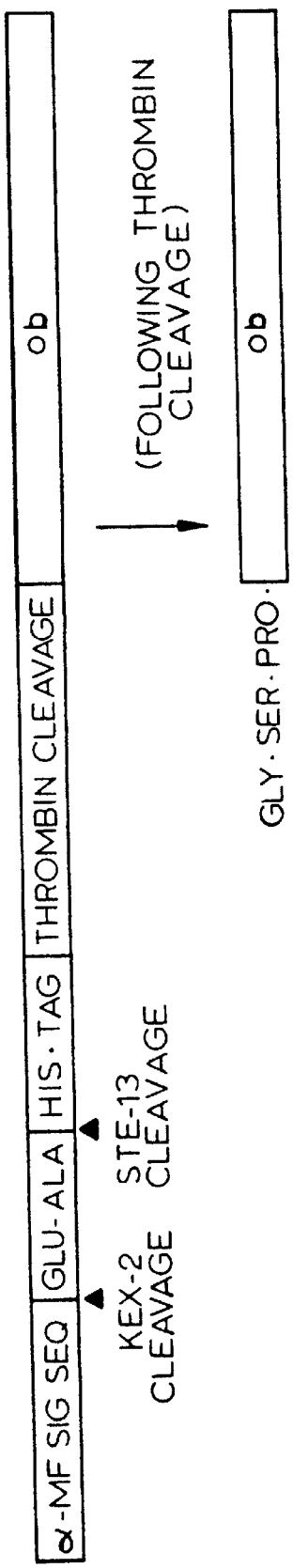

One strategy to overcome this problem is to prepare ob-His tag fusions for expression in yeast (FIG. 22). Further evaluation has demonstrated that ob without a His tag associates tightly with a Ni-chelation column. Purification of the ob polypeptide by Ni-chelation, followed by gel filtration, yielded a product of sufficient purity for mass spectral analysis. Mass spec confirms the molecular weight of the expressed protein is identical to the expected molecular weight, which strongly confirms that ob has been successfully expressed in Pichia.

However, the Ni-chelation/gel filtration purification protocol does not yield a ob polypeptide in sufficiently pure form. Additional small molecules are present. It does appear that the proteolytic activity elutes from the Ni-chelation column in the void volume. Accordingly, a three step purification process is planned: Ni-chelation, followed by cation exchange (which eliminates the small molecule contaminants), followed by gel filtration.

Estimating expression level by Coomassie blue staining of SDS-PAGE gels reveals approximately 10 mg/L when yeast are grown in shaker flasks. These levels are expected to increase in fermentation vessels, and we are about to initiate fermentation with the hopes of obtaining larger quantities of protein. Regarding the human ob constructs, transformed yeast clones containing high copy numbers of the ob gene have been identified, and these are expected to express ob protein. As antibodies are developed, these will be used to confirm the identity of the secreted 16 kDa protein.

Once purified the expressed protein is characterized by several methods. Physical characterization includes light-scattering to determine homogeneity of structure and is used as a measure of proper folding. Circular dichroism is used to roughly determine the structural geometry of the protein. Importantly, bioactivity of the purified protein is assayed by administering the protein to both elan and obese rodents via an osmotic pump (e.g., an ALZET osmotic pump from Alza Corporation, Palo Alto, Calif.) over at least a two-week period and observing effects on feeding behavior and body weight.

The following is a list of references related to the above disclosure and particularly to the experimental procedures and discussions.

Bahary, N.; G. Zorich; J. D. Pachter; R. L. Leibel; and J. M. Friedman. 1991. Molecular genetic linkage maps of mouse chromosomes 4 and 6. *Genomics* 11:33–47.

Bahary, N.; D. McGraw; R. L. Leibel; and J. M. Friedman. 1991. Chromosomal microdissection of midmouse chromosome 4: Mapping of microclones relative to the mouse db gene. Submitted.

Bahary, N.; J. Pachter; R. Felman; R. L. Leibel; K. A. Albright; S. Cram; and J. M. Friedman. 1991. Molecular mapping of mouse chromosomes 4 and 6: Use of a flow-sorted Robertsonian chromosome. Submitted.

Blank, R.; J. Eppig; F. T. Fiedorek; W. N. Frankel; J. M. Friedman; K. Huppi; I. Jackson; and B. Mock. 1991. Mouse chromosome 4. *Mammalian Genome* 1(suppl): s51–s78.

Bogardus, C. ; Ravussin, E.; Abbot, W.; Zasakzku, J. K.; Young, A.; Knowler, W. C. ; Friedman, J. M.; R. L. Leibel; N. Bahary; D. A. Siegel; and G. Truett, G. 1991. Genetic analysis of complex disorders: Molecular mapping of obesity genes in mice and humans. *Annals of the New York Academy of Sciences* 630:100–115.

Friedman, J. M.; R. L. Leibel; and N. Bahary. 1991. Molecular mapping of obesity genes. *Mammalian Genome* 1:130–144.

Friedman, J. M.; R.L. Leibel; N. Bahary; and G. Zorich. 1991. Molecular mapping of the mouse ob mutation. *Genomics*, (in press).

Harris, M. I. (1991). Diabetes Care 14 (suppl. 3), 639–648.

Harris, M. I.; Hadden, W. C. ; Knowler, W. C. ; and Bennett, P. H.(1987). Diabetes 36, 523–534.

Harris, R. B. S. (1990). FASEB J. 4, 3310–3318.

Jacobowitz, R., and Moll, P. O. (1986). N. Engl. J. Med. 315, 96–100

Kessey, R. E. (1980). In Obesity, A. Stunkard, eds. (Philadelphia: W. B. Sauders Co.), pp. 144–166.

Kessey, R. E., and Pawley, T. L. (1986). Annu. Rev. Psychol. 37, 109–133.22

Leibel, R. L., N. Bahary and J. M. Friedman. 1990. Genetic variation and nutrition in obesity: Approaches to the molecular genetics of obesity. In *Genetic variation and Nutrition* (Simopoulos, A. P. and Childs, B., eds.), S. Karger, Basel, pp. 90–101.

Siegel, D.; N. G. Irving; J. M. Friedman; and B. J. Wainwright. 1991. Localization of the cystic fibrosis transmembrane conductance regulator to mouse chromosome 6. *Cytogenetics Cell Genetics*, submitted.

Truett, G. E.; N. Bahary; J. M. Friedman; and R. L. Leibel. 1991. The rat obesity fatty (fa) maps to chromosome 5:Evidence for homology with the mouse gene diabetes (db). *Proc. Natl. Acad. Sci. USA* 88:7806–7809.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

---

---

What is claimed is:

1. An isolated polynucleotide encoding a mammalian OB polypeptide, said polypeptide capable of modulating body weight.

2. An isolated polynucleotide encoding an OB polypeptide capable of nodulating body weight, the polypeptide comprising:
    a) the amino acid sequence set out in SEQ ID NO: 2;
    b) the amino acid sequence set out in amino acids 22–167 of SEQ ID NO: 2;
    c) the amino acid sequence set out in SEQ ID NO: 4; or
    d) the amino acid sequence set out in amino acids 22–167 of SEQ ID NO: 4.

3. An isolated polynucleotide encoding an OB polypeptide capable of modulating body weight, the polypeptide comprising:
    a) the amino acid sequence set out in amino acids 22–167 of SEQ ID NO: 2 having an N-terminal methionine or an N-terminal polyhistidine; or
    b) the amino acid sequence set out in amino acids 22–167 of SEQ ID NO: 4 having an N-terminal methionine or an N-terminal polyhistidine.

4. An isolated polynucleotide encoding an OB polypeptide capable of modulating body weight, the polypeptice comprising:
    a) SEQ ID NO: 5;
    b) amino acids 22–166 of SEQ ID NO: 5;

c) amino acids 22–166 of SEQ ID NO: 5, having an N-terminal methionine or an N-terminal polyhistidine;

d) SEQ ID NO: 6;

e) amino acids 22–166 of SEQ ID NO: 6; or f) amino acids 22–166 of SEQ ID NO: 6 having an N-teminal methionine or an N-teminal polybistidine.

5. An isolated polynucleotide encoding an OB polypeptide capable of modulating body weight in a mammal, the polynucleotide being selected from the group consisting of:

a) a polynucleotide encoding the amino acid sequence set out in SEQ ID NO: 2;

b) a polynucleotide encoding the amino acid sequence set out in amino acids 22–167 of SEQ ID NO: 2;

c) a polynucleotide encoding the amino acid sequence set out in SEQ ID NO: 4;

d) a polynucleotide encoding the amino acid sequence set out in amino acids 22–167 of SEQ ID NO 4; and e) a polynucleotide which hybridizes under moderate stringency hybridization conditions to the polynucleotide of any one of a) through d).

6. The isolated polynucleotide of claim 5 subpart e) wherein said moderate stringency hybridization conditions are 40% formamide with 5× or 6× SSC.

7. An isolated polynucleotide comprising the DNA sequence set out as SEQ ID NO:22.

8. An isolated polynucleotide encoding an OB polypeptide capable of modulating body weight having 83% or more amino acid identity with an OB polypeptide comprising an amino acid sequence set out in SEQ ID NOS: 2, 4, 5, 6, 23 or 25.

9. An isolated mammalian genomic polynucleotide encoding an OB polypeptide capable of modulating body weight, the polypeptide comprising the amino acid sequence set out in SEQ ID NOS: 2, 4, 5, 6, 23 or 25.

10. An isolated polynucleotide encoding a conserved variant of an OB polypeptide, capable of nodulating body weight, comprising amino acids 22–167 of SEQ ID NO: 4 wherein one or more amino acids selected from the group consisting of amino acids 53, 56, 71, 85, 89, 92, 95, 98, 110, 118, 121, 122, 126, 127, 128, 129, 132, 139, 157, 159, 163 and 166 is substituted with:

a) the amino acid present in SEQ ID NO: 3 at the corresponding position; or b) a conserved amino acid.

11. An isolated polynucleotide encoding a conserved variant of an OB polypeptide, capable of modulating body weight, comprising amino acids 22–166 of SEQ ID NO: 6 wherein one or more of amino acids selected from the group consisting of amino acids 52, 55, 70, 84, 88, 91, 94, 97, 109, 117, 120, 121, 125, 126, 127, 128, 131, 138, 156, 158, 162 and 165 is substituted with:

a) the amino acid present in SEQ ID NO; 5 at the corresponding position; or b) a conserved amino acid.

12. A detectably labeled nucleic acid of at least 10 nucleotides hybridizable under moderate stringency hybridization conditions to a polynucleotide according to any one of claims 1 to 4 or 7.

13. A cloning vector which comprises a polynucleotide according to any one of claims 1 to 11.

14. An expression vector which comprises a polynucleotide according to any one of claims 1 to 11.

15. An expression vector which comprises a polynucleotide according to any one of claims 1 to 11 operatively associated with an expression control sequence.

16. The expression vector of claim 15 wherein said expression control sequence is selected from the group consisting of the immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac system, the trp system, the TAC system, the TRC system, the major operator and promoter regions of phage λ control regions of fd coat protein, 3-phosphoglycerate kinase promoter, acid phosphatase promoter, and promoters of yeast α mating factor.

17. A unicellular host transformned with a polynucleotide according to any one of claims 1 to 11.

18. The unicellular host according to claim 17 wherein the host cell is selected from the group consisting of E. coli, Pseudonomas, Bacillus, Streptomyces, yeast, CHO, R1.1, B-W, L-M, COS1, COS7, BSC1, BSC40, BMT10, and Sf9 cells.

19. The unicellular host according to claim 17 wherein the unicellular host is a yeast host selected from the group consisting of Saccharomyces, Pichia, Candida, Hansenula, and Torulopsis.

20. A mammalian cell containing a chromosomal OB polypeptide encoding DNA sequence and modified in vitro to permit higher expression of OB polypeptide by means of a homologous recombinational event consisting of inserting an expression regulatory sequence in functional proximity to the chromosomal OB polypeptide encoding sequence.

21. A cell according to claim 20 wherein the expression regulatory sequence is an OB polypeptide expression regulatory sequence and the homologous recombinational event replaces a mutant chromosomal OB polypeptide expression regulatory sequence.

22. A cell according to claim 20 wherein the expression regulatory sequence insert is not an OB polypeptide regulatory sequence.

23. A mammalian cell containing a vector comprising OB polypeptide encoding DNA sequence and modified in vitro to permit higher expression of OB polypeptide by means of a homologous recombinational event consisting of inserting an expression regulatory sequence in functional proximity to the vector OB polypeptide encoding sequence.

24. A cell according to claim 23 wherein the expression regulatory sequence is an OB polypeptide expression regulatory sequence and the homologous recombinational event replaces a mutant vector OB polypeptide expression regulatory sequence.

25. A cell according to claim 23 wherein the expression regulatory sequence insert is not an OB polypeptide regulatory sequence.

26. A method for preparing an OB polypeptide, the method comprising:

a) culturing a host according to claim 17 under conditions that provide for expression of the OB polypeptide; and b) recovering the expressed OB polypeptide.

27. A method for preparing an OB polypeptide, the method comprising:

a) culturing a host which has been transfonned or transfected with a polynucleotide encoding a polypeptide capable of modulating body weight having 83% or more amino acid identity with an OB polypeptide comprising an amino acid sequence set out in SEQ ID NOS: 2, 4, 5, 6, 23 or 25; and b) recovering the expressed OB polypeptide.

* * * * *

UNITED STATES PATENT AND TRADEMARK OFFICE
CERTIFICATE OF CORRECTION

PATENT NO.  : 5,935,810
DATED       : August 10, 1999
INVENTOR(S) : Jeffrey M. Friedman, et al.

It is certified that error appears in the above-identified patent and that said Letters Patent is hereby corrected as shown below:

On the title page, item [75]:
INVENTOR(S):   Jeffrey M. Friedman; Yiying Zhang, both of New York;
               Ricardo Proenca, Astoria, all of N.Y.

Signed and Sealed this

Twenty-eighth Day of December, 1999

Attest:

Q. TODD DICKINSON

*Attesting Officer*      Acting Commissioner of Patents and Trademarks

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
        (A) LENGTH: 2793 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: Murine ob cDNA (iii) HYPOTHETICAL: NO (iv) ANTI-SENSE: NO (vi) ORIGINAL SOURCE:
        (A) ORGANISM: Murine (ix) FEATURE:
        (A) NAME/KEY: CDS
        (B) LOCATION: 57..560

(xi) SEQUENCE DESCRIPTION: SEQ ID NO:1:

```
GGATCCCTGC TCCAGCAGCT GCAAGGTGCA AGAAGAAGAA GATCCCAGGG AGGAAA               56

ATG TGC TGG AGA CCC CTG TGT CGG TTC CTG TGG CTT TGG TCC TAT CTG            104
Met Cys Trp Arg Pro Leu Cys Arg Phe Leu Trp Leu Trp Ser Tyr Leu
 1               5                  10                  15

TCT TAT GTT CAA GCA GTG CCT ATC CAG AAA GTC CAG GAT GAC ACC AAA            152
Ser Tyr Val Gln Ala Val Pro Ile Gln Lys Val Gln Asp Asp Thr Lys
                20                  25                  30

ACC CTC ATC AAG ACC ATT GTC ACC AGG ATC AAT GAC ATT TCA CAC ACG            200
Thr Leu Ile Lys Thr Ile Val Thr Arg Ile Asn Asp Ile Ser His Thr
         35                  40                  45

CAG TCG GTA TCC GCC AAG CAG AGG GTC ACT GGC TTG GAC TTC ATT CCT            248
Gln Ser Val Ser Ala Lys Gln Arg Val Thr Gly Leu Asp Phe Ile Pro
     50                  55                  60

GGG CTT CAC CCC ATT CTG AGT TTG TCC AAG ATG GAC CAG ACT CTG GCA            296
Gly Leu His Pro Ile Leu Ser Leu Ser Lys Met Asp Gln Thr Leu Ala
 65                  70                  75                  80

GTC TAT CAA CAG GTC CTC ACC AGC CTG CCT TCC CAA AAT GTG CTG CAG            344
Val Tyr Gln Gln Val Leu Thr Ser Leu Pro Ser Gln Asn Val Leu Gln
                 85                  90                  95

ATA GCC AAT GAC CTG GAG AAT CTC CGA GAC CTC CTC CAT CTG CTG GCC            392
Ile Ala Asn Asp Leu Glu Asn Leu Arg Asp Leu Leu His Leu Leu Ala
                100                 105                 110

TTC TCC AAG AGC TGC TCC CTG CCT CAG ACC AGT GGC CTG CAG AAG CCA            440
Phe Ser Lys Ser Cys Ser Leu Pro Gln Thr Ser Gly Leu Gln Lys Pro
            115                 120                 125

GAG AGC CTG GAT GGC GTC CTG GAA GCC TCA CTC TAC TCC ACA GAG GTG            488
Glu Ser Leu Asp Gly Val Leu Glu Ala Ser Leu Tyr Ser Thr Glu Val
        130                 135                 140

GTG GCT TTG AGC AGG CTG CAG GGC TCT CTG CAG GAC ATT CTT CAA CAG            536
Val Ala Leu Ser Arg Leu Gln Gly Ser Leu Gln Asp Ile Leu Gln Gln
```

```
         145            150            155            160
TTG GAT GTT AGC CCT GAA TGC TGA AGTTTCAAAG GCCACCAGGC TCCCAAGA          588
Leu Asp Val Ser Pro Glu Cys
                165

ATCATGTAGA GGGAAGAAAC CTTGGCTTCC AGGGGTCTTC AGGAGAAGAG AGCCATGTGC       648

ACACATCCAT CATTCATTTC TCTCCCTCCT GTAGACCACC CATCCAAAGG CATGACTCCA       708

CAATGCTTGA CTCAAGTTAT CCACACAACT TCATGAGCAC AAGGAGGGGC CAGCCTGCAG       768

AGGGGACTCT CACCTAGTTC TTCAGCAAGT AGAGATAAGA GCCATCCCAT CCCCTCCATG       828

TCCCACCTGC TCCGGGTACA TGTTCCTCCG TGGGTACACG CTTCGCTGCG GCCCAGGAGA       888

GGTGAGGTAG GGATGGGTAG AGCCTTTGGG CTGTCTCAGA GTCTTTGGGA GCACCGTGAA       948

GGCTGCATCC ACACACAGCT GGAAACTCCC AAGCAGCACA CGATGGAAGC ACTTATTTAT      1008

TTATTCTGCA TTCTATTTTG GATGGATCTG AAGCAAGGCA TCAGCTTTTT CAGGCTTTGG      1068

GGGTCAGCCA GGATGAGGAA GGCTCCTGGG GTGCTGCTTT CAATCCTATT GATGGGTCTG      1128

CCCGAGGCAA ACCTAATTTT TGAGTGACTG GAAGGAAGGT TGGGATCTTC CAAACAAGAG      1188

TCTATGCAGG TAGCGCTCAA GATTGACCTC TGGTGACTGG TTTTGTTTCT ATTGTGACTG      1248

ACTCTATCCA AACACGTTTG CAGCGGCATT GCCGGGAGCA TAGGCTAGGT TATTATCAAA      1308

AGCAGATGAA TTTTGTCAAG TGTAATATGT ATCTATGTGC ACCTGAGGGT AGAGGATGTG      1368

TTAGAGGGAG GGTGAAGGAT CCGGAAGTGT TCTCTGAATT ACATATGTGT GGTAGGCTTT      1428

TCTGAAAGGG TGAGGCATTT TCTTACCTCT GTGGCCACAT AGTGTGGCTT TGTGAAAAGG      1488

ACAAAGGAGT TGACTCTTTC CGGAACATTT GGAGTGTACC AGGCACCCTT GGAGGGGCTA      1548

AAGCTACAGG CCTTTTGTTG GCATATTGCT GAGCTCAGGG AGTGAGGGCC CCACATTTGA      1608

GACAGTGAGC CCCAAGAAAA GGGTCCCTGG TGTAGATCTC CAAGGTTGTC CAGGGTTGAT      1668

CTCACAATGC GTTTCTTAAG CAGGTAGACG TTTGCATGCC AATATGTGGT TCTCATCTGA      1728

TTGGTTCATC CAAAGTAGAA CCCTGTCTCC CACCCATTCT GTGGGGAGTT TTGTTCCAGT      1788

GGGAATGAGA AATCACTTAG CAGATGGTCC TGAGCCCTGG GCCAGCACTG CTGAGGAAGT      1848

GCCAGGGCCC CAGGCCAGGC TGCCAGAATT GCCCTTCGGG CTGGAGGATG AACAAAGGGG      1908

CTTGGGTTTT TCCATCACCC CTGCACCCTA TGTCACCATC AAACTGGGGG GCAGATCAGT      1968

GAGAGGACAC TTGATGGAAA GCAATACACT TTAAGACTGA GCACAGTTTC GTGCTCAGCT      2028

CTGTCTGGTG CTGTGAGCTA GAGAAGCTCA CCACATACAT ATAAAAATCA GAGGCTCATG      2088

TCCCTGTGGT TAGACCCTAC TCGCGGCGGT GTACTCCACC ACAGCAGCAC CGCACCGCTG      2148

GAAGTACAGT GCTGTCTTCA ACAGGTGTGA AAGAACCTGA GCTGAGGGTG ACAGTGCCCA      2208

GGGGAACCCT GCTTGCAGTC TATTGCATTT ACATACCGCA TTTCAGGGCA CATTAGCATC      2268

CACTCCTATG GTAGCACACT GTTGACAATA GGACAAGGGA TAGGGGTTGA CTATCCCTTA      2328

TCCAAAATGC TTGGGACTAG AAGAGTTTTG GATTTTAGAG TCTTTTCAGG CATAGGTATA      2388

TTTGAGTATA TATAAAATGA GATATCTTGG GGATGGGGCC CAAGTATAAA CATGAAGTTC      2448

ATTTATATTT CATAATACCG TATAGACACT GCTTGAAGTG TAGTTTTATA CAGTGTTTTA      2508

AATAACGTTG TATGCATGAA AGACGTTTTT ACAGCATGAA CCTGTCTACT CATGCCAGCA      2568

CTCAAAAACC TTGGGGTTTT GGAGCAGTTT GGATCTTGGG TTTTCTGTTA AGAGATGGTT      2628

AGCTTATACC TAAAACCATA ATGGCAAACA GGCTGCAGGA CCAGACTGGA TCCTCAGCCC      2688

TGAAGTGTGC CCTTCCAGCC AGGTCATACC CTGTGGAGGT GAGCGGGATC AGGTTTTGTG      2748

GTGCTAAGAG AGGAGTTGGA GGTAGATTTT GGAGGATCTG AGGGC                     2793
```

(2) INFORMATION FOR SEQ ID NO:2:

(i) SEQUENCE CHARACTERISTICS:
        (A) LENGTH: 167 amino acids
        (B) TYPE: amino acid
        (D) TOPOLOGY: linear (ii) MOLECULE TYPE: protein
        (A) DESCRIPTION: Murine ob polypeptide (xi) SEQUENCE DESCRIPTION: SEQ ID NO:2:

```
Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ala Lys Gln Arg Val Thr Gly Leu Asp Phe Ile Pro
        50                  55                  60

Gly Leu His Pro Ile Leu Ser Leu Ser Lys Met Asp Gln Thr Leu Ala
 65                  70                  75                  80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
                100                 105                 110

Phe Ser Lys Ser Cys Ser Leu Pro Gln Thr Ser Gly Leu Gln Lys Pro
            115                 120                 125

Glu Ser Leu Asp Gly Val Leu Glu Ala Ser Leu Tyr Ser Thr Glu Val
        130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165
```

(2) INFORMATION FOR SEQ ID NO:3:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: cDNA
        (A) DESCRIPTION: Human ob cDNA where N represents any
            nucleotide (iii) HYPOTHETICAL: NO (iv) ANTI-SENSE: NO (vi) ORIGINAL SOURCE:
        (A) ORGANISM: Human (ix) FEATURE:
        (A) NAME/KEY: CDS
        (B) LOCATION: 46..546

(xi) SEQUENCE DESCRIPTION: SEQ ID NO:3:

```
NNNGNNGTTG CAAGGCCCAA GAAGCCCANN NTCCTGGGAA GGAAA ATG CAT TGG        54
                                              Met His Trp
                                               1

GGA ACC CTG TGC GGA TTC TTG TGG CTT TGG CCC TAT CTT TTC TAT GTC    102
Gly Thr Leu Cys Gly Phe Leu Trp Leu Trp Pro Tyr Leu Phe Tyr Val
  5                  10                  15
```

-continued

```
CAA GCT GTG CCC ATC CAA AAA GTC CAA GAT GAC ACC AAA ACC CTC ATC        150
Gln Ala Val Pro Ile Gln Lys Val Gln Asp Asp Thr Lys Thr Leu Ile
 20                  25                  30                  35

AAG ACA ATT GTC ACC AGG ATC AAT GAC ATT TCA CAC ACG CAG TCA GTC        198
Lys Thr Ile Val Thr Arg Ile Asn Asp Ile Ser His Thr Gln Ser Val
                 40                  45                  50

TCC TCC AAA CAG AAA GTC ACC GGT TTG GAC TTC ATT CCT GGG CTC CAC        246
Ser Ser Lys Gln Lys Val Thr Gly Leu Asp Phe Ile Pro Gly Leu His
             55                  60                  65

CCC ATC CTG ACC TTA TCC AAG ATG GAC CAG ACA CTG GCA GTC TAC CAA        294
Pro Ile Leu Thr Leu Ser Lys Met Asp Gln Thr Leu Ala Val Tyr Gln
         70                  75                  80

CAG ATC CTC ACC AGT ATG CCT TCC AGA AAC GTG ATC CAA ATA TCC AAC        342
Gln Ile Leu Thr Ser Met Pro Ser Arg Asn Val Ile Gln Ile Ser Asn
 85                  90                  95

GAC CTG GAG AAC CTC CGG GAT CTT CTT CAC GTG CTG GCC TTC TCT AAG        390
Asp Leu Glu Asn Leu Arg Asp Leu Leu His Val Leu Ala Phe Ser Lys
100                 105                 110                 115

AGC TGC CAC TTG CCC TGG GCC AGT GGC CTG GAG ACC TTG GAC AGC CTG        438
Ser Cys His Leu Pro Trp Ala Ser Gly Leu Glu Thr Leu Asp Ser Leu
                120                 125                 130

GGG GGT GTC CTG GAA GCT TCA GGC TAC TCC ACA GAG GTG GTG GCC CTG        486
Gly Gly Val Leu Glu Ala Ser Gly Tyr Ser Thr Glu Val Val Ala Leu
            135                 140                 145

AGC AGG CTG CAG GGG TCT CTG CAG GAC ATG CTG TGG CAG CTG GAC CTC        534
Ser Arg Leu Gln Gly Ser Leu Gln Asp Met Leu Trp Gln Leu Asp Leu
        150                 155                 160

AGC CCT GGG TGC TGAGGCCTT GAAGGTCACT CTTCCTGCAA GGACTNACGT             585
Ser Pro Gly Cys
    165

TAAGGGAAGG AACTCTGGTT TCCAGGTATC TCCAGGATTG AAGAGCATTG CATGGACACC      645

CCTTATCCAG GACTCTGTCA ATTTCCCTGA CTCCTCTAAG CCACTCTTCC AAAGG           700

(2) INFORMATION FOR SEQ ID NO:4:

(i) SEQUENCE CHARACTERISTICS:
        (A) LENGTH: 167 amino acids
        (B) TYPE: amino acid
        (D) TOPOLOGY: linear (ii) MOLECULE TYPE: protein
         (A) DESCRIPTION: Human ob polypeptide (vi) ORIGINAL SOURCE: Human (xi) SEQUENCE DESCRIPTION: SEQ ID NO:4:

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
             35                  40                  45

Gln Ser Val Ser Ser Lys Gln Lys Val Thr Gly Leu Asp Phe Ile Pro
 50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
             100                 105                 110
```

```
Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

(2) INFORMATION FOR SEQ ID NO:5:

(i) SEQUENCE CHARACTERISTICS:
        (A) LENGTH: 166 amino acids
        (B) TYPE: amino acid
        (D) TOPOLOGY: linear (ii) MOLECULE TYPE: protein
        (A) DESCRIPTION: Murine ob polypeptide lacking Gln at position
            49

(vi) ORIGINAL SOURCE:
        (A) ORGANISM: Murine (xi) SEQUENCE DESCRIPTION: SEQ ID NO:5:

```
Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Ser Val Ser Ala Lys Gln Arg Val Thr Gly Leu Asp Phe Ile Pro Gly
        50                  55                  60

Leu His Pro Ile Leu Ser Leu Ser Lys Met Asp Gln Thr Leu Ala Val
65                  70                  75                  80

Tyr Gln Gln Val Leu Thr Ser Leu Pro Ser Gln Asn Val Leu Gln Ile
                85                  90                  95

Ala Asn Asp Leu Glu Asn Leu Arg Asp Leu Leu His Leu Leu Ala Phe
                100                 105                 110

Ser Lys Ser Cys Ser Leu Pro Gln Thr Ser Gly Leu Gln Lys Pro Glu
        115                 120                 125

Ser Leu Asp Gly Val Leu Glu Ala Ser Leu Tyr Ser Thr Glu Val Val
130                 135                 140

Ala Leu Ser Arg Leu Gln Gly Ser Leu Gln Asp Ile Leu Gln Gln Leu
145                 150                 155                 160

Asp Val Ser Pro Glu Cys
                165
```

(2) INFORMATION FOR SEQ ID NO:6:

(i) SEQUENCE CHARACTERISTICS:
        (A) LENGTH: 166 amino acids
        (B) TYPE: amino acid
        (D) TOPOLOGY: linear (ii) MOLECULE TYPE: protein
        (A) DESCRIPTION: Human ob polypeptide lacking Gln at position
            49

(vi) ORIGINAL SOURCE:
        (A) ORGANISM: Human (xi) SEQUENCE DESCRIPTION: SEQ ID NO:6:

```
Met His Trp Gly Thr Leu Cys Gly Phe Leu Trp Leu Trp Pro Tyr Leu
```

```
              1               5              10              15

Phe Tyr Val Gln Ala Val Pro Ile Gln Lys Val Gln Asp Asp Thr Lys
                         20                  25                  30

Thr Leu Ile Lys Thr Ile Val Thr Arg Ile Asn Asp Ile Ser His Thr
                     35                  40                  45

Ser Val Ser Ser Lys Gln Lys Val Thr Gly Leu Asp Phe Ile Pro Gly
             50                  55                  60

Leu His Pro Ile Leu Thr Leu Ser Lys Met Asp Gln Thr Leu Ala Val
         65                  70                  75                  80

Tyr Gln Gln Ile Leu Thr Ser Met Pro Ser Arg Asn Val Ile Gln Ile
                         85                  90                  95

Ser Asn Asp Leu Glu Asn Leu Arg Asp Leu Leu His Val Leu Ala Phe
                    100                 105                 110

Ser Lys Ser Cys His Leu Pro Trp Ala Ser Gly Leu Glu Thr Leu Asp
                115                 120                 125

Ser Leu Gly Gly Val Leu Glu Ala Ser Gly Tyr Ser Thr Glu Val Val
            130                 135                 140

Ala Leu Ser Arg Leu Gln Gly Ser Leu Gln Asp Met Leu Trp Gln Leu
        145                 150                 155                 160

Asp Leu Ser Pro Gly Cys
                    165
```

(2) INFORMATION FOR SEQ ID NO:7:

(i) SEQUENCE CHARACTERISTICS:
        (A) LENGTH: 176 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: exon 2G7

(iii) HYPOTHETICAL: NO (iv) ANTI-SENSE: NO (xi) SEQUENCE DESCRIPTION: SEQ ID NO:7:

```
GTGCAAGAAG AAGAAGATCC CAGGGCAGGA AAATGTGCTG GAGACCCCTG TGTCGGGTCC       60
NGTGGNTTTG GTCCTATCTG TCTTATGTNC AAGCAGTGCC TATCCAGAAA GTCCAGGATG      120
ACACCAAAAG CCTCATCAAG ACCATTGTCA NCAGGATCAC TGANATTTCA CACACG          176
```

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 5 primer for exon 2G7

(iii) HYPOTHETICAL: NO (iv) ANTI-SENSE: NO (xi) SEQUENCE DESCRIPTION: SEQ ID NO:8:

```
CCAGGGCAGG AAAATGTG                                                     18
```

(2) INFORMATION FOR SEQ ID NO:9:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 3 primer for exon 2G7

(iii) HYPOTHETICAL: NO (iv) ANTI-SENSE: YES (xi) SEQUENCE DESCRIPTION: SEQ ID NO:9:

CATCCTGGAC TTTCTGGATA GG                                              22

(2) INFORMATION FOR SEQ ID NO:10:

(i) SEQUENCE CHARACTERISTICS:
        (A) LENGTH: 23 amino acids
        (B) TYPE: amino acid
        (D) TOPOLOGY: linear (ii) MOLECULE TYPE: peptide
        (A) DESCRIPTION: putative N-terminal signal peptide (xi) SEQUENCE DESCRIPTION: SEQ ID NO:10:

Met Cys Trp Arg Pro Leu Cys Arg Phe Leu Trp Leu Trp Ser Tyr Leu
    1               5                   10                  15

Ser Tyr Val Gln Ala Val Pro
                20

(2) INFORMATION FOR SEQ ID NO:11:

(i) SEQUENCE CHARACTERISTICS:
        (A) LENGTH: 287 base pairs
        (B) TYPE: nucleic acid
        (C) STRANDEDNESS: double
        (D) TOPOLOGY: circular (ii) MOLECULE TYPE: DNA (plasmid)
        (A) DESCRIPTION: pET-15b expression vector (iii) HYPOTHETICAL: NO (iv) ANTI-SENSE: NO (ix) FEATURE:
        (A) NAME/KEY: T7 promoter
        (B) LOCATION: 20..37

(ix) FEATURE:
        (A) NAME/KEY: lac operator
        (B) LOCATION: 39..64

(ix) FEATURE:
        (A) NAME/KEY: CDS
        (B) LOCATION: 108..243

(ix) FEATURE:
        (A) NAME/KEY: His-Tag
        (B) LOCATION: 123..137

(ix) FEATURE:
        (A) NAME/KEY: Thrombin cleavage site
        (B) LOCATION: 184..196

(xi) SEQUENCE DESCRIPTION: SEQ ID NO:11:

AGATCTCGAT CCCGCGAAAT TAATACGACT CACTATAGGG GAATTGTGAG CGGATAACAA        60

TTCCCCTCTA CAAATAATTT TGTTTAACTT TAAGAAGGAG ATATACC ATG GGC AGC         116
                                                    Met Gly Ser
                                                    1

AGC CAT CAT CAT CAT CAT CAC AGC AGC GGC CTG GTG CCG CGC GGC AGC         164

```
Ser His His His His His Ser Ser Gly Leu Val Pro Arg Gly Ser
    5                   10                  15

CAT ATG CTC GAG GAT CCC GCT GCT AAC AAA GCC CGA AAG GAA GCT GAG        212
His Met Leu Glu Asp Pro Ala Ala Asn Lys Ala Arg Lys Glu Ala Glu
 20              25                  30                  35

TTG GCT GCT GCC ACC GCT GAG CAA TAA CTA G CATAACCCCT TGGGGCCTCT        263
Leu Ala Ala Ala Thr Ala Glu Gln  *
                40

AAACGGGTCT TGAGGGGTTT TTTG                                             287

(2) INFORMATION FOR SEQ ID NO:12:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:12:

Met Gly Ser Ser His His His His His His Ser Ser Gly Leu Val Pro
 1               5                   10                  15

Arg Gly Ser His Met Leu Glu Asp Pro Ala Ala Asn Lys Ala Arg Lys
                20                  25                  30

Glu Ala Glu Leu Ala Ala Ala Thr Ala Glu Gln
            35                  40

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Murine 5 primer (iii) HYPOTHETICAL: NO (iv) ANTI-SENSE: NO (xi) SEQUENCE DESCRIPTION: SEQ ID NO:13:

CTTATGTTCA TATGGTGCCG ATCCAGAAAG TC                                 32

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: Murine 3 primer (iii) HYPOTHETICAL: NO (iv) ANTI-SENSE: Yes (xi) SEQUENCE DESCRIPTION: SEQ ID NO:14:

TCCCTCTACA TATGTCTTGG GAGCCTGGTG GC                                 32

(2) INFORMATION FOR SEQ ID NO:15:

(i) SEQUENCE CHARACTERISTICS:
        (A) LENGTH: 32 base pairs
        (B) TYPE: nucleic acid
```

```
           (C) STRANDEDNESS: single
           (D) TOPOLOGY: linear (ii) MOLECULE TYPE: DNA (primer)
           (A) DESCRIPTION: Human 5 primer (iii) HYPOTHETICAL: NO (iv) ANTI-SENSE: NO (xi) SEQUENCE DESCRIPTION: SEQ ID NO:15:

TCTATGTCCA TATGGTGCCG ATCCAAAAAG TC                                    32

(2) INFORMATION FOR SEQ ID NO:16:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: DNA (primer)
           (A) DESCRIPTION: Human 3 primer (iii) HYPOTHETICAL: NO (iv) ANTI-SENSE: Yes (xi) SEQUENCE DESCRIPTION: SEQ ID NO:16:

TTCCTTCCCA TATGGTACTC CTTGCAGGAA GA                                    32

(2) INFORMATION FOR SEQ ID NO:17:

(i) SEQUENCE CHARACTERISTICS:
           (A) LENGTH: 11 base pairs
           (B) TYPE: nucleic acid
           (C) STRANDEDNESS: double
           (D) TOPOLOGY: linear (ii) MOLECULE TYPE: cDNA
           (A) DESCRIPTION: Splice acceptor site in ob (iii) HYPOTHETICAL: NO (iv) ANTI-SENSE: NO (ix) FEATURE:
           (A) NAME/KEY: Splice acceptor site (xi) SEQUENCE DESCRIPTION: SEQ ID NO:17:

AGCAGTCGGT A                                                           11

(2) INFORMATION FOR SEQ ID NO:18:

(i) SEQUENCE CHARACTERISTICS:
           (A) LENGTH: 16 amino acids
           (B) TYPE: amino acid
           (D) TOPOLOGY: unknown (ii) MOLECULE TYPE: peptide
           (A) DESCRIPTION: ob peptide fragment (v) FRAGMENT TYPE: internal (vi) ORIGINAL SOURCE:
           (A) ORGANISM: Murine (xi) SEQUENCE DESCRIPTION: SEQ ID NO:18:

Val Pro Ile Gln Lys Val Gln Asp Asp Thr Lys Thr Leu Ile Lys Thr
        1               5                  10                  15

(2) INFORMATION FOR SEQ ID NO:19:
```

```
    (i) SEQUENCE CHARACTERISTICS:
        (A) LENGTH: 15 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: internal (vi) ORIGINAL SOURCE:
        (A) ORGANISM: Murine (xi) SEQUENCE DESCRIPTION: SEQ ID NO:19:

Leu His Pro Ile Leu Ser Leu Ser Lys Met Asp Gln Thr Leu Ala
   1               5                   10                  15

(2) INFORMATION FOR SEQ ID NO:20:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: internal (vi) ORIGINAL SOURCE:
        (A) ORGANISM: Murine (xi) SEQUENCE DESCRIPTION: SEQ ID NO:20:

Ser Lys Ser Cys Ser Leu Pro Gln Thr Ser Gly Leu Gln Lys Pro Glu
   1               5                   10                  15

Ser Leu Asp (2) INFORMATION FOR SEQ ID NO:21:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide
        (A) DESCRIPTION: ob peptide fragment (v) FRAGMENT TYPE: Carboxyl terminal (vi) ORIGINAL SOURCE:
        (A) ORGANISM: Murine (xi) SEQUENCE DESCRIPTION: SEQ ID NO:21:

Ser Arg Leu Gln Gly Ser Leu Gln Asp Ile Leu Gln Gln Leu Asp Val
   1               5                   10                  15

Ser Pro Glu Cys
               20

(2) INFORMATION FOR SEQ ID NO:22:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: portion of the human ob gene including
                        noncoding (iii) HYPOTHETICAL: NO
```

(iv) ANTI-SENSE: NO (vi) ORIGINAL SOURCE:
            (A) ORGANISM: Human (ix) FEATURE:
            (A) NAME/KEY: CDS
            (B) LOCATION: 38..181

(ix) FEATURE:
            (A) NAME/KEY: 5 region of first intron
            (B) LOCATION: 182..414

(ix) FEATURE:
            (A) NAME/KEY: 5 noncoding sequence of the human ob gene from
                          which
            (B) LOCATION: 11..28

(ix) FEATURE:
            (A) NAME/KEY: intronic sequence of the human ob gene from
                          which the
            (B) LOCATION: 241..260

(xi) SEQUENCE DESCRIPTION: SEQ ID NO:22:

```
GGTTGCAAGG CCCAAGAAGC CCATCCTGGG AAGGAAA ATG CAT TGG GGA ACC CTG      55
                                         Met His Trp Gly Thr Leu
                                          1               5

TGC GGA TTC TTG TGG CTT TGG CCC TAT CTT TTC TAT GTC CAA GCT GTG       103
Cys Gly Phe Leu Trp Leu Trp Pro Tyr Leu Phe Tyr Val Gln Ala Val
         10                  15                  20

CCC ATC CAA AAA GTC CAA GAT GAC ACC AAA ACC CTC ATC AAG ACA ATT       151
Pro Ile Gln Lys Val Gln Asp Asp Thr Lys Thr Leu Ile Lys Thr Ile
            25                  30                  35

GTC ACC AGG ATC AAT GAC ATT TCA CAC ACG GTAAGGAGAG TATGCGGGGA         201
Val Thr Arg Ile Asn Asp Ile Ser His Thr
        40                  45

CAAAGTAGAA CTGCAGCCAG CCCAGCACTG GCTCCTAGTG GCACTGGACC CAGATAGTCC     261

AAGAAACATT TATTGAACGC CTCCTGAATG CCAGGCACCT ACTGGAAGCT GAGAAGGATT     321

TTGGATAGCA CAGGGCTCCA CTCTTTCTGG TTGTTTCTTN TGGCCCCCTC TGCCTGCTGA     381

GATNCCAGGG GTTAGNGGTT CTTAATTCCT AAA                                  414
```

(2) INFORMATION FOR SEQ ID NO:23:

(i) SEQUENCE CHARACTERISTICS:
            (A) LENGTH: 48 amino acids
            (B) TYPE: amino acid
            (D) TOPOLOGY: linear (ii) MOLECULE TYPE: protein
            (A) DESCRIPTION: N-terminal portion of the human ob protein (xi) SEQUENCE DESCRIPTION: SEQ ID NO:23:

```
Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
             20                  25                  30

Thr Leu Ile Lys Thr Ile Val Thr Arg Ile Asn Asp Ile Ser His Thr
         35                  40                  45
```

(2) INFORMATION FOR SEQ ID NO:24:

(i) SEQUENCE CHARACTERISTICS:
            (A) LENGTH: 801 base pairs
            (B) TYPE: nucleic acid
            (C) STRANDEDNESS: double
            (D) TOPOLOGY: linear (ii) MOLECULE TYPE: DNA (genomic)
    (A) DESCRIPTION: portion of the human ob gene including 3
                     region of (iii) HYPOTHETICAL: NO (iv) ANTI-SENSE: NO (vi) ORIGINAL SOURCE:
    (A) ORGANISM: Human (ix) FEATURE:
    (A) NAME/KEY: CDS
    (B) LOCATION: 291..648

(ix) FEATURE:
    (A) NAME/KEY: 3 of first intron
    (B) LOCATION: 1..290

(ix) FEATURE:
    (A) NAME/KEY: intronic sequence of the human ob gene HOB from
                  which
    (B) LOCATION: 250..269

(ix) FEATURE:
    (A) NAME/KEY: 3 noncoding sequence of the human ob gene from
                  which
    (B) LOCATION: 707..728

(xi) SEQUENCE DESCRIPTION: SEQ ID NO:24:

```
CTGGTTCTTT CAGGAAGAGG CCATGTAAGA GAAAGGAATT GACCTAGGGA AAATTGGCCT      60

GGGAAGTGGA GGGAACGGAT GGTGTGGGAA AAGCAGGAAT CTCGGAGACC AGCTTAGAGG     120

CTTGGCAGTC ACCTGGGTGC AGGANACAAG GGCCTGAGCC AAAGTGGTGA GGGAGGGTGG     180

AAGGAGACAG CCCAGAGAAT GACCCTCCAT GCCCACGGGG AAGGCAGAGG GCTCTGAGAG     240

CGATTCCTCC CACATGCTGA GCACTTGTTC TCCCTCTTCC TCCTNCATAG CAG TCA        296
                                                       Gln Ser
                                                         1

GTC TCC TCC AAA CAG AAA GTC ACC GGT TTG GAC TTC ATT CCT GGG CTC      344
Val Ser Ser Lys Gln Lys Val Thr Gly Leu Asp Phe Ile Pro Gly Leu
        5                   10                  15

CAC CCC ATC CTG ACC TTA TCC AAG ATG GAC CAG ACA CTG GCA GTC TAC      392
His Pro Ile Leu Thr Leu Ser Lys Met Asp Gln Thr Leu Ala Val Tyr
 20                  25                  30

CAA CAG ATC CTC ACC AGT ATG CCT TCC AGA AAC GTG ATC CAA ATA TCC      440
Gln Gln Ile Leu Thr Ser Met Pro Ser Arg Asn Val Ile Gln Ile Ser
 35                  40                  45                  50

AAC GAC CTG GAG AAC CTC CGG GAT CTT CTT CAC GTG CTG GCC TTC TCT      488
Asn Asp Leu Glu Asn Leu Arg Asp Leu Leu His Val Leu Ala Phe Ser
                 55                  60                  65

AAG AGC TGC CAC TTG CCC TGG GCC AGT GGC CTG GAG ACC TTG GAC AGC      536
Lys Ser Cys His Leu Pro Trp Ala Ser Gly Leu Glu Thr Leu Asp Ser
         70                  75                  80

CTG GGG GGT GTC CTG GAA GCT TCA GGC TAC TCC ACA GAG GTG GTG GCC      584
Leu Gly Gly Val Leu Glu Ala Ser Gly Tyr Ser Thr Glu Val Val Ala
     85                  90                  95

CTG AGC AGG CTG CAG GGG TCT CTG CAG GAC ATG CTG TGG CAG CTG GAC      632
Leu Ser Arg Leu Gln Gly Ser Leu Gln Asp Met Leu Trp Gln Leu Asp
100                 105                 110

CTC AGC CCT GGG TGC T GAGGCCTTGA AGGTCACTCT TCCTGCAAGG ACTACGTTAA    688
Leu Ser Pro Gly Cys
115

GGGAAGGAAC TCTGGCTTTC CAGGTATCTC CAGGATTGAA GAGCATTGCA TGGACACCCC    748

TTATCCAGGA CTCTGTCAAT TTCCCTGACT CCTCTAAGCC ACTCTTCCAA AGG           801
```

(2) INFORMATION FOR SEQ ID NO:25:

(i) SEQUENCE CHARACTERISTICS:
        (A) LENGTH: 119 amino acids
        (B) TYPE: amino acid
        (D) TOPOLOGY: linear (ii) MOLECULE TYPE: protein
        (A) DESCRIPTION: C-terminal portion of the human ob protein (xi) SEQUENCE DESCRIPTION: SEQ ID NO:25:

```
Gln Ser Val Ser Ser Lys Gln Lys Val Thr Gly Leu Asp Phe Ile Pro
 1               5                  10                  15
Gly Leu His Pro Ile Leu Thr Leu Ser Lys Met Asp Gln Thr Leu Ala
            20                  25                  30
Val Tyr Gln Gln Ile Leu Thr Ser Met Pro Ser Arg Asn Val Ile Gln
        35                  40                  45
Ile Ser Asn Asp Leu Glu Asn Leu Arg Asp Leu Leu His Val Leu Ala
    50                  55                  60
Phe Ser Lys Ser Cys His Leu Pro Trp Ala Ser Gly Leu Glu Thr Leu
65                  70                  75                  80
Asp Ser Leu Gly Gly Val Leu Glu Ala Ser Gly Tyr Ser Thr Glu Val
                85                  90                  95
Val Ala Leu Ser Arg Leu Gln Gly Ser Leu Gln Asp Met Leu Trp Gln
            100                 105                 110
Leu Asp Leu Ser Pro Gly Cys
        115
```

(2) INFORMATION FOR SEQ ID NO:26:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (v) FRAGMENT TYPE: internal (vi) ORIGINAL SOURCE:
        (A) ORGANISM: pichia yeast (xi) SEQUENCE DESCRIPTION: SEQ ID NO:26:

```
Leu Glu Lys Arg Glu Ala Glu Ala
 1               5
```

(2) INFORMATION FOR SEQ ID NO:27:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (v) FRAGMENT TYPE: internal (vi) ORIGINAL SOURCE:
        (A) ORGANISM: pichia yeast (xi) SEQUENCE DESCRIPTION: SEQ ID NO:27:

```
Glu Ala Glu Ala
 1
```

(2) INFORMATION FOR SEQ ID NO:28:

```
    (i) SEQUENCE CHARACTERISTICS:
        (A) LENGTH: 4 amino acids
        (B) TYPE: amino acid
        (D) TOPOLOGY: unknown (ii) MOLECULE TYPE: peptide (v) FRAGMENT TYPE: Internal (vi) ORIGINAL SOURCE:
        (A) ORGANISM: pichia yeast (xi) SEQUENCE DESCRIPTION: SEQ ID NO:28:

Leu Glu Lys Arg
 1

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HOB 1gF DNA primer generated from the 5
                        noncoding (iii) HYPOTHETICAL: NO (iv) ANTI-SENSE: NO (xi) SEQUENCE DESCRIPTION: SEQ ID NO:29:

CCCAAGAAGC CCATCCTG                                                18

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HOB 1gR DNA primer generated from the first (iii) HYPOTHETICAL: NO (iv) ANTI-SENSE: YES (xi) SEQUENCE DESCRIPTION: SEQ ID NO:30:

GACTATCTGG GTCCAGTGCC                                              20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HOB 2gF DNA primer generated from the first (iii) HYPOTHETICAL: NO (iv) ANTI-SENSE: NO (xi) SEQUENCE DESCRIPTION: SEQ ID NO:31:

CCACATGCTG AGCACTTGTT                                              20

(2) INFORMATION FOR SEQ ID NO:32:
```

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HOB 2gR DNA primer generated from the 3
                        noncoding sequence of t (iii) HYPOTHETICAL: NO (iv) ANTI-SENSE: YES (xi) SEQUENCE DESCRIPTION: SEQ ID NO:32:

CTTCAATCCT GGAGATACCT GG                                                   22

(2) INFORMATION FOR SEQ ID NO:33:

(i) SEQUENCE CHARACTERISTICS:
        (A) LENGTH: 51 base pairs
        (B) TYPE: nucleic acid
        (C) STRANDEDNESS: double
        (D) TOPOLOGY: circular (ii) MOLECULE TYPE: DNA
        (A) DESCRIPTION: pPIC.9 cloning site (iii) HYPOTHETICAL: NO (iv) ANTI-SENSE: NO (xi) SEQUENCE DESCRIPTION: SEQ ID NO:33:

CTCGAGAAAA GAGAGGCTGA AGCTTACGTA GAATTCCCTA GGCCGGCCGG G                    51

(2) INFORMATION FOR SEQ ID NO:34:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 5 primer for amplifying human ob cDNA
                        sequence (iii) HYPOTHETICAL: NO (iv) ANTI-SENSE: NO (xi) SEQUENCE DESCRIPTION: SEQ ID NO:34:

GTATCTCTCG AGAAAAGAGT GCCCATCCAA AAAGTCCAAG                                 40

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 3 primer for amplifying human ob cDNA
                        sequence (iii) HYPOTHETICAL: NO (iv) ANTI-SENSE: YES (xi) SEQUENCE DESCRIPTION: SEQ ID NO:35:

GCGCGAATTC TCAGCACCCA GGGCTGAGGT C                                          31

(2) INFORMATION FOR SEQ ID NO:36:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 5 primer for amplifying murine ob cDNA
                sequence (iii) HYPOTHETICAL: NO (iv) ANTI-SENSE: NO (xi) SEQUENCE DESCRIPTION: SEQ ID NO:36:

GTATCTCTCG AGAAAAGAGT GCCTATCCAG AAAGTCCAGG                      40

(2) INFORMATION FOR SEQ ID NO:37:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (primer)
        (A) DESCRIPTION: PCR 3 primer for amplifying murine ob cDNA
                sequence (iii) HYPOTHETICAL: NO (iv) ANTI-SENSE: YES (xi) SEQUENCE DESCRIPTION: SEQ ID NO:37:

GCGCGAATTC TCAGCATTCA GGGCTAACAT C                                 31

(2) INFORMATION FOR SEQ ID NO:38:

(i) SEQUENCE CHARACTERISTICS:
        (A) LENGTH: 4 amino acids
        (B) TYPE: amino acid
        (D) TOPOLOGY: linear (ii) MOLECULE TYPE: protein
        (A) DESCRIPTION: tetrapeptide at N-terminus of renatured
                murine (vi) ORIGINAL SOURCE:
        (A) ORGANISM: Murine (xi) SEQUENCE DESCRIPTION: SEQ ID NO:38:

Gly Ser His Met